US008232456B2

(12) United States Patent
Long et al.

(10) Patent No.: US 8,232,456 B2

(45) Date of Patent: Jul. 31, 2012

(54) CORN EVENT MIR162

(75) Inventors: Nykoll Long, Research Triangle Park, NC (US); Jeff Bottoms, Research Triangle Park, NC (US); Moez Meghji, Bloomington, IL (US); Hope Hart, Research Triangle Park, NC (US); Qiudeng Que, Research Triangle Park, NC (US); Derrick Pulliam, Durham, NC (US)

(73) Assignee: Syngenta Participations AG, Basel (CH)

( * ) Notice: Subject to any disclaimer, the term of this patent is extended or adjusted under 35 U.S.C. 154(b) by 554 days.

(21) Appl. No.: 12/301,824

(22) PCT Filed: May 24, 2007

(86) PCT No.: PCT/US2007/012301

§ 371 (c)(1),
(2), (4) Date: Jul. 15, 2009

(87) PCT Pub. No.: WO2007/142840

PCT Pub. Date: Dec. 13, 2007

(65) Prior Publication Data

US 2009/0300784 A1 Dec. 3, 2009

Related U.S. Application Data

(60) Provisional application No. 60/810,499, filed on Jun. 3, 2006.

(51) Int. Cl.
*C12N 15/82* (2006.01)
*A01H 1/00* (2006.01)

(52) U.S. Cl. ....... 800/302; 435/419; 536/23.7; 800/266; 800/275

(58) Field of Classification Search ........................ None
See application file for complete search history.

(56) References Cited

U.S. PATENT DOCUMENTS

| | | | | |
|---|---|---|---|---|
| 4,808,426 A * | 2/1989 | Strop et al. | .................... | 426/417 |
| 5,877,012 A * | 3/1999 | Estruch et al. | ............. | 435/252.3 |

FOREIGN PATENT DOCUMENTS

| | | |
|---|---|---|
| WO | 98/44137 | 10/1998 |
| WO | WO 98/44137 * | 10/1998 |
| WO | WO03/052073 A2 | 6/2003 |
| WO | WO03/052073 A3 | 6/2003 |

OTHER PUBLICATIONS

Syngenta Participations AG, International Application Ser. No. PCT/US07/012301, International Search Report, (Sep. 30, 2008).
Syngenta Participations AG, International Application Ser. No. PCT/US07/012301, Written Opinion, (Sep. 30, 2008).

* cited by examiner

*Primary Examiner* — David H Kruse
(74) *Attorney, Agent, or Firm* — Christopher L. Leming

(57) ABSTRACT

A novel transgenic corn event designated MIR162 is disclosed. The invention relates to nucleic acids from event MIR162. The invention also relates to assays for detecting the presence of the MIR162 event based on DNA sequences of the recombinant constructs inserted into the corn genome that resulted in the MIR162 event and of genomic sequences flanking the insertion sites. The invention further relates to corn plants comprising the genotype of MIR162 and to methods for producing a corn plant by crossing a corn plant comprising the MIR162 genotype with itself or another corn variety. Seeds of corn plants comprising the MIR162 genotype are also objects of the present invention. The invention also relates to methods of controlling insects using MIR162 corn plants.

11 Claims, No Drawings

SEQUENCE LISTING

```
<160> NUMBER OF SEQ ID NOS: 107

<210> SEQ ID NO 1
<211> LENGTH: 2370
<212> TYPE: DNA
<213> ORGANISM: Artificial Sequence
<220> FEATURE:
<223> OTHER INFORMATION: vip3Aa20 coding sequence

<400> SEQUENCE: 1

atgaacaaga acaacaccaa gctgagcacc cgcgccctgc cgagcttcat cgactacttc      60

aacggcatct acggcttcgc caccggcatc aaggacatca tgaacatgat cttcaagacc     120

gacaccggcg gcgacctgac cctggacgag atcctgaaga accagcagct gctgaacgac     180

atcagcggca agctggacgg cgtgaacggc agcctgaacg acctgatcgc ccagggcaac     240

ctgaacaccg agctgagcaa ggagatcctt aagatcgcca acgagcagaa ccaggtgctg     300

aacgacgtga acaacaagct ggacgccatc aacaccatgc tgcgcgtgta cctgccgaag     360

atcaccagca tgctgagcga cgtgattaag cagaactacg ccctgagcct gcagatcgag     420

tacctgagca agcagctgca ggagatcagc gacaagctgg acatcatcaa cgtgaacgtc     480

ctgatcaaca gcaccctgac cgagatcacc ccggcctacc agcgcatcaa gtacgtgaac     540

gagaagttcg aagagctgac cttcgccacc gagaccagca gcaaggtgaa gaaggacggc     600

agcccggccg acatcctgga cgagctgacc gagctgaccg agctggcgaa gagcgtgacc     660

aagaacgacg tggacggctt cgagttctac ctgaacacct tccacgacgt gatggtgggc     720

aacaacctgt tcggccgcag cgccctgaag accgccagcg agctgatcac caaggagaac     780

gtgaagacca gcggcagcga ggtgggcaac gtgtacaact tcctgatcgt gctgaccgcc     840

ctgcaggccc aggccttcct gaccctgacc acctgtcgca agctgctggg cctggccgac     900

atcgactaca ccagcatcat gaacgagcac ttgaacaagg agaaggagga gttccgcgtg     960

aacatcctgc cgaccctgag caacaccttc agcaacccga actacgccaa ggtgaagggc    1020

agcgacgagg acgccaagat gatcgtggag gctaagccgg gccacgcgtt gatcggcttc    1080

gagatcagca acgacagcat caccgtgctg aaggtgtacg aggccaagct gaagcagaac    1140

taccaggtgg acaaggacag cttgagcgag gtgatctacg gcgacatgga caagctgctg    1200
```

```
tgtccggacc agagcgagca aatctactac accaacaaca tcgtgttccc gaacgagtac   1260

gtgatcacca agatcgactt caccaagaag atgaagaccc tgcgctacga ggtgaccgcc   1320

aacttctacg acagcagcac cggcgagatc gacctgaaca agaagaaggt ggagagcagc   1380

gaggccgagt accgcaccct gagcgcgaac gacgacggcg tctacatgcc actgggcgtg   1440

atcagcgaga ccttcctgac cccgatcaac ggctttggcc tgcaggccga cgagaacagc   1500

cgcctgatca ccctgacctg taagagctac ctgcgcgagc tgctgctagc caccgacctg   1560

agcaacaagg agaccaagct gatcgtgcca ccgagcggct tcatcagcaa catcgtggag   1620

aacggcagca tcgaggagga caacctggag ccgtggaagg ccaacaacaa gaacgcctac   1680

gtcgaccaca ccggcggcgt gaacggcacc aaggccctgt acgtgcacaa ggacggcggc   1740

atcagccagt tcatcggcga caagctgaag ccgaagaccg agtacgtgat ccagtacacc   1800

gtgaagggca agccatcgat tcacctgaag gacgagaaca ccggctacat ccactacgag   1860

gacaccaaca acaacctgga ggactaccag accatcaaca agcgcttcac caccggcacc   1920

gacctgaagg gcgtgtacct gatcctgaag agccagaacg gcgacgaggc ctggggcgac   1980

aacttcatca tcctggagat cagcccgagc gagaagctgc tgagcccgga gctgatcaac   2040

accaacaact ggaccagcac cggcagcacc aacatcagcg gcaacaccct gaccctgtac   2100

cagggcggcc gcggcatcct gaagcagaac ctgcagctgg acagcttcag cacctaccgc   2160

gtgtacttca gcgtgagcgg cgacgccaac gtgcgcatcc gcaactcccg cgaggtgctg   2220

ttcgagaaga ggtacatgag cggcgccaag gacgtgagcg agatgttcac caccaagttc   2280

gagaaggaca acttctacat cgagctgagc cagggcaaca acctgtacgg cggcccgatc   2340

gtgcacttct acgacgtgag catcaagtag                                     2370
```

```
<210> SEQ ID NO 2
<211> LENGTH: 789
<212> TYPE: PRT
<213> ORGANISM: Artificial Sequence
<220> FEATURE:
<223> OTHER INFORMATION: Vip3Aa toxin
<220> FEATURE:
<221> NAME/KEY: MISC_FEATURE
<222> LOCATION: (1)..(789)
<223> OTHER INFORMATION: Vip3Aa20 protein produced by MIR162

<400> SEQUENCE: 2

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Ile Lys Gln Asn Tyr Ala Leu Ser Leu Gln Ile Glu Tyr Leu Ser Lys
```

```
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560
```

```
Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
    770                 775                 780

Asp Val Ser Ile Lys
785
```

<210> SEQ ID NO 3
<211> LENGTH: 14405
<212> TYPE: DNA
<213> ORGANISM: Artificial Sequence
<220> FEATURE:
<223> OTHER INFORMATION: Plasmid pNOV1300

<400> SEQUENCE: 3

```
atgaacaaga acaacaccaa gctgagcacc cgcgccctgc cgagcttcat cgactacttc      60

aacggcatct acggcttcgc caccggcatc aaggacatca tgaacatgat cttcaagacc     120

gacaccggcg gcgacctgac cctggacgag atcctgaaga accagcagct gctgaacgac     180

atcagcggca agctggacgg cgtgaacggc agcctgaacg acctgatcgc ccagggcaac     240

ctgaacaccg agctgagcaa ggagatcctt aagatcgcca acgagcagaa ccaggtgctg     300

aacgacgtga acaacaagct ggacgccatc aacaccatgc tgcgcgtgta cctgccgaag     360

atcaccagca tgctgagcga cgtgatgaag cagaactacg ccctgagcct gcagatcgag     420

tacctgagca agcagctgca ggagatcagc gacaagctgg acatcatcaa cgtgaacgtc     480

ctgatcaaca gcaccctgac cgagatcacc ccggcctacc agcgcatcaa gtacgtgaac     540

gagaagttcg aagagctgac cttcgccacc gagaccagca gcaaggtgaa gaaggacggc     600

agcccggccg acatcctgga cgagctgacc gagctgaccg agctggcgaa gagcgtgacc     660

aagaacgacg tggacggctt cgagttctac ctgaacacct tccacgacgt gatggtgggc     720

aacaacctgt tcggccgcag cgccctgaag accgccagcg agctgatcac caaggagaac     780
```

```
gtgaagacca gcggcagcga ggtgggcaac gtgtacaact tcctgatcgt gctgaccgcc    840
ctgcaggccc aggccttcct gaccctgacc acctgtcgca agctgctggg cctggccgac    900
atcgactaca ccagcatcat gaacgagcac ttgaacaagg agaaggagga gttccgcgtg    960
aacatcctgc cgaccctgag caacaccttc agcaacccga actacgccaa ggtgaagggc   1020
agcgacgagg acgccaagat gatcgtggag gctaagccgg gccacgcgtt gatcggcttc   1080
gagatcagca acgacagcat caccgtgctg aaggtgtacg aggccaagct gaagcagaac   1140
taccaggtgg acaaggacag cttgagcgag gtgatctacg gcgacatgga caagctgctg   1200
tgtccggacc agagcgagca aatctactac accaacaaca tcgtgttccc gaacgagtac   1260
gtgatcacca agatcgactt caccaagaag atgaagaccc tgcgctacga ggtgaccgcc   1320
aacttctacg acagcagcac cggcgagatc gacctgaaca agaagaaggt ggagagcagc   1380
gaggccgagt accgcaccct gagcgcgaac gacgacggcg tctacatgcc actgggcgtg   1440
atcagcgaga ccttcctgac cccgatcaac ggctttggcc tgcaggccga cgagaacagc   1500
cgcctgatca ccctgacctg taagagctac ctgcgcgagc tgctgctagc caccgacctg   1560
agcaacaagg agaccaagct gatcgtgcca ccgagcggct tcatcagcaa catcgtggag   1620
aacggcagca tcgaggagga caacctggag ccgtggaagg ccaacaacaa gaacgcctac   1680
gtggaccaca ccggcggcgt gaacggcacc aaggccctgt acgtgcacaa ggacggcggc   1740
atcagccagt tcatcggcga caagctgaag ccgaagaccg agtacgtgat ccagtacacc   1800
gtgaagggca agccatcgat tcacctgaag gacgagaaca ccggctacat ccactacgag   1860
gacaccaaca acaacctgga ggactaccag accatcaaca agcgcttcac caccggcacc   1920
gacctgaagg gcgtgtacct gatcctgaag agccagaacg gcgacgaggc ctggggcgac   1980
aacttcatca tcctggagat cagcccgagc gagaagctgc tgagcccgga gctgatcaac   2040
accaacaact ggaccagcac cggcagcacc aacatcagcg gcaacaccct gaccctgtac   2100
cagggcggcc gcggcatcct gaagcagaac ctgcagctgg acagcttcag cacctaccgc   2160
gtgtacttca gcgtgagcgg cgacgccaac gtgcgcatcc gcaactcccg cgaggtgctg   2220
ttcgagaaga ggtacatgag cggcgccaag gacgtgagcg agatgttcac caccaagttc   2280
gagaaggaca acttctacat cgagctgagc cagggcaaca acctgtacgg cggcccgatc   2340
gtgcacttct acgacgtgag catcaagtag gagctctaga tctgttctgc acaaagtgga   2400
gtagtcagtc atcgatcagg aaccagacac cagactttta ttcatacagt gaagtgaagt   2460
gaagtgcagt gcagtgagtt gctggttttt gtacaactta gtatgtattt gtatttgtaa   2520
aatacttcta tcaataaaat ttctaattcc taaaaccaaa atccaggggt accagcttgc   2580
atgcctgcag tgcagcgtga cccggtcgtg cccctctcta gagataatga gcattgcatg   2640
tctaagttat aaaaaattac cacatatttt ttttgtcaca cttgtttgaa gtgcagttta   2700
tctatcttta tacatatatt taaactttac tctacgaata atataatcta tagtactaca   2760
ataatatcag tgttttagag aatcatataa atgaacagtt agacatggtc taaaggacaa   2820
ttgagtattt tgacaacagg actctacagt tttatctttt tagtgtgcat gtgttctcct   2880
tttttttttgc aaatagcttc acctatataa tacttcatcc attttattag tacatccatt   2940
tagggtttag ggttaatggt ttttatagac taattttttt agtacatcta ttttattcta   3000
ttttagcctc taaattaaga aaactaaaac tctattttag tttttttatt taataattta   3060
gatataaaat agaataaaat aaagtgacta aaaattaaac aaataccctt taagaaatta   3120
aaaaaactaa ggaaacattt ttcttgtttc gagtagataa tgccagcctg ttaaacgccg   3180
```

```
tcgacgagtc taacggacac caaccagcga accagcagcg tcgcgtcggg ccaagcgaag   3240
cagacggcac ggcatctctg tcgctgcctc tggacccctc tcgagagttc cgctccaccg   3300
ttggacttgc tccgctgtcg gcatccagaa attgcgtggc ggagcggcag acgtgagccg   3360
gcacggcagg cggcctcctc ctcctctcac ggcaccggca gctacggggg attcctttcc   3420
caccgctcct tcgctttccc ttcctcgccc gccgtaataa atagacaccc cctccacacc   3480
ctctttcccc aacctcgtgt tgttcggagc gcacacacac acaaccagat ctcccccaaa   3540
tccacccgtc ggcacctccg cttcaaggta cgccgctcgt cctccccccc cccccctctc   3600
taccttctct agatcggcgt tccggtccat ggttagggcc cggtagttct acttctgttc   3660
atgtttgtgt tagatccgtg tttgtgttag atccgtgctg ctagcgttcg tacacggatg   3720
cgacctgtac gtcagacacg ttctgattgc taacttgcca gtgtttctct ttggggaatc   3780
ctgggatggc tctagccgtt ccgcagacgg gatcgatttc atgatttttt ttgtttcgtt   3840
gcatagggtt tggtttgccc ttttccttta tttcaatata tgccgtgcac ttgtttgtcg   3900
ggtcatcttt tcatgctttt ttttgtcttg gttgtgatga tgtggtctgg ttgggcggtc   3960
gttctagatc ggagtagaat tctgtttcaa actacctggt ggatttatta attttggatc   4020
tgtatgtgtg tgccatacat attcatagtt acgaattgaa gatgatggat ggaaatatcg   4080
atctaggata ggtatacatg ttgatgcggg ttttactgat gcatatacag agatgctttt   4140
tgttcgcttg gttgtgatga tgtggtgtgg ttgggcggtc gttcattcgt tctagatcgg   4200
agtagaatac tgtttcaaac tacctggtgt atttattaat tttggaactg tatgtgtgtg   4260
tcatacatct tcatagttac gagtttaaga tggatggaaa tatcgatcta ggataggtat   4320
acatgttgat gtgggtttta ctgatgcata tacatgatgg catatgcagc atctattcat   4380
atgctctaac cttgagtacc tatctattat aataaacaag tatgttttat aattattttg   4440
atcttgatat acttggatga tggcatatgc agcagctata tgtggatttt tttagccctg   4500
ccttcatacg ctatttattt gcttggtact gtttcttttg tcgatgctca ccctgttgtt   4560
tggtgttact tctgcaggga tccccgatca tgcaaaaact cattaactca gtgcaaaact   4620
atgcctgggg cagcaaaacg gcgttgactg aactttatgg tatggaaaat ccgtccagcc   4680
agccgatggc cgagctgtgg atgggcgcac atccgaaaag cagttcacga gtgcagaatg   4740
ccgccggaga tatcgtttca ctgcgtgatg tgattgagag tgataaatcg actctgctcg   4800
gagaggccgt tgccaaacgc tttggcgaac tgcctttcct gttcaaagta ttatgcgcag   4860
cacagccact ctccattcag gttcatccaa acaaacacaa ttctgaaatc ggttttgcca   4920
aagaaaatgc cgcaggtatc ccgatggatg ccgccgagcg taactataaa gatcctaacc   4980
acaagccgga gctggttttt gcgctgacgc ctttccttgc gatgaacgcg tttcgtgaat   5040
tttccgagat tgtctcccta ctccagccgg tcgcaggtgc acatccggcg attgctcact   5100
ttttacaaca gcctgatgcc gaacgtttaa gcgaactgtt cgccagcctg ttgaatatgc   5160
agggtgaaga aaaatcccgc gcgctggcga ttttaaaatc ggccctcgat agccagcagg   5220
gtgaaccgtg gcaaacgatt cgtttaattt ctgaatttta cccggaagac agcggtctgt   5280
tctccccgct attgctgaat gtggtgaaat tgaaccctgg cgaagcgatg ttcctgttcg   5340
ctgaaacacc gcacgcttac ctgcaaggcg tggcgctgga agtgatggca aactccgata   5400
acgtgctgcg tgcgggtctg acgcctaaat acattgatat tccggaactg gttgccaatg   5460
tgaaattcga agccaaaccg gctaaccagt tgttgaccca gccggtgaaa caaggtgcag   5520
aactggactt cccgattcca gtggatgatt ttgccttctc gctgcatgac cttagtgata   5580
```

```
aagaaaccac cattagccag cagagtgccg ccattttgtt ctgcgtcgaa ggcgatgcaa   5640
cgttgtggaa aggttctcag cagttacagc ttaaaccggg tgaatcagcg tttattgccg   5700
ccaacgaatc accggtgact gtcaaaggcc acggccgttt agcgcgtgtt tacaacaagc   5760
tgtaagagct tactgaaaaa attaacatct cttgctaagc tgggagctcg atccgtcgac   5820
ctgcagatcg ttcaaacatt tggcaataaa gtttcttaag attgaatcct gttgccggtc   5880
ttgcgatgat tatcatataa tttctgttga attacgttaa gcatgtaata attaacatgt   5940
aatgcatgac gttatttatg agatgggttt ttatgattag agtcccgcaa ttatacattt   6000
aatacgcgat agaaaacaaa atatagcgcg caaactagga taaattatcg cgcgcggtgt   6060
catctatgtt actagatccc cgggtctaga caattcagta cattaaaaac gtccgcaatg   6120
tgttattaag ttgtctaagc gtcaatttgt ttacaccaca atatatcctg ccaccagcca   6180
gccaacagct ccccgaccgg cagctcggca caaaatcacc actcgataca ggcagcccat   6240
cagtccggga cggcgtcagc gggagagccg ttgtaaggcg gcagactttg ctcatgttac   6300
cgatgctatt cggaagaacg gcaactaagc tgccgggttt gaaacacgga tgatctcgcg   6360
gagggtagca tgttgattgt aacgatgaca gagcgttgct gcctgtgatc aaatatcatc   6420
tccctcgcag agatccgaat tatcagcctt cttattcatt tctcgcttaa ccgtgacagg   6480
ctgtcgatct tgagaactat gccgacataa taggaaatcg ctggataaag ccgctgagga   6540
agctgagtgg cgctatttct ttagaagtga acgttgacga tcgtcgaccg taccccgatg   6600
aattaattcg gacgtacgtt ctgaacacag ctggatactt acttgggcga ttgtcataca   6660
tgacatcaac aatgtacccg tttgtgtaac cgtctcttgg aggttcgtat gacactagtg   6720
gttcccctca gcttgcgact agatgttgag gcctaacatt ttattagaga gcaggctagt   6780
tgcttagata catgatcttc aggccgttat ctgtcagggc aagcgaaaat tggccattta   6840
tgacgaccaa tgccccgcag aagctcccat ctttgccgcc atagacgccg cgcccccctt   6900
ttggggtgta gaacatcctt ttgccagatg tggaaaagaa gttcgttgtc ccattgttgg   6960
caatgacgta gtagccggcg aaagtgcgag acccatttgc gctatatata agcctacgat   7020
ttccgttgcg actattgtcg taattggatg aactattatc gtagttgctc tcagagttgt   7080
cgtaatttga tggactattg tcgtaattgc ttatggagtt gtcgtagttg cttggagaaa   7140
tgtcgtagtt ggatggggag tagtcatagg gaagacgagc ttcatccact aaaacaattg   7200
gcaggtcagc aagtgcctgc cccgatgcca tcgcaagtac gaggcttaga accaccttca   7260
acagatcgcg catagtcttc cccagctctc taacgcttga gttaagccgc gccgcgaagc   7320
ggcgtcggct tgaacgaatt gttagacatt atttgccgac taccttggtg atctcgcctt   7380
tcacgtagtg aacaaattct tccaactgat ctgcgcgcga ggccaagcga tcttcttgtc   7440
caagataagc ctgcctagct tcaagtatga cgggctgata ctgggccggc aggcgctcca   7500
ttgcccagtc ggcagcgaca tccttcggcg cgattttgcc ggttactgcg ctgtaccaaa   7560
tgcgggacaa cgtaagcact acatttcgct catcgccagc ccagtcgggc ggcgagttcc   7620
atagcgttaa ggtttcattt agcgcctcaa atagatcctg ttcaggaacc ggatcaaaga   7680
gttcctccgc cgctggacct accaaggcaa cgctatgttc tcttgctttt gtcagcaaga   7740
tagccagatc aatgtcgatc gtggctggct cgaagatacc tgcaagaatg tcattgcgct   7800
gccattctcc aaattgcagt tcgcgcttag ctggataacg ccacggaatg atgtcgtcgt   7860
gcacaacaat ggtgacttct acagcgcgga gaatctcgct ctctccaggg gaagccgaag   7920
tttccaaaag gtcgttgatc aaagctcgcc gcgttgtttc atcaagcctt acggtcaccg   7980
```

```
taaccagcaa atcaatatca ctgtgtggct tcaggccgcc atccactgcg gagccgtaca   8040
aatgtacggc cagcaacgtc ggttcgagat ggcgctcgat gacgccaact acctctgata   8100
gttgagtcga tacttcggcg atcaccgctt ccctcatgat gtttaactcc tgaattaagc   8160
cgcgccgcga agcggtgtcg gcttgaatga attgttaggc gtcatcctgt gctcccgaga   8220
accagtacca gtacatcgct gtttcgttcg agacttgagg tctagtttta tacgtgaaca   8280
ggtcaatgcc gccgagagta aagccacatt ttgcgtacaa attgcaggca ggtacattgt   8340
tcgtttgtgt ctctaatcgt atgccaagga gctgtctgct tagtgcccac tttttcgcaa   8400
attcgatgag actgtgcgcg actcctttgc ctcggtgcgt gtgcgacaca acaatgtgtt   8460
cgatagaggc tagatcgttc catgttgagt tgagttcaat cttcccgaca agctcttggt   8520
cgatgaatgc gccatagcaa gcagagtctt catcagagtc atcatccgag atgtaatcct   8580
tccggtaggg gctcacactt ctggtagata gttcaaagcc ttggtcggat aggtgcacat   8640
cgaacacttc acgaacaatg aaatggttct cagcatccaa tgtttccgcc acctgctcag   8700
ggatcaccga aatcttcata tgacgcctaa cgcctggcac agcggatcgc aaacctggcg   8760
cggcttttgg cacaaaaggc gtgacaggtt tgcgaatccg ttgctgccac ttgttaaccc   8820
ttttgccaga tttggtaact ataatttatg ttagaggcga agtcttgggt aaaaactggc   8880
ctaaaattgc tggggatttc aggaaagtaa acatcacctt ccggctcgat gtctattgta   8940
gatatatgta gtgtatctac ttgatcgggg gatctgctgc ctcgcgcgtt tcggtgatga   9000
cggtgaaaac ctctgacaca tgcagctccc ggagacggtc acagcttgtc tgtaagcgga   9060
tgccgggagc agacaagccc gtcagggcgc gtcagcgggt gttggcgggt gtcggggcgc   9120
agccatgacc cagtcacgta gcgatagcgg agtgtatact ggcttaacta tgcggcatca   9180
gagcagattg tactgagagt gcaccatatg cggtgtgaaa taccgcacag atgcgtaagg   9240
agaaaatacc gcatcaggcg ctcttccgct tcctcgctca ctgactcgct gcgctcggtc   9300
gttcggctgc ggcgagcggt atcagctcac tcaaaggcgg taatacggtt atccacagaa   9360
tcaggggata acgcaggaaa gaacatgtga gcaaaaggcc agcaaaaggc caggaaccgt   9420
aaaaaggccg cgttgctggc gtttttccat aggctccgcc cccctgacga gcatcacaaa   9480
aatcgacgct caagtcagag gtggcgaaac ccgacaggac tataaagata ccaggcgttt   9540
ccccctggaa gctccctcgt gcgctctcct gttccgaccc tgccgcttac cggatacctg   9600
tccgcctttc tcccttcggg aagcgtggcg ctttctcata gctcacgctg taggtatctc   9660
agttcggtgt aggtcgttcg ctccaagctg ggctgtgtgc acgaaccccc cgttcagccc   9720
gaccgctgcg ccttatccgg taactatcgt cttgagtcca acccggtaag acacgactta   9780
tcgccactgg cagcagccac tggtaacagg attagcagag cgaggtatgt aggcggtgct   9840
acagagttct tgaagtggtg gcctaactac ggctacacta gaaggacagt atttggtatc   9900
tgcgctctgc tgaagccagt taccttcgga aaaagagttg gtagctcttg atccggcaaa   9960
caaaccaccg ctggtagcgg tggttttttt gtttgcaagc agcagattac gcgcagaaaa  10020
aaaggatctc aagaagatcc tttgatcttt tctacggggt ctgacgctca gtggaacgaa  10080
aactcacgtt aagggatttt ggtcatgaga ttatcaaaaa ggatcttcac ctagatcctt  10140
ttaaattaaa aatgaagttt taaatcaatc taaagtatat atgagtaaac ttggtctgac  10200
agttaccaat gcttaatcag tgaggcacct atctcagcga tctgtctatt tcgttcatcc  10260
atagttgcct gactccccgt cgtgtagata actacgatac gggagggctt accatctggc  10320
cccagtgctg caatgatacc gcgagaccca cgctcaccgg ctccagattt atcagcaata  10380
```

```
aaccagccag ccggaagggc cgagcgcaga agtggtcctg caactttatc cgcctccatc  10440
cagtctatta attgttgccg ggaagctaga gtaagtagtt cgccagttaa tagtttgcgc  10500
aacgttgttg ccattgctgc aggggggggg gggggggggt tccattgttc attccacgga  10560
caaaaacaga gaaaggaaac gacagaggcc aaaaagctcg ctttcagcac ctgtcgtttc  10620
ctttcttttc agagggtatt ttaaataaaa acattaagtt atgacgaaga agaacggaaa  10680
cgccttaaac cggaaaattt tcataaatag cgaaaacccg cgaggtcgcc gccccgtaac  10740
ctgtcggatc accggaaagg acccgtaaag tgataatgat tatcatctac atatcacaac  10800
gtgcgtggag gccatcaaac cacgtcaaat aatcaattat gacgcaggta tcgtattaat  10860
tgatctgcat caacttaacg taaaaacaac ttcagacaat acaaatcagc gacactgaat  10920
acggggcaac ctcatgtccc cccccccccc cccccctgcag gcatcgtggt gtcacgctcg  10980
tcgtttggta tggcttcatt cagctccggt tcccaacgat caaggcgagt tacatgatcc  11040
cccatgttgt gcaaaaaagc ggttagctcc ttcggtcctc cgatcgttgt cagaagtaag  11100
ttggccgcag tgttatcact catggttatg gcagcactgc ataattctct tactgtcatg  11160
ccatccgtaa gatgcttttc tgtgactggt gagtactcaa ccaagtcatt ctgagaatag  11220
tgtatgcggc gaccgagttg ctcttgcccg gcgtcaacac gggataatac cgcgccacat  11280
agcagaactt taaaagtgct catcattgga aaacgttctt cggggcgaaa actctcaagg  11340
atcttaccgc tgttgagatc cagttcgatg taacccactc gtgcacccaa ctgatcttca  11400
gcatctttta ctttcaccag cgtttctggg tgagcaaaaa caggaaggca aaatgccgca  11460
aaaaagggaa taagggcgac acggaaatgt tgaatactca tactcttcct ttttcaatat  11520
tattgaagca tttatcaggg ttattgtctc atgagcggat acatatttga atgtatttag  11580
aaaaataaac aaataggggt tccgcgcaca tttccccgaa aagtgccacc tgacgtctaa  11640
gaaaccatta ttatcatgac attaacctat aaaaataggc gtatcacgag gccctttcgt  11700
cttcaagaat tggtcgacga tcttgctgcg ttcggatatt ttcgtggagt tcccgccaca  11760
gacccggatt gaaggcgaga tccagcaact cgcgccagat catcctgtga cggaactttg  11820
gcgcgtgatg actggccagg acgtcggccg aaagagcgac aagcagatca cgcttttcga  11880
cagcgtcgga tttgcgatcg aggatttttc ggcgctgcgc tacgtccgcg accgcgttga  11940
gggatcaagc cacagcagcc cactcgacct tctagccgac ccagacgagc caagggatct  12000
ttttggaatg ctgctccgtc gtcaggcttt ccgacgtttg ggtggttgaa cagaagtcat  12060
tatcgcacgg aatgccaagc actcccgagg ggaaccctgt ggttggcatg cacatacaaa  12120
tggacgaacg gataaacctt ttcacgccct tttaaatatc cgattattct aataaacgct  12180
cttttctctt aggtttaccc gccaatatat cctgtcaaac actgatagtt taaactgaag  12240
gcgggaaacg acaatctgat catgagcgga gaattaaggg agtcacgtta tgacccccgc  12300
cgatgacgcg ggacaagccg ttttacgttt ggaactgaca gaaccgcaac gttgaaggag  12360
ccactcagca agctggtaca agcttgcatg cctgcagtgc agcgtgaccc ggtcgtgccc  12420
ctctctagag ataatgagca ttgcatgtct aagttataaa aaattaccac atattttttt  12480
tgtcacactt gtttgaagtg cagtttatct atctttatac atatatttaa actttactct  12540
acgaataata taatctatag tactacaata atatcagtgt tttagagaat catataaatg  12600
aacagttaga catggtctaa aggacaattg agtattttga caacaggact ctacagtttt  12660
atctttttag tgtgcatgtg ttctcctttt tttttgcaaa tagcttcacc tatataatac  12720
ttcatccatt ttattagtac atccatttag ggtttagggt taatggtttt tatagactaa  12780
```

```
tttttttagt acatctattt tattctattt tagcctctaa attaagaaaa ctaaaactct  12840

attttagttt ttttatttaa taatttagat ataaaataga ataaaataaa gtgactaaaa  12900

attaaacaaa taccctttaa gaaattaaaa aaactaagga aacatttttc ttgtttcgag  12960

tagataatgc cagcctgtta aacgccgtcg acgagtctaa cggacaccaa ccagcgaacc  13020

agcagcgtcg cgtcgggcca agcgaagcag acggcacggc atctctgtcg ctgcctctgg  13080

acccctctcg agagttccgc tccaccgttg gacttgctcc gctgtcggca tccagaaatt  13140

gcgtggcgga gcggcagacg tgagccggca cggcaggcgg cctcctcctc ctctcacggc  13200

accggcagct acgggggatt cctttcccac cgctccttcg ctttcccttc ctcgcccgcc  13260

gtaataaata gacacccct ccacaccctc tttccccaac ctcgtgttgt tcggagcgca  13320

cacacacaca accagatctc ccccaaatcc acccgtcggc acctccgctt caaggtacgc  13380

cgctcgtcct cccccccccc ccctctctac cttctctaga tcggcgttcc ggtccatggt  13440

tagggcccgg tagttctact tctgttcatg tttgtgttag atccgtgttt gtgttagatc  13500

cgtgctgcta gcgttcgtac acggatgcga cctgtacgtc agacacgttc tgattgctaa  13560

cttgccagtg tttctctttg gggaatcctg ggatggctct agccgttccg cagacgggat  13620

cgatttcatg attttttttg tttcgttgca tagggtttgg tttgcccttt tcctttattt  13680

caatatatgc cgtgcacttg tttgtcgggt catcttttca tgcttttttt tgtcttggtt  13740

gtgatgatgt ggtctggttg ggcggtcgtt ctagatcgga gtagaattct gtttcaaact  13800

acctggtgga tttattaatt ttggatctgt atgtgtgtgc catacatatt catagttacg  13860

aattgaagat gatggatgga aatatcgatc taggataggt atacatgttg atgcgggttt  13920

tactgatgca tatacagaga tgctttttgt tcgcttggtt gtgatgatgt ggtgtggttg  13980

ggcggtcgtt cattcgttct agatcggagt agaatactgt ttcaaactac ctggtgtatt  14040

tattaatttt ggaactgtat gtgtgtgtca tacatcttca tagttacgag tttaagatgg  14100

atggaaatat cgatctagga taggtataca tgttgatgtg ggttttactg atgcatatac  14160

atgatggcat atgcagcatc tattcatatg ctctaacctt gagtacctat ctattataat  14220

aaacaagtat gttttataat tattttgatc ttgatatact tggatgatgg catatgcagc  14280

agctatatgt ggattttttt agccctgcct tcatacgcta tttatttgct tggtactgtt  14340

tctttttgtcg atgctcaccc tgttgtttgg tgttacttct gcaggtcgac tctagaggat  14400

ccacc                                                              14405
```

<210> SEQ ID NO 4
<211> LENGTH: 21
<212> TYPE: DNA
<213> ORGANISM: Artificial Sequence
<220> FEATURE:
<223> OTHER INFORMATION: Chemically synthesized - vip3Aa TAQMAN primer

<400> SEQUENCE: 4

```
caccttcagc aacccgaact a                                                21
```

<210> SEQ ID NO 5
<211> LENGTH: 22
<212> TYPE: DNA
<213> ORGANISM: Artificial Sequence
<220> FEATURE:
<223> OTHER INFORMATION: Chemmicall synthesized - vip3Aa TAQMAN primer rev

<400> SEQUENCE: 5
gcttagcctc cacgatcatc tt 22

<210> SEQ ID NO 6
<211> LENGTH: 23
<212> TYPE: DNA
<213> ORGANISM: Artificial Sequence
<220> FEATURE:
<223> OTHER INFORMATION: Chemically synthesized - vip3Aa TAQMAN probe

<400> SEQUENCE: 6
gtcctcgtcg ctgcccttca cct 23

<210> SEQ ID NO 7
<211> LENGTH: 18
<212> TYPE: DNA
<213> ORGANISM: Artificial Sequence
<220> FEATURE:
<223> OTHER INFORMATION: Chemically synthesized - pmi TAQMAN primer for

<400> SEQUENCE: 7
ccgggtgaat cagcgttt 18

<210> SEQ ID NO 8
<211> LENGTH: 18
<212> TYPE: DNA
<213> ORGANISM: Artificial Sequence
<220> FEATURE:
<223> OTHER INFORMATION: Chemically synthesized - pmi TAQMAN primer rev

<400> SEQUENCE: 8
gccgtggcct ttgacagt 18

<210> SEQ ID NO 9
<211> LENGTH: 20
<212> TYPE: DNA
<213> ORGANISM: Artificial Sequence
<220> FEATURE:
<223> OTHER INFORMATION: Chemically synthesized - pmi TAQMAN probe

<400> SEQUENCE: 9
tgccgccaac gaatcaccgg 20

<210> SEQ ID NO 10
<211> LENGTH: 21
<212> TYPE: DNA
<213> ORGANISM: Artificial Sequence
<220> FEATURE:
<223> OTHER INFORMATION: Chemically synthesized - ZmADH-267 TAQMAN
      primer for

<400> SEQUENCE: 10
gaacgtgtgt tgggtttgca t 21

<210> SEQ ID NO 11
<211> LENGTH: 20
<212> TYPE: DNA
<213> ORGANISM: Artificial Sequence
<220> FEATURE:
<223> OTHER INFORMATION: Chemically synthesized - ZmADH-267 TAQMAN
      primer rev

<400> SEQUENCE: 11
tccagcaatc cttgcacctt 20

<210> SEQ ID NO 12
<211> LENGTH: 24
<212> TYPE: DNA

<213> ORGANISM: Artificial Sequence
<220> FEATURE:
<223> OTHER INFORMATION: Chemically synthesized -ZmADH-267 TAQMAN probe

<400> SEQUENCE: 12
tgcagcctaa ccatgcgcag ggta 24

<210> SEQ ID NO 13
<211> LENGTH: 2370
<212> TYPE: DNA
<213> ORGANISM: Artificial Sequence
<220> FEATURE:
<223> OTHER INFORMATION: Chemically synthesized - vip3Aa20 probe

<400> SEQUENCE: 13
atgaacaaga acaacaccaa gctgagcacc cgcgccctgc cgagcttcat cgactacttc 60
aacggcatct acggcttcgc caccggcatc aaggacatca tgaacatgat cttcaagacc 120
gacaccggcg gcgacctgac cctggacgag atcctgaaga accagcagct gctgaacgac 180
atcagcggca agctggacgg cgtgaacggc agcctgaacg acctgatcgc ccagggcaac 240
ctgaacaccg agctgagcaa ggagatcctt aagatcgcca acgagcagaa ccaggtgctg 300
aacgacgtga acaacaagct ggacgccatc aacaccatgc tgcgcgtgta cctgccgaag 360
atcaccagca tgctgagcga cgtgatgaag cagaactacg ccctgagcct gcagatcgag 420
tacctgagca agcagctgca ggagatcagc gacaagctgg acatcatcaa cgtgaacgtc 480
ctgatcaaca gcaccctgac cgagatcacc ccggcctacc agcgcatcaa gtacgtgaac 540
gagaagttcg aagagctgac cttcgccacc gagaccagca gcaaggtgaa gaaggacggc 600
agcccggccg acatcctgga cgagctgacc gagctgaccg agctggcgaa gagcgtgacc 660
aagaacgacg tggacggctt cgagttctac ctgaacacct tccacgacgt gatggtgggc 720
aacaacctgt tcggccgcag cgccctgaag accgccagcg agctgatcac caaggagaac 780
gtgaagacca gcggcagcga ggtgggcaac gtgtacaact tcctgatcgt gctgaccgcc 840
ctgcaggccc aggccttcct gaccctgacc acctgtcgca agctgctggg cctggccgac 900
atcgactaca ccagcatcat gaacgagcac ttgaacaagg agaaggagga gttccgcgtg 960
aacatcctgc cgaccctgag caacaccttc agcaacccga actacgccaa ggtgaagggc 1020
agcgacgagg acgccaagat gatcgtggag gctaagccgg gccacgcgtt gatcggcttc 1080
gagatcagca acgacagcat caccgtgctg aaggtgtacg aggccaagct gaagcagaac 1140
taccaggtgg acaaggacag cttgagcgag gtgatctacg gcgacatgga caagctgctg 1200
tgtccggacc agagcgagca aatctactac accaacaaca tcgtgttccc gaacgagtac 1260
gtgatcacca agatcgactt caccaagaag atgaagaccc tgcgctacga ggtgaccgcc 1320
aacttctacg acagcagcac cggcgagatc gacctgaaca agaagaaggt ggagagcagc 1380
gaggccgagt accgcaccct gagcgcgaac gacgacggcg tctacatgcc actgggcgtg 1440
atcagcgaga ccttcctgac cccgatcaac ggctttggcc tgcaggccga cgagaacagc 1500
cgcctgatca ccctgacctg taagagctac ctgcgcgagc tgctgctagc caccgacctg 1560
agcaacaagg agaccaagct gatcgtgcca ccgagcggct tcatcagcaa catcgtggag 1620
aacggcagca tcgaggagga caacctggag ccgtggaagg ccaacaacaa gaacgcctac 1680
gtggaccaca ccggcggcgt gaacggcacc aaggccctgt acgtgcacaa ggacggcggc 1740
atcagccagt tcatcggcga caagctgaag ccgaagaccg agtacgtgat ccagtacacc 1800
gtgaagggca agccatcgat tcacctgaag gacgagaaca ccggctacat ccactacgag 1860
gacaccaaca acaacctgga ggactaccag accatcaaca agcgcttcac caccggcacc 1920
gacctgaagg gcgtgtacct gatcctgaag agccagaacg gcgacgaggc ctggggcgac 1980
aacttcatca tcctggagat cagcccgagc gagaagctgc tgagcccgga gctgatcaac 2040
accaacaact ggaccagcac cggcagcacc aacatcagcg gcaacaccct gaccctgtac 2100
cagggcggcc gcggcatcct gaagcagaac ctgcagctgg acagcttcag cacctaccgc 2160
gtgtacttca gcgtgagcgg cgacgccaac gtgcgcatcc gcaactcccg cgaggtgctg 2220
ttcgagaaga ggtacatgag cggcgccaag gacgtgagcg agatgttcac caccaagttc 2280
gagaaggaca acttctacat cgagctgagc cagggcaaca acctgtacgg cggcccgatc 2340
gtgcacttct acgacgtgag catcaagtag 2370

<210> SEQ ID NO 14
<211> LENGTH: 1176
<212> TYPE: DNA
<213> ORGANISM: Artificial Sequence
<220> FEATURE:
<223> OTHER INFORMATION: Chemically synthesized - pmi probe

<400> SEQUENCE: 14
atgcaaaaac tcattaactc agtgcaaaac tatgcctggg gcagcaaaac ggcgttgact 60
gaactttatg gtatggaaaa tccgtccagc cagccgatgg ccgagctgtg gatgggcgca 120
catccgaaaa gcagttcacg agtgcagaat gccgccggag atatcgtttc actgcgtgat 180
gtgattgaga gtgataaatc gactctgctc ggagaggccg ttgccaaacg ctttggcgaa 240
ctgcctttcc tgttcaaagt attatgcgca gcacagccac tctccattca ggttcatcca 300
aacaaacaca attctgaaat cggttttgcc aaagaaaatg ccgcaggtat cccgatggat 360
gccgccgagc gtaactataa agatcctaac cacaagccgg agctggtttt tgcgctgacg 420
cctttccttg cgatgaacgc gtttcgtgaa ttttccgaga ttgtctccct actccagccg 480
gtcgcaggtg cacatccggc gattgctcac tttttacaac agcctgatgc cgaacgttta 540
agcgaactgt tcgccagcct gttgaatatg cagggtgaag aaaaatcccg cgcgctggcg 600
attttaaaat cggccctcga tagccagcag ggtgaaccgt ggcaaacgat tcgtttaatt 660
tctgaatttt acccggaaga cagcggtctg ttctccccgc tattgctgaa tgtggtgaaa 720
ttgaaccctg gcgaagcgat gttcctgttc gctgaaacac cgcacgctta cctgcaaggc 780
gtggcgctgg aagtgatggc aaactccgat aacgtgctgc gtgcgggtct gacgcctaaa 840
tacattgata ttccggaact ggttgccaat gtgaaattcg aagccaaacc ggctaaccag 900
ttgttgaccc agccggtgaa acaaggtgca gaactggact tcccgattcc agtggatgat 960
tttgccttct cgctgcatga ccttagtgat aaagaaacca ccattagcca gcagagtgcc 1020
gccattttgt tctgcgtcga aggcgatgca acgttgtgga aaggttctca gcagttacag 1080
cttaaaccgg gtgaatcagc gtttattgcc gccaacgaat caccggtgac tgtcaaaggc 1140
cacggccgtt tagcgcgtgt ttacaacaag ctgtaa 1176

<210> SEQ ID NO 15
<211> LENGTH: 20
<212> TYPE: DNA
<213> ORGANISM: Artificial Sequence
<220> FEATURE:
<223> OTHER INFORMATION: Chemically synthesized - MOV3Aa-01-5' primer

<400> SEQUENCE: 15
atgaacaaga acaacaccaa 20

<210> SEQ ID NO 16
<211> LENGTH: 22
<212> TYPE: DNA
<213> ORGANISM: Artificial Sequence
<220> FEATURE:
<223> OTHER INFORMATION: Chemically synthesized - MOV3Aa-01-3' primer

<400> SEQUENCE: 16
ctacttgatg ctcacgtcgt ag 22

<210> SEQ ID NO 17
<211> LENGTH: 18
<212> TYPE: DNA
<213> ORGANISM: Artificial Sequence
<220> FEATURE:
<223> OTHER INFORMATION: Chemically synthesized

<400> SEQUENCE: 17
acgagcagaa ccaggtgc 18

<210> SEQ ID NO 18
<211> LENGTH: 18
<212> TYPE: DNA
<213> ORGANISM: Artificial Sequence
<220> FEATURE:
<223> OTHER INFORMATION: Chemically synthesized

<400> SEQUENCE: 18
ggtgaagaag gacggcag 18

<210> SEQ ID NO 19
<211> LENGTH: 20
<212> TYPE: DNA
<213> ORGANISM: Artificial Sequence
<220> FEATURE:
<223> OTHER INFORMATION: Chemically synthesized

<400> SEQUENCE: 19
acctgtcgca agctgctggg 20

<210> SEQ ID NO 20
<211> LENGTH: 18
<212> TYPE: DNA
<213> ORGANISM: Artificial Sequence
<220> FEATURE:
<223> OTHER INFORMATION: Chemically synthesized

<400> SEQUENCE: 20
tggacaagct gctgtgtc 18

<210> SEQ ID NO 21
<211> LENGTH: 19
<212> TYPE: DNA
<213> ORGANISM: Artificial Sequence
<220> FEATURE:
<223> OTHER INFORMATION: Chemically synthesized

<400> SEQUENCE: 21
tgcaggccga cgagaacag 19

<210> SEQ ID NO 22
<211> LENGTH: 19
<212> TYPE: DNA
<213> ORGANISM: Artificial Sequence
<220> FEATURE:
<223> OTHER INFORMATION: Chemically synthesized

<400> SEQUENCE: 22
tgatccagta caccgtgaa 19

<210> SEQ ID NO 23
<211> LENGTH: 18
<212> TYPE: DNA
<213> ORGANISM: Artificial Sequence
<220> FEATURE:
<223> OTHER INFORMATION: Chemically synthesized

<400> SEQUENCE: 23
accctgaccc tgtaccag 18

<210> SEQ ID NO 24
<211> LENGTH: 18
<212> TYPE: DNA
<213> ORGANISM: Artificial Sequence
<220> FEATURE:
<223> OTHER INFORMATION: Chemically synthesized

<400> SEQUENCE: 24
gtgttgccgc tgatgttg 18

<210> SEQ ID NO 25
<211> LENGTH: 18
<212> TYPE: DNA
<213> ORGANISM: Artificial Sequence
<220> FEATURE:
<223> OTHER INFORMATION: Chemically synthesized

<400> SEQUENCE: 25
cgtactcggt cttcggct 18

<210> SEQ ID NO 26
<211> LENGTH: 18
<212> TYPE: DNA
<213> ORGANISM: Artificial Sequence
<220> FEATURE:
<223> OTHER INFORMATION: Chemically synthesized

<400> SEQUENCE: 26
ctgcaggcca aagccgtt 18

<210> SEQ ID NO 27
<211> LENGTH: 18
<212> TYPE: DNA
<213> ORGANISM: Artificial Sequence
<220> FEATURE:
<223> OTHER INFORMATION: Chemically synthesized

<400> SEQUENCE: 27
tcgccgtaga tcacctcg 18

<210> SEQ ID NO 28
<211> LENGTH: 18
<212> TYPE: DNA
<213> ORGANISM: Artificial Sequence
<220> FEATURE:
<223> OTHER INFORMATION: Chemcially synthesized

<400> SEQUENCE: 28
gcttgcgaca ggtggtca 18

<210> SEQ ID NO 29
<211> LENGTH: 19
<212> TYPE: DNA

<213> ORGANISM: Artificial Sequence
<220> FEATURE:
<223> OTHER INFORMATION: Chemically synthesized

<400> SEQUENCE: 29
ttgctgctgg tctcggtgg 19

<210> SEQ ID NO 30
<211> LENGTH: 19
<212> TYPE: DNA
<213> ORGANISM: Artificial Sequence
<220> FEATURE:
<223> OTHER INFORMATION: Chemically synthesized

<400> SEQUENCE: 30
cgttggcgat cttaaggat 19

<210> SEQ ID NO 31
<211> LENGTH: 17
<212> TYPE: DNA
<213> ORGANISM: Artificial Sequence
<220> FEATURE:
<223> OTHER INFORMATION: Chemically synthesized

<400> SEQUENCE: 31
gcaagccatc gattcac 17

<210> SEQ ID NO 32
<211> LENGTH: 17
<212> TYPE: DNA
<213> ORGANISM: Artificial Sequence
<220> FEATURE:
<223> OTHER INFORMATION: Chemically synthesized

<400> SEQUENCE: 32
gcaacaccct gaccctg 17

<210> SEQ ID NO 33
<211> LENGTH: 20
<212> TYPE: DNA
<213> ORGANISM: Artificial Sequence
<220> FEATURE:
<223> OTHER INFORMATION: Chemically synthesized

<400> SEQUENCE: 33
tctacgacgt gagcatcaag 20

<210> SEQ ID NO 34
<211> LENGTH: 19
<212> TYPE: DNA
<213> ORGANISM: Artificial Sequence
<220> FEATURE:
<223> OTHER INFORMATION: Chemically synthesized

<400> SEQUENCE: 34
gtagaagtgc acgatcggg 19

<210> SEQ ID NO 35
<211> LENGTH: 17
<212> TYPE: DNA
<213> ORGANISM: Artificial Sequence
<220> FEATURE:
<223> OTHER INFORMATION: Chemcially synthesized

<400> SEQUENCE: 35
cggtgctggt ccagttg 17

<210> SEQ ID NO 36
<211> LENGTH: 21
<212> TYPE: DNA
<213> ORGANISM: Artificial Sequence
<220> FEATURE:
<223> OTHER INFORMATION: Chemcially synthesized - 162INSERT-F2 primer

<400> SEQUENCE: 36
acaccaatga tgcaaatagg c 21

<210> SEQ ID NO 37
<211> LENGTH: 25
<212> TYPE: DNA
<213> ORGANISM: Artificial Sequence
<220> FEATURE:
<223> OTHER INFORMATION: Chemically synthesized - VIP_R4 primer

<400> SEQUENCE: 37
gaaggtgttc aggtagaact cgaag 25

<210> SEQ ID NO 38
<211> LENGTH: 2946
<212> TYPE: DNA
<213> ORGANISM: Artificial Sequence
<220> FEATURE:
<223> OTHER INFORMATION: Chemcially synthesized - vip3Aa20 5' amplicon

<400> SEQUENCE: 38
acaccaatga tgcaaatagg ctgggaatag tctgtctaat agtttgagtg aatcatgtca 60
ctgatagttt aaactgaagg cgggaaacga caatctgatc atgagcggag aattaaggga 120
gtcacgttat gacccccgcc gatgacgcgg gacaagccgt tttacgtttg gaactgacag 180
aaccgcaacg ttgaaggagc cactcagcaa gctggtacaa gcttgcatgc ctgcagtgca 240
gcgtgacccg gtcgtgcccc tctctagaga taatgagcat tgcatgtcta agttataaaa 300
aattaccaca tatttttttt gtcacacttg tttgaagtgc agtttatcta tctttataca 360
tatatttaaa ctttactcta cgaataatat aatctatagt actacaataa tatcagtgtt 420
ttagagaatc atataaatga acagttagac atggtctaaa ggacaattga gtattttgac 480
aacaggactc tacagtttta tctttttagt gtgcatgtgt tctccttttt ttttgcaaat 540
agcttcacct atataatact tcatccattt tattagtaca tccatttagg gtttagggtt 600
aatggttttt atagactaat ttttttagta catctatttt attctatttt agcctctaaa 660
ttaagaaaac taaaactcta ttttagtttt tttatttaat aatttagata taaaatagaa 720
taaaataaag tgactaaaaa ttaaacaaat accctttaag aaattaaaaa aactaaggaa 780
acatttttct tgtttcgagt agataatgcc agcctgttaa acgccgtcga cgagtctaac 840
ggacaccaac cagcgaacca gcagcgtcgc gtcgggccaa gcgaagcaga cggcacggca 900
tctctgtcgc tgcctctgga cccctctcga gagttccgct ccaccgttgg acttgctccg 960
ctgtcggcat ccagaaattg cgtggcggag cggcagacgt gagccggcac ggcaggcggc 1020
ctcctcctcc tctcacggca ccggcagcta cgggggattc ctttcccacc gctccttcgc 1080
tttcccttcc tcgcccgccg taataaatag acaccccctc cacaccctct ttccccaacc 1140
tcgtgttgtt cggagcgcac acacacacaa ccagatctcc cccaaatcca cccgtcggca 1200
cctccgcttc aaggtacgcc gctcgtcctc cccccccccc cctctctacc ttctctagat 1260
cggcgttccg gtccatggtt agggcccggt agttctactt ctgttcatgt ttgtgttaga 1320
tccgtgtttg tgttagatcc gtgctgctag cgttcgtaca cggatgcgac ctgtacgtca 1380

```
gacacgttct gattgctaac ttgccagtgt ttctctttgg ggaatcctgg gatggctcta   1440

gccgttccgc agacgggatc gatttcatga ttttttttgt ttcgttgcat agggtttggt   1500

ttgccctttt cctttatttc aatatatgcc gtgcacttgt ttgtcgggtc atcttttcat   1560

gctttttttt gtcttggttg tgatgatgtg gtctggttgg gcggtcgttc tagatcggag   1620

tagaattctg tttcaaacta cctggtggat ttattaattt tggatctgta tgtgtgtgcc   1680

atacatattc atagttacga attgaagatg atggatggaa atatcgatct aggataggta   1740

tacatgttga tgcgggtttt actgatgcat atacagagat gctttttgtt cgcttggttg   1800

tgatgatgtg gtgtggttgg gcggtcgttc attcgttcta gatcggagta gaatactgtt   1860

tcaaactacc tggtgtattt attaattttg gaactgtatg tgtgtgtcat acatcttcat   1920

agttacgagt ttaagatgga tggaaatatc gatctaggat aggtatacat gttgatgtgg   1980

gttttactga tgcatataca tgatggcata tgcagcatct attcatatgc tctaaccttg   2040

agtacctatc tattataata aacaagtatg ttttataatt attttgatct tgatatactt   2100

ggatgatggc atatgcagca gctatatgtg gattttttta gccctgcctt catacgctat   2160

ttatttgctt ggtactgttt cttttgtcga tgctcaccct gttgtttggt gttacttctg   2220

caggtcgact ctagaggatc caccatgaac aagaacaaca ccaagctgag cacccgcgcc   2280

ctgccgagct tcatcgacta cttcaacggc atctacggct tcgccaccgg catcaaggac   2340

atcatgaaca tgatcttcaa gaccgacacc ggcggcgacc tgaccctgga cgagatcctg   2400

aagaaccagc agctgctgaa cgacatcagc ggcaagctgg acggcgtgaa cggcagcctg   2460

aacgacctga tcgcccaggg caacctgaac accgagctga gcaaggagat ccttaagatc   2520

gccaacgagc agaaccaggt gctgaacgac gtgaacaaca agctggacgc catcaacacc   2580

atgctgcgcg tgtacctgcc gaagatcacc agcatgctga gcgacgtgat taagcagaac   2640

tacgccctga gcctgcagat cgagtacctg agcaagcagc tgcaggagat cagcgacaag   2700

ctggacatca tcaacgtgaa cgtcctgatc aacagcaccc tgaccgagat caccccggcc   2760

taccagcgca tcaagtacgt gaacgagaag ttcgaagagc tgaccttcgc caccgagacc   2820

agcagcaagg tgaagaagga cggcagcccg gccgacatcc tggacgagct gaccgagctg   2880

accgagctgg cgaagagcgt gaccaagaac gacgtggacg gcttcgagtt ctacctgaac   2940

accttc                                                              2946
```

```
<210> SEQ ID NO 39
<211> LENGTH: 23
<212> TYPE: DNA
<213> ORGANISM: Artificial Sequence
<220> FEATURE:
<223> OTHER INFORMATION: Chemically synthesized - CJB179 Primer

<400> SEQUENCE: 39

atgcaaatag gctgggaata gtc                                             23


<210> SEQ ID NO 40
<211> LENGTH: 21
<212> TYPE: DNA
<213> ORGANISM: Artificial Sequence
<220> FEATURE:
<223> OTHER INFORMATION: Chemically synthesized - CTRB3116 Reverse
      Primer

<400> SEQUENCE: 40

gtaccagctt gctgagtggc t                                               21
```

```
<210> SEQ ID NO 41
<211> LENGTH: 209
<212> TYPE: DNA
<213> ORGANISM: Artificial Sequence
<220> FEATURE:
<223> OTHER INFORMATION: Chemically synthesized - CJB134/179 5'
      amplicon

<400> SEQUENCE: 41

atgcaaatag gctgggaata gtctgtctaa tagtttgagt gaatcatgtc actgatagtt     60

taaactgaag gcgggaaacg acaatctgat catgagcgga gaattaaggg agtcacgtta    120

tgacccccgc cgatgacgcg ggacaagccg ttttacgttt ggaactgaca gaaccgcaac    180

gttgaaggag ccactcagca agctggtac                                      209


<210> SEQ ID NO 42
<211> LENGTH: 20
<212> TYPE: DNA
<213> ORGANISM: Artificial Sequence
<220> FEATURE:
<223> OTHER INFORMATION: Chemcially synthesized - VIP-F3 primer

<400> SEQUENCE: 42

ggtgctgttc gagaagaggt                                                 20


<210> SEQ ID NO 43
<211> LENGTH: 23
<212> TYPE: DNA
<213> ORGANISM: Artificial Sequence
<220> FEATURE:
<223> OTHER INFORMATION: Chemically synthesized - PMI_REV1 primer

<400> SEQUENCE: 43

cgatttatca ctctcaatca cat                                             23


<210> SEQ ID NO 44
<211> LENGTH: 2577
<212> TYPE: DNA
<213> ORGANISM: Artificial Sequence
<220> FEATURE:
<223> OTHER INFORMATION: Chemcially synthesized - vip3Aa20 3' amplicon

<400> SEQUENCE: 44

ggtgctgttc gagaagaggt acatgagcgg cgccaaggac gtgagcgaga tgttcaccac     60

caagttcgag aaggacaact tctacatcga gctgagccag ggcaacaacc tgtacggcgg    120

cccgatcgtg cacttctacg acgtgagcat caagtaggag ctctagatct gttctgcaca    180

aagtggagta gtcagtcatc gatcaggaac cagacaccag acttttattc atacagtgaa    240

gtgaagtgaa gtgcagtgca gtgagttgct ggtttttgta caacttagta tgtatttgta    300

tttgtaaaat acttctatca ataaaatttc taattcctaa aaccaaaatc caggggtacc    360

agcttgcatg cctgcagtgc agcgtgaccc ggtcgtgccc ctctctagag ataatgagca    420

ttgcatgtct aagttataaa aaattaccac atattttttt tgtcacactt gtttgaagtg    480

cagtttatct atctttatac atatatttaa actttactct acgaataata taatctatag    540

tactacaata atatcagtgt tttagagaat catataaatg aacagttaga catggtctaa    600

aggacaattg agtattttga caacaggact ctacagtttt atctttttag tgtgcatgtg    660

ttctcctttt tttttgcaaa tagcttcacc tatataatac ttcatccatt ttattagtac    720

atccatttag ggtttagggt taatggtttt tatagactaa tttttttagt acatctattt    780

tattctattt tagcctctaa attaagaaaa ctaaaactct attttagttt ttttatttaa    840
```

```
taatttagat ataaaataga ataaaataaa gtgactaaaa attaaacaaa taccctttaa    900

gaaattaaaa aaactaagga aacatttttc ttgtttcgag tagataatgc cagcctgtta    960

aacgccgtcg acgagtctaa cggacaccaa ccagcgaacc agcagcgtcg cgtcgggcca   1020

agcgaagcag acggcacggc atctctgtcg ctgcctctgg acccctctcg agagttccgc   1080

tccaccgttg gacttgctcc gctgtcggca tccagaaatt gcgtggcgga gcggcagacg   1140

tgagccggca cggcaggcgg cctcctcctc ctctcacggc accggcagct acgggggatt   1200

cctttcccac cgctccttcg ctttcccttc ctcgcccgcc gtaataaata gacacccct    1260

ccacaccctc tttccccaac ctcgtgttgt tcggagcgca cacacacaca accagatctc   1320

ccccaaatcc acccgtcggc acctccgctt caaggtacgc cgctcgtcct cccccccccc   1380

ccctctctac cttctctaga tcggcgttcc ggtccatggt tagggcccgg tagttctact   1440

tctgttcatg tttgtgttag atccgtgttt gtgttagatc cgtgctgcta gcgttcgtac   1500

acggatgcga cctgtacgtc agacacgttc tgattgctaa cttgccagtg tttctctttg   1560

gggaatcctg ggatggctct agccgttccg cagacgggat cgatttcatg attttttttg   1620

tttcgttgca tagggtttgg tttgcccttt tcctttattt caatatatgc cgtgcacttg   1680

tttgtcgggt catcttttca tgcttttttt tgtcttggtt gtgatgatgt ggtctggttg   1740

ggcggtcgtt ctagatcgga gtagaattct gtttcaaact acctggtgga tttattaatt   1800

ttggatctgt atgtgtgtgc catacatatt catagttacg aattgaagat gatggatgga   1860

aatatcgatc taggataggt atacatgttg atgcgggttt tactgatgca tatacagaga   1920

tgctttttgt tcgcttggtt gtgatgatgt ggtgtggttg ggcggtcgtt cattcgttct   1980

agatcggagt agaatactgt ttcaaactac ctggtgtatt tattaatttt ggaactgtat   2040

gtgtgtgtca tacatcttca tagttacgag tttaagatgg atggaaatat cgatctagga   2100

taggtataca tgttgatgtg ggttttactg atgcatatac atgatggcat atgcagcatc   2160

tattcatatg ctctaacctt gagtacctat ctattataat aaacaagtat gttttataat   2220

tattttgatc ttgatatact tggatgatgg catatgcagc agctatatgt ggattttttt   2280

agccctgcct tcatacgcta tttatttgct tggtactgtt tcttttgtcg atgctcaccc   2340

tgttgtttgg tgttacttct gcagggatcc ccgatcatgc aaaaactcat taactcagtg   2400

caaaactatg cctggggcag caaaacggcg ttgactgaac tttatggtat ggaaaatccg   2460

tccagccagc cgatggccga gctgtggatg ggcgcacatc cgaaaagcag ttcacgagtg   2520

cagaatgccg ccggagatat cgtttcactg cgtgatgtga ttgagagtga taaatcg      2577
```

<210> SEQ ID NO 45
<211> LENGTH: 20
<212> TYPE: DNA
<213> ORGANISM: Artificial Sequence
<220> FEATURE:
<223> OTHER INFORMATION: 5' junction sequence between corn genome and insert DNA

<400> SEQUENCE: 45

```
tgaatcatgt cactgatagt                                                  20
```

<210> SEQ ID NO 46
<211> LENGTH: 1088
<212> TYPE: DNA
<213> ORGANISM: Artificial Sequence
<220> FEATURE:
<223> OTHER INFORMATION: 5' flanking sequence
<220> FEATURE:
<221> NAME/KEY: misc_feature
<222> LOCATION: (1)..(236)
<223> OTHER INFORMATION: 5' flanking sequence

<400> SEQUENCE: 46

```
tcctgtgttg ttggaacaga cttctgtctc ttctggtgat cataaatatt taaatgaacc     60

agttgtgttg gaaaatgttg ttttcttttg tctctagact ggaaagcgga gttctcgtca    120

acacggttct ttcaactagg gatgaaagtg gtaatccgaa ttgttagtac aaatttaata    180

ttttaaaata gatatgtata aaattttatg ttgatctttt ttatgttatc aagcacatta    240

gtataaatta gtataaatat gaataaaata ttacataaaa tgttttatgt attatttggt    300

ccctacaaca taaatagttg aaaaaattac taaatttgtt ttcgaatcta tatcgaagtt    360

tatatctatt atttaagaaa aatataggat gaaaaggttt atcttttatg aatctttaca    420

agctggatct tataaacaag aaaataaatt tatattgtag attttatatc ctatttattc    480

gcaatcaaag aaaagcgact aaaaaactga ttaccgagta aatactgttt ccaaccgttt    540

tcgtccctac tatcaacgcc ttctcccaac cgcagtcgat ctgtccgtct gtatcaggcg    600

cagcggcacc cctgctgttc gactatctag accatagaat attttaggta tacaataatt    660

ttagttccac gctagaacat tttagttaga ataataacaa gatttgctat tgatgtagga    720

ctcgcccgtc actgtctaaa aaagcattct gtcggtctta ttctttaggc atcagcgggt    780

gtactatctc atttttccta tcatattcct cagtactctg ttaagtataa atggtctatt    840

ttacatgatg aactaataaa actaattaag gatcctaact ttttgtgaag gtaatttgga    900

tcattatgca ttaccatcct acgtatacct gctgcagcag catctgcgta agcacagcct    960

agatatatgc ttctgtgtgg actgaaagga gactttgttt atcaattagt atactcccaa   1020

aaaactgatg acaccaatga tgcaaatagg ctgggaatag tctgtctaat agtttgagtg   1080

aatcatgt                                                            1088
```

<210> SEQ ID NO 47
<211> LENGTH: 20
<212> TYPE: DNA
<213> ORGANISM: Artificial Sequence
<220> FEATURE:
<223> OTHER INFORMATION: 3' junction sequence between insert DNA and corn genome

<400> SEQUENCE: 47

```
aaacgtccgc catggtctga                                                 20
```

<210> SEQ ID NO 48
<211> LENGTH: 1189
<212> TYPE: DNA
<213> ORGANISM: Artificial Sequence
<220> FEATURE:
<223> OTHER INFORMATION: 3' flanking sequence

<400> SEQUENCE: 48

```
catggtctga aggcaacaga taaggcatac tgggccttgt ggtagttgtt ttactgggcc     60

tttttgtatg atctataaaa ttcactggga tcaacccgga gaggaatggc agcagatgca    120

gtccccaggg tcctccgtcg ccgcctgagc acccggcacc cgcgctgaac cggagaggga    180

cgcgcggacg ccgtgcagct ggtgcggagg gggctgtggc agatgaggat gagacgcgta    240

cgtggctggg aaggccagca ggccaccggg tcttcgtcca gcccggcgcg agtggacagg    300

actagagatg gcaacggtta caaacccgct gggttttacc gtcccaaacc cgtacccgtg    360

aaaaatatct atgcccatta aaaaacccgt acccatgacg ggtttgagat tttgcccaaa    420
```

```
cccgtaccca tcgggttaac gggtacccat gggttacccg cgggtttcat ctccaatata    480

cctgttcttc tcataatcaa taagtatcgt aatgattaat gatatcatga tccaaaatct    540

atgtaatgaa caacgagttc atgatttggt ataaaaatta ttagtagaga gaatgaaata    600

caaataataa gttgtataat taagtgacct tgcactaagt tatccatcca tcacatatat    660

aacgctagta aaaactataa tatcaagcaa gcaacactct caccgactac tgatacattc    720

accaattgat aaaaaatatg aagtaaataa ggaataacaa gtttgttgtt cgtttataaa    780

ataaaatgac aatatgcact aggtttggtc gggtttaaaa aacccacggg ttcacgggtt    840

tgggtactat aggaacaaac ccgtacccat aaacccattg ggtacagatt tatgcccgtt    900

aacaaaccca tgggtatgaa aattgaccca aacctatacc ctaatggggt aaaaacccat    960

cgggtttcgg atttcgggta cccattgcca tctctagaca ggacaacctc ggccggtcct   1020

gtatgtaggc caccagcatc ggccagttgg tacatccagc cggggtcagg tcacttttac   1080

tcgtctcaat cagacaatca ccgtccacca acgaacgcca acgttgtcac ttgtcaggtc   1140

ggttgagact tgtatttttt tttgtcctcc gtaaaaatcg gttcaccag                1189


<210> SEQ ID NO 49
<211> LENGTH: 10579
<212> TYPE: DNA
<213> ORGANISM: Artificial Sequence
<220> FEATURE:
<223> OTHER INFORMATION: Vip3Aa20 Event MIR162 insert and flanking
      sequences
<220> FEATURE:
<221> NAME/KEY: misc_feature
<222> LOCATION: (1)..(1088)
<223> OTHER INFORMATION: 5' flanking sequence of event MIR162

<400> SEQUENCE: 49

tcctgtgttg ttggaacaga cttctgtctc ttctggtgat cataaatatt taaatgaacc     60

agttgtgttg gaaaatgttg ttttcttttg tctctagact ggaaagcgga gttctcgtca    120

acacggttct ttcaactagg gatgaaagtg gtaatccgaa ttgttagtac aaatttaata    180

ttttaaaata gatatgtata aaattttatg ttgatctttt ttatgttatc aagcacatta    240

gtataaatta gtataaatat gaataaaata ttacataaaa tgttttatgt attatttggt    300

ccctacaaca taaatagttg aaaaaattac taaatttgtt ttcgaatcta tatcgaagtt    360

tatatctatt atttaagaaa aatataggat gaaaaggttt atcttttatg aatctttaca    420

agctggatct tataaacaag aaaataaatt tatattgtag attttatatc ctatttattc    480

gcaatcaaag aaaagcgact aaaaaactga ttaccgagta aatactgttt ccaaccgttt    540

tcgtccctac tatcaacgcc ttctcccaac cgcagtcgat ctgtccgtct gtatcaggcg    600

cagcggcacc cctgctgttc gactatctag accatagaat attttaggta tacaataatt    660

ttagttccac gctagaacat tttagttaga ataataacaa gatttgctat tgatgtagga    720

ctcgcccgtc actgtctaaa aaagcattct gtcggtctta ttctttaggc atcagcgggt    780

gtactatctc atttttccta tcatattcct cagtactctg ttaagtataa atggtctatt    840

ttacatgatg aactaataaa actaattaag gatcctaact ttttgtgaag gtaatttgga    900

tcattatgca ttaccatcct acgtatacct gctgcagcag catctgcgta agcacagcct    960

agatatatgc ttctgtgtgg actgaaagga gactttgttt atcaattagt atactcccaa   1020

aaaactgatg acaccaatga tgcaaatagg ctgggaatag tctgtctaat agtttgagtg   1080

aatcatgtca ctgatagttt aaactgaagg cgggaaacga caatctgatc atgagcggag   1140

aattaaggga gtcacgttat gaccccccgcc gatgacgcgg gacaagccgt tttacgtttg   1200
```

-continued gaactgacag aaccgcaacg ttgaaggagc cactcagcaa gctggtacaa gcttgcatgc 1260
ctgcagtgca gcgtgacccg gtcgtgcccc tctctagaga taatgagcat tgcatgtcta 1320
agttataaaa aattaccaca tatttttttt gtcacacttg tttgaagtgc agtttatcta 1380
tctttataca tatatttaaa ctttactcta cgaataatat aatctatagt actacaataa 1440
tatcagtgtt ttagagaatc atataaatga acagttagac atggtctaaa ggacaattga 1500
gtattttgac aacaggactc tacagtttta tctttttagt gtgcatgtgt tctccttttt 1560
ttttgcaaat agcttcacct atataatact tcatccattt tattagtaca tccatttagg 1620
gtttagggtt aatggttttt atagactaat ttttttagta catctatttt attctatttt 1680
agcctctaaa ttaagaaaac taaaactcta ttttagtttt tttatttaat aatttagata 1740
taaaatagaa taaaataaag tgactaaaaa ttaaacaaat accctttaag aaattaaaaa 1800
aactaaggaa acatttttct tgtttcgagt agataatgcc agcctgttaa acgccgtcga 1860
cgagtctaac ggacaccaac cagcgaacca gcagcgtcgc gtcgggccaa gcgaagcaga 1920
cggcacggca tctctgtcgc tgcctctgga cccctctcga gagttccgct ccaccgttgg 1980
acttgctccg ctgtcggcat ccagaaattg cgtggcggag cggcagacgt gagccggcac 2040
ggcaggcggc ctcctcctcc tctcacggca ccggcagcta cgggggattc ctttcccacc 2100
gctccttcgc tttcccttcc tcgcccgccg taataaatag acaccccctc cacaccctct 2160
ttccccaacc tcgtgttgtt cggagcgcac acacacacaa ccagatctcc cccaaatcca 2220
cccgtcggca cctccgcttc aaggtacgcc gctcgtcctc cccccccccc cctctctacc 2280
ttctctagat cggcgttccg gtccatggtt agggcccggt agttctactt ctgttcatgt 2340
ttgtgttaga tccgtgtttg tgttagatcc gtgctgctag cgttcgtaca cggatgcgac 2400
ctgtacgtca gacacgttct gattgctaac ttgccagtgt ttctctttgg ggaatcctgg 2460
gatggctcta gccgttccgc agacgggatc gatttcatga ttttttttgt ttcgttgcat 2520
agggtttggt ttgccctttt cctttatttc aatatatgcc gtgcacttgt ttgtcgggtc 2580
atcttttcat gctttttttt gtcttggttg tgatgatgtg gtctggttgg gcggtcgttc 2640
tagatcggag tagaattctg tttcaaacta cctggtggat ttattaattt tggatctgta 2700
tgtgtgtgcc atacatattc atagttacga attgaagatg atggatggaa atatcgatct 2760
aggataggta tacatgttga tgcgggtttt actgatgcat atacagagat gctttttgtt 2820
cgcttggttg tgatgatgtg gtgtggttgg gcggtcgttc attcgttcta gatcggagta 2880
gaatactgtt tcaaactacc tggtgtattt attaattttg gaactgtatg tgtgtgtcat 2940
acatcttcat agttacgagt ttaagatgga tggaaatatc gatctaggat aggtatacat 3000
gttgatgtgg gttttactga tgcatataca tgatggcata tgcagcatct attcatatgc 3060
tctaaccttg agtacctatc tattataata aacaagtatg ttttataatt attttgatct 3120
tgatatactt ggatgatggc atatgcagca gctatatgtg gattttttta gccctgcctt 3180
catacgctat ttatttgctt ggtactgttt cttttgtcga tgctcaccct gttgtttggt 3240
gttacttctg caggtcgact ctagaggatc caccatgaac aagaacaaca ccaagctgag 3300
cacccgcgcc ctgccgagct tcatcgacta cttcaacggc atctacggct tcgccaccgg 3360
catcaaggac atcatgaaca tgatcttcaa gaccgacacc ggcggcgacc tgaccctgga 3420
cgagatcctg aagaaccagc agctgctgaa cgacatcagc ggcaagctgg acggcgtgaa 3480
cggcagcctg aacgacctga tcgcccaggg caacctgaac accgagctga gcaaggagat 3540
ccttaagatc gccaacgagc agaaccaggt gctgaacgac gtgaacaaca agctggacgc 3600

```
catcaacacc atgctgcgcg tgtacctgcc gaagatcacc agcatgctga gcgacgtgat   3660
gaagcagaac tacgccctga gcctgcagat cgagtacctg agcaagcagc tgcaggagat   3720
cagcgacaag ctggacatca tcaacgtgaa cgtcctgatc aacagcaccc tgaccgagat   3780
caccccggcc taccagcgca tcaagtacgt gaacgagaag ttcgaagagc tgaccttcgc   3840
caccgagacc agcagcaagg tgaagaagga cggcagcccg gccgacatcc tggacgagct   3900
gaccgagctg accgagctgg cgaagagcgt gaccaagaac gacgtggacg gcttcgagtt   3960
ctacctgaac accttccacg acgtgatggt gggcaacaac ctgttcggcc gcagcgccct   4020
gaagaccgcc agcgagctga tcaccaagga gaacgtgaag accagcggca gcgaggtggg   4080
caacgtgtac aacttcctga tcgtgctgac cgccctgcag gcccaggcct tcctgaccct   4140
gaccacctgt cgcaagctgc tgggcctggc cgacatcgac tacaccagca tcatgaacga   4200
gcacttgaac aaggagaagg aggagttccg cgtgaacatc ctgccgaccc tgagcaacac   4260
cttcagcaac ccgaactacg ccaaggtgaa gggcagcgac gaggacgcca agatgatcgt   4320
ggaggctaag ccgggccacg cgttgatcgg cttcgagatc agcaacgaca gcatcaccgt   4380
gctgaaggtg tacgaggcca agctgaagca gaactaccag gtggacaagg acagcttgag   4440
cgaggtgatc tacggcgaca tggacaagct gctgtgtccg gaccagagcg agcaaatcta   4500
ctacaccaac aacatcgtgt tcccgaacga gtacgtgatc accaagatcg acttcaccaa   4560
gaagatgaag accctgcgct acgaggtgac cgccaacttc tacgacagca gcaccggcga   4620
gatcgacctg aacaagaaga aggtggagag cagcgaggcc gagtaccgca ccctgagcgc   4680
gaacgacgac ggcgtctaca tgccactggg cgtgatcagc gagaccttcc tgaccccgat   4740
caacggcttt ggcctgcagg ccgacgagaa cagccgcctg atcaccctga cctgtaagag   4800
ctacctgcgc gagctgctgc tagccaccga cctgagcaac aaggagacca agctgatcgt   4860
gccaccgagc ggcttcatca gcaacatcgt ggagaacggc agcatcgagg aggacaacct   4920
ggagccgtgg aaggccaaca acaagaacgc ctacgtggac cacaccggcg gcgtgaacgg   4980
caccaaggcc ctgtacgtgc acaaggacgg cggcatcagc cagttcatcg gcgacaagct   5040
gaagccgaag accgagtacg tgatccagta caccgtgaag ggcaagccat cgattcacct   5100
gaaggacgag aacaccggct acatccacta cgaggacacc aacaacaacc tggaggacta   5160
ccagaccatc aacaagcgct tcaccaccgg caccgacctg aagggcgtgt acctgatcct   5220
gaagagccag aacggcgacg aggcctgggg cgacaacttc atcatcctgg agatcagccc   5280
gagcgagaag ctgctgagcc cggagctgat caacaccaac aactggacca gcaccggcag   5340
caccaacatc agcggcaaca ccctgaccct gtaccagggc ggccgcggca tcctgaagca   5400
gaacctgcag ctggacagct tcagcaccta ccgcgtgtac ttcagcgtga gcggcgacgc   5460
caacgtgcgc atccgcaact cccgcgaggt gctgttcgag aagaggtaca tgagcggcgc   5520
caaggacgtg agcgagatgt tcaccaccaa gttcgagaag gacaacttct acatcgagct   5580
gagccagggc aacaacctgt acggcggccc gatcgtgcac ttctacgacg tgagcatcaa   5640
gtaggagctc tagatctgtt ctgcacaaag tggagtagtc agtcatcgat caggaaccag   5700
acaccagact tttattcata cagtgaagtg aagtgaagtg cagtgcagtg agttgctggt   5760
ttttgtacaa cttagtatgt atttgtattt gtaaaatact tctatcaata aaatttctaa   5820
ttcctaaaac caaaatccag ggtaccagc ttgcatgcct gcagtgcagc gtgacccggt   5880
cgtgcccctc tctagagata atgagcattg catgtctaag ttataaaaaa ttaccacata   5940
ttttttttgt cacacttgtt tgaagtgcag tttatctatc tttatacata tatttaaact   6000
```

ttactctacg aataatataa tctatagtac tacaataata tcagtgtttt agagaatcat 6060
ataaatgaac agttagacat ggtctaaagg acaattgagt attttgacaa caggactcta 6120
cagttttatc tttttagtgt gcatgtgttc tccttttttt ttgcaaatag cttcacctat 6180
ataatacttc atccatttta ttagtacatc catttagggt ttagggttaa tggtttttat 6240
agactaattt ttttagtaca tctattttat tctattttag cctctaaatt aagaaaacta 6300
aaactctatt ttagtttttt tatttaataa tttagatata aaatagaata aaataaagtg 6360
actaaaaatt aaacaaatac cctttaagaa attaaaaaaa ctaaggaaac atttttcttg 6420
tttcgagtag ataatgccag cctgttaaac gccgtcgacg agtctaacgg acaccaacca 6480
gcgaaccagc agcgtcgcgt cgggccaagc gaagcagacg gcacggcatc tctgtcgctg 6540
cctctggacc cctctcgaga gttccgctcc accgttggac ttgctccgct gtcggcatcc 6600
agaaattgcg tggcggagcg gcagacgtga gccggcacgg caggcggcct cctcctcctc 6660
tcacggcacc ggcagctacg gggggattcct ttcccaccgc tccttcgctt tcccttcctc 6720
gcccgccgta ataaatagac acccccctcca caccctcttt ccccaacctc gtgttgttcg 6780
gagcgcacac acacacaacc agatctcccc caaatccacc cgtcggcacc tccgcttcaa 6840
ggtacgccgc tcgtcctccc cccccccccc tctctacctt ctctagatcg gcgttccggt 6900
ccatggttag ggcccggtag ttctacttct gttcatgttt gtgttagatc cgtgtttgtg 6960
ttagatccgt gctgctagcg ttcgtacacg gatgcgacct gtacgtcaga cacgttctga 7020
ttgctaactt gccagtgttt ctctttgggg aatcctggga tggctctagc cgttccgcag 7080
acgggatcga tttcatgatt ttttttgttt cgttgcatag ggtttggttt gccctttttcc 7140
tttatttcaa tatatgccgt gcacttgttt gtcgggtcat cttttcatgc ttttttttgt 7200
cttggttgtg atgatgtggt ctggttgggc ggtcgttcta gatcggagta gaattctgtt 7260
tcaaactacc tggtggattt attaattttg gatctgtatg tgtgtgccat acatattcat 7320
agttacgaat tgaagatgat ggatggaaat atcgatctag gataggtata catgttgatg 7380
cgggttttac tgatgcatat acagagatgc tttttgttcg cttggttgtg atgatgtggt 7440
gtggttgggc ggtcgttcat tcgttctaga tcggagtaga atactgtttc aaactacctg 7500
gtgtatttat taattttgga actgtatgtg tgtgtcatac atcttcatag ttacgagttt 7560
aagatggatg gaaatatcga tctaggatag gtatacatgt tgatgtgggt tttactgatg 7620
catatacatg atggcatatg cagcatctat tcatatgctc taaccttgag tacctatcta 7680
ttataataaa caagtatgtt ttataattat tttgatcttg atatacttgg atgatggcat 7740
atgcagcagc tatatgtgga tttttttagc cctgccttca tacgctattt atttgcttgg 7800
tactgtttct tttgtcgatg ctcaccctgt tgtttggtgt tacttctgca gggatccccg 7860
atcatgcaaa aactcattaa ctcagtgcaa aactatgcct ggggcagcaa aacggcgttg 7920
actgaacttt atggtatgga aaatccgtcc agccagccga tggccgagct gtggatgggc 7980
gcacatccga aaagcagttc acgagtgcag aatgccgccg gagatatcgt ttcactgcgt 8040
gatgtgattg agagtgataa atcgactctg ctcggagagg ccgttgccaa acgctttggc 8100
gaactgcctt tcctgttcaa agtattatgc gcagcacagc cactctccat tcaggttcat 8160
ccaaacaaac acaattctga aatcggtttt gccaaagaaa atgccgcagg tatcccgatg 8220
gatgccgccg agcgtaacta taaagatcct aaccacaagc cggagctggt tttgcgctg 8280
acgcctttcc ttgcgatgaa cgcgtttcgt gaattttccg agattgtctc cctactccag 8340
ccggtcgcag gtgcacatcc ggcgattgct cactttttac aacagcctga tgccgaacgt 8400

```
ttaagcgaac tgttcgccag cctgttgaat atgcagggtg aagaaaaatc ccgcgcgctg   8460
gcgattttaa aatcggccct cgatagccag cagggtgaac cgtggcaaac gattcgttta   8520
atttctgaat tttacccgga agacagcggt ctgttctccc cgctattgct gaatgtggtg   8580
aaattgaacc ctggcgaagc gatgttcctg ttcgctgaaa caccgcacgc ttacctgcaa   8640
ggcgtggcgc tggaagtgat ggcaaactcc gataacgtgc tgcgtgcggg tctgacgcct   8700
aaatacattg atattccgga actggttgcc aatgtgaaat tcgaagccaa accggctaac   8760
cagttgttga cccagccggt gaaacaaggt gcagaactgg acttcccgat tccagtggat   8820
gattttgcct tctcgctgca tgaccttagt gataaagaaa ccaccattag ccagcagagt   8880
gccgccattt tgttctgcgt cgaaggcgat gcaacgttgt ggaaaggttc tcagcagtta   8940
cagcttaaac cgggtgaatc agcgtttatt gccgccaacg aatcaccggt gactgtcaaa   9000
ggccacggcc gtttagcgcg tgtttacaac aagctgtaag agcttactga aaaaattaac   9060
atctcttgct aagctgggag ctcgatccgt cgacctgcag atcgttcaaa catttggcaa   9120
taaagtttct taagattgaa tcctgttgcc ggtcttgcga tgattatcat ataatttctg   9180
ttgaattacg ttaagcatgt aataattaac atgtaatgca tgacgttatt tatgagatgg   9240
gtttttatga ttagagtccc gcaattatac atttaatacg cgatagaaaa caaaatatag   9300
cgcgcaaact aggataaatt atcgcgcgcg gtgtcatcta tgttactaga tccccgggtc   9360
tagacaattc agtacattaa aaacgtccgc catggtctga aggcaacaga taaggcatac   9420
tgggccttgt ggtagttgtt ttactgggcc tttttgtatg atctataaaa ttcactggga   9480
tcaacccgga gaggaatggc agcagatgca gtccccaggg tcctccgtcg ccgcctgagc   9540
acccggcacc cgcgctgaac cggagaggga cgcgcggacg ccgtgcagct ggtgcggagg   9600
gggctgtggc agatgaggat gagacgcgta cgtggctggg aaggccagca ggccaccggg   9660
tcttcgtcca gcccggcgcg agtggacagg actagagatg gcaacggtta caaacccgct   9720
gggttttacc gtcccaaacc cgtacccgtg aaaaatatct atgcccatta aaaaacccgt   9780
acccatgacg ggtttgagat tttgcccaaa cccgtaccca tcgggttaac gggtacccat   9840
gggttacccg cgggtttcat ctccaatata cctgttcttc tcataatcaa taagtatcgt   9900
aatgattaat gatatcatga tccaaaatct atgtaatgaa caacgagttc atgatttggt   9960
ataaaaatta ttagtagaga gaatgaaata caaataataa gttgtataat taagtgacct  10020
tgcactaagt tatccatcca tcacatatat aacgctagta aaaactataa tatcaagcaa  10080
gcaacactct caccgactac tgatacattc accaattgat aaaaaatatg aagtaaataa  10140
ggaataacaa gtttgttgtt cgtttataaa ataaaatgac aatatgcact aggtttggtc  10200
gggtttaaaa aacccacggg ttcacgggtt tgggtactat aggaacaaac ccgtacccat  10260
aaacccattg ggtacagatt tatgcccgtt aacaaaccca tgggtatgaa aattgaccca  10320
aacctatacc ctaatggggt aaaaacccat cgggtttcgg atttcgggta cccattgcca  10380
tctctagaca ggacaacctc ggccggtcct gtatgtaggc caccagcatc ggccagttgg  10440
tacatccagc cggggtcagg tcacttttac tcgtctcaat cagacaatca ccgtccacca  10500
acgaacgcca acgttgtcac ttgtcaggtc ggttgagact tgtatttttt tttgtcctcc  10560
gtaaaaatcg gttcaccag                                                10579
```

<210> SEQ ID NO 50
<211> LENGTH: 23
<212> TYPE: DNA
<213> ORGANISM: Artificial Sequence
<220> FEATURE:
<223> OTHER INFORMATION: Chemically synthesized - FE1002 primer

<400> SEQUENCE: 50
cgtgactccc ttaattctcc gct 23

<210> SEQ ID NO 51
<211> LENGTH: 24
<212> TYPE: DNA
<213> ORGANISM: Artificial Sequence
<220> FEATURE:
<223> OTHER INFORMATION: Chemically synthesized - FE1003 primer

<400> SEQUENCE: 51
gatcagattg tcgtttcccg cctt 24

<210> SEQ ID NO 52
<211> LENGTH: 24
<212> TYPE: DNA
<213> ORGANISM: Artificial Sequence
<220> FEATURE:
<223> OTHER INFORMATION: Chemically synthesized - FE1004 primer

<400> SEQUENCE: 52
gattgtcgtt tcccgccttc agtt 24

<210> SEQ ID NO 53
<211> LENGTH: 27
<212> TYPE: DNA
<213> ORGANISM: Artificial Sequence
<220> FEATURE:
<223> OTHER INFORMATION: Chemically synthesized - 162_DW_Conf3 primer

<400> SEQUENCE: 53
cctgtgttgt tggaacagac ttctgtc 27

<210> SEQ ID NO 54
<211> LENGTH: 26
<212> TYPE: DNA
<213> ORGANISM: Artificial Sequence
<220> FEATURE:
<223> OTHER INFORMATION: Chemically synthesized - FE0900 primer

<400> SEQUENCE: 54
ggctccttca acgttgcggt tctgtc 26

<210> SEQ ID NO 55
<211> LENGTH: 1230
<212> TYPE: DNA
<213> ORGANISM: Artificial Sequence
<220> FEATURE:
<223> OTHER INFORMATION: Chemically synthesized - 5' PCR amplicon

<400> SEQUENCE: 55
cctgtgttgt tggaacagac ttctgtctct tctggtgatc ataaatattt aaatgaacca 60
gttgtgttgg aaaatgttgt tttcttttgt ctctagactg gaaagcggag ttctcgtcaa 120
cacggttctt tcaactaggg atgaaagtgg taatccgaat tgttagtaca aatttaatat 180
tttaaaatag atatgtataa aattttatgt tgatcttttt tatgttatca agcacattag 240
tataaattag tataaatatg aataaaatat tacataaaat gttttatgta ttatttggtc 300
cctacaacat aaatagttga aaaaattact aaatttgttt tcgaatctat atcgaagttt 360
atatctatta tttaagaaaa atataggatg aaaaggttta tcttttatga atctttacaa 420
gctggatctt ataaacaaga aaataaattt atattgtaga ttttatatcc tatttattcg 480

```
caatcaaaga aaagcgacta aaaaactgat taccgagtaa atactgtttc caaccgtttt    540

cgtccctact atcaacgcct tctcccaacc gcagtcgatc tgtccgtctg tatcaggcgc    600

agcggcaccc ctgctgttcg actatctaga ccatagaata ttttaggtat acaataattt    660

tagttccacg ctagaacatt ttagttagaa taataacaag atttgctatt gatgtaggac    720

tcgcccgtca ctgtctaaaa aagcattctg tcggtcttat tctttaggca tcagcgggtg    780

tactatctca tttttcctat catattcctc agtactctgt taagtataaa tggtctattt    840

tacatgatga actaataaaa ctaattaagg atcctaactt tttgtgaagg taatttggat    900

cattatgcat taccatccta cgtatacctg ctgcagcagc atctgcgtaa gcacagccta    960

gatatatgct tctgtgtgga ctgaaaggag actttgttta tcaattagta tactcccaaa   1020

aaactgatga caccaatgat gcaaataggc tgggaatagt ctgtctaata gtttgagtga   1080

atcatgtcac tgatagttta aactgaaggc gggaaacgac aatctgatca tgagcggaga   1140

attaagggag tcacgttatg acccccgccg atgacgcggg acaagccgtt ttacgtttgg   1200

aactgacaga accgcaacgt tgaaggagcc                                    1230
```

<210> SEQ ID NO 56
<211> LENGTH: 28
<212> TYPE: DNA
<213> ORGANISM: Artificial Sequence
<220> FEATURE:
<223> OTHER INFORMATION: Chemically synthesized - 162_GW_3_F1 primer

<400> SEQUENCE: 56

```
tctcttgcta agctgggagc tcgatccg                                        28
```

<210> SEQ ID NO 57
<211> LENGTH: 28
<212> TYPE: DNA
<213> ORGANISM: Artificial Sequence
<220> FEATURE:
<223> OTHER INFORMATION: Chemically synthesized - 162_GW_3_F2 primer

<400> SEQUENCE: 57

```
aagattgaat cctgttgccg gtcttgcg                                        28
```

<210> SEQ ID NO 58
<211> LENGTH: 24
<212> TYPE: DNA
<213> ORGANISM: Artificial Sequence
<220> FEATURE:
<223> OTHER INFORMATION: Chemically synthesized162_3'GW_R1 primer

<400> SEQUENCE: 58

```
ctggtgaacc gatttttacg gagg                                            24
```

<210> SEQ ID NO 59
<211> LENGTH: 1518
<212> TYPE: DNA
<213> ORGANISM: Artificial Sequence
<220> FEATURE:
<223> OTHER INFORMATION: Chemically synthesized - 3' PCR amplicon

<400> SEQUENCE: 59

```
tctcttgcta agctgggagc tcgatccgtc gacctgcaga tcgttcaaac atttggcaat     60

aaagtttctt aagattgaat cctgttgccg gtcttgcgat gattatcata taatttctgt    120

tgaattacgt taagcatgta ataattaaca tgtaatgcat gacgttattt atgagatggg    180

tttttatgat tagagtcccg caattataca tttaatacgc gatagaaaac aaaatatagc    240
```

```
gcgcaaacta ggataaatta tcgcgcgcgg tgtcatctat gttactagat ccccgggtct    300

agacaattca gtacattaaa aacgtccgcc atggtctgaa ggcaacagat aaggcatact    360

gggccttgtg gtagttgttt tactgggcct ttttgtatga tctataaaat tcactgggat    420

caacccggag aggaatggca gcagatgcag tccccagggt cctccgtcgc cgcctgagca    480

cccggcaccc gcgctgaacc ggagagggac gcgcggacgc cgtgcagctg gtgcggaggg    540

ggctgtggca gatgaggatg agacgcgtac gtggctggga aggccagcag gccaccgggt    600

cttcgtccag cccggcgcga gtggacagga ctagagatgg caacggttac aaacccgctg    660

ggttttaccg tcccaaaccc gtacccgtga aaaatatcta tgcccattaa aaaacccgta    720

cccatgacgg gtttgagatt ttgcccaaac ccgtacccat cgggttaacg ggtacccatg    780

ggttacccgc gggtttcatc tccaatatac ctgttcttct cataatcaat aagtatcgta    840

atgattaatg atatcatgat ccaaaatcta tgtaatgaac aacgagttca tgatttggta    900

taaaaattat tagtagagag aatgaaatac aaataataag ttgtataatt aagtgacctt    960

gcactaagtt atccatccat cacatatata acgctagtaa aaactataat atcaagcaag   1020

caacactctc accgactact gatacattca ccaattgata aaaaatatga agtaaataag   1080

gaataacaag tttgttgttc gtttataaaa taaaatgaca atatgcacta ggtttggtcg   1140

ggtttaaaaa acccacgggt tcacgggttt gggtactata ggaacaaacc cgtacccata   1200

aacccattgg gtacagattt atgcccgtta acaaacccat gggtatgaaa attgacccaa   1260

acctataccc taatggggta aaaacccatc gggtttcgga tttcgggtac ccattgccat   1320

ctctagacag gacaacctcg gccggtcctg tatgtaggcc accagcatcg gccagttggt   1380

acatccagcc ggggtcaggt cacttttact cgtctcaatc agacaatcac cgtccaccaa   1440

cgaacgccaa cgttgtcact tgtcaggtcg gttgagactt gtattttttt ttgtcctccg   1500

taaaaatcgg ttcaccag                                                 1518
```

<210> SEQ ID NO 60
<211> LENGTH: 20
<212> TYPE: DNA
<213> ORGANISM: Artificial Sequence
<220> FEATURE:
<223> OTHER INFORMATION: Chemically synthesized

<400> SEQUENCE: 60

```
ttcacgggag actttatctg                                                 20
```

<210> SEQ ID NO 61
<211> LENGTH: 17
<212> TYPE: DNA
<213> ORGANISM: Artificial Sequence
<220> FEATURE:
<223> OTHER INFORMATION: Chemically synthesized

<400> SEQUENCE: 61

```
ccgattcatt aatgcag                                                    17
```

<210> SEQ ID NO 62
<211> LENGTH: 17
<212> TYPE: DNA
<213> ORGANISM: Artificial Sequence
<220> FEATURE:
<223> OTHER INFORMATION: Chemically synthesized

<400> SEQUENCE: 62

```
acgtaaaacg gcttgtc                                                    17
```

<210> SEQ ID NO 63
<211> LENGTH: 17
<212> TYPE: DNA
<213> ORGANISM: Artificial Sequence
<220> FEATURE:
<223> OTHER INFORMATION: Chemically synthesized

<400> SEQUENCE: 63
gtttaaactg aaggcgg 17

<210> SEQ ID NO 64
<211> LENGTH: 22
<212> TYPE: DNA
<213> ORGANISM: Artificial Sequence
<220> FEATURE:
<223> OTHER INFORMATION: Chemically synthesized

<400> SEQUENCE: 64
aataatatca ctctgtacat cc 22

<210> SEQ ID NO 65
<211> LENGTH: 15
<212> TYPE: DNA
<213> ORGANISM: Artificial Sequence
<220> FEATURE:
<223> OTHER INFORMATION: Chemically synthesized

<400> SEQUENCE: 65
gttgtaaaac gacgg 15

<210> SEQ ID NO 66
<211> LENGTH: 18
<212> TYPE: DNA
<213> ORGANISM: Artificial Sequence
<220> FEATURE:
<223> OTHER INFORMATION: Chemically synthesized

<400> SEQUENCE: 66
taggcacccc aggcttta 18

<210> SEQ ID NO 67
<211> LENGTH: 18
<212> TYPE: DNA
<213> ORGANISM: Artificial Sequence
<220> FEATURE:
<223> OTHER INFORMATION: Chemically synthesized

<400> SEQUENCE: 67
aattgaattt agcggccg 18

<210> SEQ ID NO 68
<211> LENGTH: 20
<212> TYPE: DNA
<213> ORGANISM: Artificial Sequence
<220> FEATURE:
<223> OTHER INFORMATION: Chemically synthesized

<400> SEQUENCE: 68
ggtccctaca acataaatag 20

<210> SEQ ID NO 69
<211> LENGTH: 20
<212> TYPE: DNA
<213> ORGANISM: Artificial Sequence
<220> FEATURE:
<223> OTHER INFORMATION: Chemically synthesized

<400> SEQUENCE: 69
ttcgtcccta ctatcaacgc 20

<210> SEQ ID NO 70
<211> LENGTH: 18
<212> TYPE: DNA
<213> ORGANISM: Artificial Sequence
<220> FEATURE:
<223> OTHER INFORMATION: Chemically synthesized

<400> SEQUENCE: 70
ctttaggcat cagcgggt 18

<210> SEQ ID NO 71
<211> LENGTH: 18
<212> TYPE: DNA
<213> ORGANISM: Artificial Sequence
<220> FEATURE:
<223> OTHER INFORMATION: Chemically synthesized

<400> SEQUENCE: 71
agcatctgcg taagcaca 18

<210> SEQ ID NO 72
<211> LENGTH: 19
<212> TYPE: DNA
<213> ORGANISM: Artificial Sequence
<220> FEATURE:
<223> OTHER INFORMATION: Chemically synthesized

<400> SEQUENCE: 72
ctgatgacac caatgatgc 19

<210> SEQ ID NO 73
<211> LENGTH: 19
<212> TYPE: DNA
<213> ORGANISM: Artificial Sequence
<220> FEATURE:
<223> OTHER INFORMATION: Chemically synthesized

<400> SEQUENCE: 73
gatcagattg tcgtttccc 19

<210> SEQ ID NO 74
<211> LENGTH: 19
<212> TYPE: DNA
<213> ORGANISM: Artificial Sequence
<220> FEATURE:
<223> OTHER INFORMATION: Chemically synthesized

<400> SEQUENCE: 74
gcatcattgg tgtcatcag 19

<210> SEQ ID NO 75
<211> LENGTH: 18
<212> TYPE: DNA
<213> ORGANISM: Artificial Sequence
<220> FEATURE:
<223> OTHER INFORMATION: Chemically synthesized

<400> SEQUENCE: 75
tgtgcttacg cagatgct 18

<210> SEQ ID NO 76
<211> LENGTH: 18

<212> TYPE: DNA
<213> ORGANISM: Artificial Sequence
<220> FEATURE:
<223> OTHER INFORMATION: Chemically synthesized

<400> SEQUENCE: 76
acccgctgat gcctaaag 18

<210> SEQ ID NO 77
<211> LENGTH: 20
<212> TYPE: DNA
<213> ORGANISM: Artificial Sequence
<220> FEATURE:
<223> OTHER INFORMATION: Chemically synthesized

<400> SEQUENCE: 77
gcgttgatag tagggacgaa 20

<210> SEQ ID NO 78
<211> LENGTH: 20
<212> TYPE: DNA
<213> ORGANISM: Artificial Sequence
<220> FEATURE:
<223> OTHER INFORMATION: Chemically synthesized

<400> SEQUENCE: 78
ctatttatgt tgtagggacc 20

<210> SEQ ID NO 79
<211> LENGTH: 18
<212> TYPE: DNA
<213> ORGANISM: Artificial Sequence
<220> FEATURE:
<223> OTHER INFORMATION: Chemically synthesized

<400> SEQUENCE: 79
ctagactgga aagcggag 18

<210> SEQ ID NO 80
<211> LENGTH: 19
<212> TYPE: DNA
<213> ORGANISM: Artificial Sequence
<220> FEATURE:
<223> OTHER INFORMATION: Chemically synthesized

<400> SEQUENCE: 80
ccactttcat ccctagttg 19

<210> SEQ ID NO 81
<211> LENGTH: 17
<212> TYPE: DNA
<213> ORGANISM: Artificial Sequence
<220> FEATURE:
<223> OTHER INFORMATION: Chemically synthesized

<400> SEQUENCE: 81
gattgaatcc tgttgcc 17

<210> SEQ ID NO 82
<211> LENGTH: 20
<212> TYPE: DNA
<213> ORGANISM: Artificial Sequence
<220> FEATURE:
<223> OTHER INFORMATION: Chemically synthesized

<400> SEQUENCE: 82
tctcataaat aacgtcatgc 20

<210> SEQ ID NO 83
<211> LENGTH: 20
<212> TYPE: DNA
<213> ORGANISM: Artificial Sequence
<220> FEATURE:
<223> OTHER INFORMATION: Chemically synthesized

<400> SEQUENCE: 83
tctgtggata accgtattac 20

<210> SEQ ID NO 84
<211> LENGTH: 20
<212> TYPE: DNA
<213> ORGANISM: Artificial Sequence
<220> FEATURE:
<223> OTHER INFORMATION: Chemically synthesized

<400> SEQUENCE: 84
agtaacatag atgacaccgc 20

<210> SEQ ID NO 85
<211> LENGTH: 18
<212> TYPE: DNA
<213> ORGANISM: Artificial Sequence
<220> FEATURE:
<223> OTHER INFORMATION: Chemically synthesized

<400> SEQUENCE: 85
ccagtgtgct ggaattcg 18

<210> SEQ ID NO 86
<211> LENGTH: 20
<212> TYPE: DNA
<213> ORGANISM: Artificial Sequence
<220> FEATURE:
<223> OTHER INFORMATION: Chemically synthesized

<400> SEQUENCE: 86
ccagtgtgat ggatatctgc 20

<210> SEQ ID NO 87
<211> LENGTH: 18
<212> TYPE: DNA
<213> ORGANISM: Artificial Sequence
<220> FEATURE:
<223> OTHER INFORMATION: Chemically synthesized

<400> SEQUENCE: 87
ccagtgtgct ggaattcg 18

<210> SEQ ID NO 88
<211> LENGTH: 20
<212> TYPE: DNA
<213> ORGANISM: Artificial Sequence
<220> FEATURE:
<223> OTHER INFORMATION: Chemically synthesized

<400> SEQUENCE: 88
ccagtgtgat ggatatctgc 20

<210> SEQ ID NO 89
<211> LENGTH: 20
<212> TYPE: DNA
<213> ORGANISM: Artificial Sequence
<220> FEATURE:
<223> OTHER INFORMATION: Chemically synthesized

<400> SEQUENCE: 89
gtgtgctgga attcgccctt 20

<210> SEQ ID NO 90
<211> LENGTH: 20
<212> TYPE: DNA
<213> ORGANISM: Artificial Sequence
<220> FEATURE:
<223> OTHER INFORMATION: Chemically synthesized

<400> SEQUENCE: 90
tatctgcaga attcgccctt 20

<210> SEQ ID NO 91
<211> LENGTH: 20
<212> TYPE: DNA
<213> ORGANISM: Artificial Sequence
<220> FEATURE:
<223> OTHER INFORMATION: Chemically synthesized

<400> SEQUENCE: 91
gtgtgctgga attcgccctt 20

<210> SEQ ID NO 92
<211> LENGTH: 20
<212> TYPE: DNA
<213> ORGANISM: Artificial Sequence
<220> FEATURE:
<223> OTHER INFORMATION: Chemically synthesized

<400> SEQUENCE: 92
tatctgcaga attcgccctt 20

<210> SEQ ID NO 93
<211> LENGTH: 20
<212> TYPE: DNA
<213> ORGANISM: Artificial Sequence
<220> FEATURE:
<223> OTHER INFORMATION: Chemically synthesized

<400> SEQUENCE: 93
gtgtgctgga attcgccctt 20

<210> SEQ ID NO 94
<211> LENGTH: 20
<212> TYPE: DNA
<213> ORGANISM: Artificial Sequence
<220> FEATURE:
<223> OTHER INFORMATION: Chemically synthesized

<400> SEQUENCE: 94
tatctgcaga attcgccctt 20

<210> SEQ ID NO 95
<211> LENGTH: 20
<212> TYPE: DNA
<213> ORGANISM: Artificial Sequence
<220> FEATURE:
<223> OTHER INFORMATION: Chemically synthesized

<400> SEQUENCE: 95
gtgtgctgga attcgccctt 20

<210> SEQ ID NO 96
<211> LENGTH: 18

```
<212> TYPE: DNA
<213> ORGANISM: Artificial Sequence
<220> FEATURE:
<223> OTHER INFORMATION: Chemically synthesized

<400> SEQUENCE: 96

ggtcttgcga tgattatc                                                    18


<210> SEQ ID NO 97
<211> LENGTH: 18
<212> TYPE: DNA
<213> ORGANISM: Artificial Sequence
<220> FEATURE:
<223> OTHER INFORMATION: Chemically synthesized

<400> SEQUENCE: 97

gagaggaatg gcagcaga                                                    18


<210> SEQ ID NO 98
<211> LENGTH: 18
<212> TYPE: DNA
<213> ORGANISM: Artificial Sequence
<220> FEATURE:
<223> OTHER INFORMATION: Chemically synthesized

<400> SEQUENCE: 98

catgacgggt ttgagatt                                                    18


<210> SEQ ID NO 99
<211> LENGTH: 18
<212> TYPE: DNA
<213> ORGANISM: Artificial Sequence
<220> FEATURE:
<223> OTHER INFORMATION: Chemically synthesized

<400> SEQUENCE: 99

aatctcaaac ccgtcatg                                                    18


<210> SEQ ID NO 100
<211> LENGTH: 18
<212> TYPE: DNA
<213> ORGANISM: Artificial Sequence
<220> FEATURE:
<223> OTHER INFORMATION: Chemically synthesized

<400> SEQUENCE: 100

tctgctgcca ttcctctc                                                    18


<210> SEQ ID NO 101
<211> LENGTH: 19
<212> TYPE: DNA
<213> ORGANISM: Artificial Sequence
<220> FEATURE:
<223> OTHER INFORMATION: Chemically synthesized

<400> SEQUENCE: 101

gatcaacccg gagaggaat                                                   19


<210> SEQ ID NO 102
<211> LENGTH: 18
<212> TYPE: DNA
<213> ORGANISM: Artificial Sequence
<220> FEATURE:
<223> OTHER INFORMATION: Chemically synthesized - b05104h sequenceing
      primer

<400> SEQUENCE: 102
```

ccatgacggg tttgagat 18

<210> SEQ ID NO 103
<211> LENGTH: 20
<212> TYPE: DNA
<213> ORGANISM: Artificial Sequence
<220> FEATURE:
<223> OTHER INFORMATION: Chemically synthesized - b05105c sequenceing primer

<400> SEQUENCE: 103
caaccgacct gacaagtgac 20

<210> SEQ ID NO 104
<211> LENGTH: 18
<212> TYPE: DNA
<213> ORGANISM: Artificial Sequence
<220> FEATURE:
<223> OTHER INFORMATION: Chemically synthesized - b05105e sequenceing primer

<400> SEQUENCE: 104
atctcaaacc cgtcatgg 18

<210> SEQ ID NO 105
<211> LENGTH: 19
<212> TYPE: DNA
<213> ORGANISM: Artificial Sequence
<220> FEATURE:
<223> OTHER INFORMATION: Chemically synthesized - b05105f sequencing primer

<400> SEQUENCE: 105
attcctctcc gggttgatc 19

<210> SEQ ID NO 106
<211> LENGTH: 51328
<212> TYPE: DNA
<213> ORGANISM: Zea mays
<220> FEATURE:
<221> NAME/KEY: misc_feature
<222> LOCATION: (1680)..(3338)
<223> OTHER INFORMATION: opie2 marker
<220> FEATURE:
<221> NAME/KEY: misc_feature
<222> LOCATION: (25455)..(25512)
<223> OTHER INFORMATION: Maize genomic sequence displaced by MIR162 heterologous DNA.
<220> FEATURE:
<221> NAME/KEY: misc_feature
<222> LOCATION: (43275)..(45086)
<223> OTHER INFORMATION: gag marker

<400> SEQUENCE: 106
agatctagag attcgtcatt tgtagaaagg atagaaaggt gattgctagg aagttagggg 60
caaaatgcaa gggtgataaa acttgcattt ggatccctaa ggaaattgtg actaaccttg 120
taggacccaa caagagttgg gtacctaagt cccaagccta aatttgcctt gcaggtttat 180
gcatccgggg gttcaagctg gattattgat agcggatgca caaaccatat gacgggggag 240
aagaagatgt tcacctccta tgtcaagaat aaggattccc aagattcaat tatattcggt 300
gatgggaatc aaggcaaggt aaaagggtta ggtaaaattg caatttctaa tgagcactcc 360
atatctaatg tgtttttagt agagtctctc agatataatt tgctatctgt tagtcaatta 420
tgcaacatgg ggtataactg tctatttacc aatgtagatg tgtctgtctt tagaagaagt 480
gatggttcac tagcttttaa gggtgtatta gacggcaaac tttatttagt tgattttgca 540

```
aaagaagagg ccggtctaga tgcatgctta atagctaaga ctagcatggg ctggctgtgg    600

catcgccgct tagcacatgt ggggatgaag aaccttcaca agcttctaaa gggagaacac    660

gtgataggtt tgactaatgt gcaattcgaa aaagatagac cttgtgcagc ttgtcaagca    720

gggaaacagg tgggaagcgc tcatcacacc aaaaatgtga tgacaacatc aagacccctg    780

gagctgctac atatggacct cttcggaccc gtcgcctatc tgagcatagg aggaagtaag    840

tatggtctag ttatcgttga tgacttttcc cgcttcactt gggtgttctt tttgcaggat    900

aaatctgaaa cccaagggac cctcaagcgc ttcctcagga gatctcaaaa tgagtttgag    960

ctcaaggtga agaagataag gagcgacaac gggtccgagt tcaagaacct tcaagtggag   1020

gagttccttg aggaggaagg gatcaagcac gagttctccg ctccctacac accacagcaa   1080

aatggtgtgg tagagaggaa gaacatgacg ctaatcgata tggcgagaac gatgcttgga   1140

gaattcaaga cccccgagtg tttctggtcg gaagccgtga acacggcttg ccacgccatc   1200

aacagggtct accttcaccg cctcctcaag aagacgtcgt atgagcttct aaccggtaac   1260

aaacccaatg tatcttactt tcgtgtattt gggagcaaat gctacattct agtgaagaag   1320

ggtagaaatt ctaagtttgc tcccaaagct gtagaagggt ttttgttagg ttatgactca   1380

aatacaaagg cgtatagagt cttcaacaaa tcatcgggtt tggttgaaat ctctagcgac   1440

gttgtatttg atgagactaa tggctctcca agagagcaag ttgttgattg tgatgatgta   1500

gatgaagaag atgttccaac ggctgctata cgaaccatgg cgattggaga agtgcggcca   1560

caggaacaag atgaacgaga tcaaccttct tcctcaacaa cggtgcatcc cccaactcaa   1620

gacgatgaac aggttcatca acaggaggca tgtgatcaag gggagcacaa gatgatcatg   1680

tgatggagga agaagcgcaa ccggcacctc caacccaagt tcgagcgatg attcaaagga   1740

atcatcccgt cgatcaaatt ctgggtgata ttagcaaggg agtaactact cgatctcgat   1800

tagttaattt ttgtgagcat tactcctttg tctcttctat tgagcctttc agggtagaag   1860

aggccttgct agatccggac tgggtgttag ccatgcagga ggaactcaac aacttcaagc   1920

gcaatgaagt ttggacactg gtgcctcgtc ccaagcaaaa tgttgtggga accaagtggg   1980

tgttccgcaa caaacaggac gagcacgggg tggtgacgag gaacaaggct cgacttgtgg   2040

caaaaggtta tgcccaagtc gcaggtttgg actttgagga gacgtttgct cctgtggcta   2100

ggctagagtc aattcgcatc ttgctagcat atgccgctca ccactctttc aggttgtacc   2160

aaatggatgt gaagagcgct ttcctcaacg ggccgatcaa ggaagaggtg tacgtggagc   2220

aacccctgg cttcgaggat gaacggtacc ccgaccacgt gtgtaagctc tctaaggcgc   2280

tctatggact taagcaagcc ccaagagcat ggtatgaatg ccttagagac tttttacttg   2340

ctaatgcttt caaggttggg aaagccgatc caactctgtt cactaagaca tgtgatggtg   2400

atttgtttgt gtgccaaatt tatgtcgacg acataatatt tggttctact aaccaaaagt   2460

cttgtgaaga gtttagcagg gtaatggcgc agaaattcga gatgtcaatg atgggcgagt   2520

tgaactactt ccttgggttc caagtgaagc aactcaagga tggcaccttc atctcccaaa   2580

cgaagtacac gcaagatcta ctaaagcggt ttgggatgaa ggacgccaag cccgcaaaga   2640

ctccgatggg gaccgacgga cacaccgacc tcaacaaagg aggtaagtcc gttgatcaaa   2700

aagcataccg gtcaatgata ggttctttac tttacttatg tgctagtaga ccggatatta   2760

tgcttagcgt atgcatgtgt gctagatttc aatccgatcc taaggagtgt cacttagtgg   2820

cggtgaagcg aattattaga tatttggttg ctacgccttg cttcgggctc tggtatccaa   2880

aggggtctac ctttgacctg gttggatact cagattccga ctatgttgga tgtaaggtcg   2940
```

-continued

```
ataggaagag tacatcgggg acgtgccaat tcttaggaag gtccctggtg tcgtggaact   3000
ctaagaaaca aacctccgtt gccctatcca ccgctgaggc cgagtatgtt gccgcaggac   3060
agtgttgcgc gcaactactt tggatgaggc aaaccctccg ggactttggc tacaatctga   3120
gcaaagtccc actcctatgt gacaatgaga gtgctatccg catggcggaa aatcctgttg   3180
aacacagccg cacaaagcac atagacatcc ggcatcactt tttgagagac caccagcaaa   3240
agggagatat cgaagtgttt catgttagca ccgagaacca gctagctgat atcgaagtgt   3300
ttcatgttag caccgagaac cttttgcagg ctgcgtagta agctaaatgt cttagattcg   3360
cggaacttgg attgaattgt agcatacatg tgtttatgcc tttgatcatg ttcattctgc   3420
attttgttgc ttattgtggt gctcaagttg tacaaacact ccctggatct cacaagtccg   3480
ttgcaaagtg atgctgagag cacctagagg gggggtgaat aggtgatcct gtaaaaactt   3540
aacttatagc cacaaaaact tgttaaaggt tagcacaata attgccaagt ggctaaagag   3600
gagatcttgc acaatacgat tatcacagag aattcaacac agaggagaca tagtgattta   3660
tcccgtggtt cggccaagta caaaacttgc ctacttccac gttgtggcgt cccaacggac   3720
gagggttgca atcaaccctt ctcaagcggt ccaaagaccc acttgaatac cacggtgttt   3780
ttgccttgct tatctttatc ccacttacga ggaatctcca cagattggag tctctcgccc   3840
ttacacttaa gattcacaaa gaagcacgga gtaagggagg gaagcaacac acacaaatcc   3900
acagcgaaat gcgcacacac acggccaaga atcgagctca aagactatct cacagtttct   3960
cacaagaaca gagctcgaat cacttagaat cacaaacgga tgcgcaaaga ctgagtgtgg   4020
atgatcaaga atgctcaaag gttgcttggt gtctccctcc atgcgtctag ggtccctttt   4080
tatagcccca aggcagctag gagccgttga gaacaaatct ggaaggccat ctttgccttc   4140
tgtcgtcggg cgcaccggac agtccggtgc ccgattcctt tccttaattg gcgaagccga   4200
ccgttgcaga tgcgggagcc gttggcgcac cggacatgtc cggtgcacac cggacagtcc   4260
ggtgccccct tccgaccgtt ggctcggcca cgtgtcccgc gcagatcgcg cggtcgaccg   4320
ttggctcagc cgaccgttgg ctcaccggac agtccggtgc acaccggaca gtccggtgca   4380
caccggacag tccggtgaat tttagccgta cgccgtcagc aaattcccga gagcggcctc   4440
ttcggccaag gcagcctggc gcaccggaca ctgtccggtg caccaccgga cagtccggtg   4500
ccccagaccg aaacagcctc ttggctgtac acagccaagt cttctcttct cttcttcttt   4560
ctgtttctaa cacttagaca aatatattag tacacaaaac caatgtacta aggcttagaa   4620
acatacettt gctctagatt ttcactttgt tcatccatgg gcattgattc acatttaagc   4680
acttgtgttg acactcaatc accaaaatac ttagaaatgg cccaagggca catttccctt   4740
tcagatgcac agtttgaggg ggagatgtgt tacaacttga ccctttgaga ctaaccgtat   4800
gcttgagttt gcttgtttta gtctcaaagg agaattaaaa gggaaaaggt ggacttggac   4860
catgaaagac ttccactgca ctccgatgag agggtagctt attccaagtt catctcatgt   4920
actcttattg cctttgtatt cttattgaag attttggtga ggcaatgggg ttcttgggcc   4980
aagattgatc ctgttttggt gcttgatgcc aaagggggag aaaataaggg ccaaagcaat   5040
aaatggatca gctaccactt gagaaatttt gaaaacagta gaatagagct tttggtttgt   5100
caaatctctt ttgttgtctc ttttgtcaaa agttggcctc ttgtggggag aagtgttgat   5160
tatgggaaaa agggggagtt tttgaaatct ttcctttgga atgactctcc ttatgcttca   5220
acatgtgtgt ttgacttaga gatagagatt tgagtttgat ttgcaaaaac aaaccaagtg   5280
gtggcaaagg atgatccata tatgccaaat tgaatcaaaa taaatttgag tttttatttg   5340
```

```
aagtaatatt gcacttgttc tagttgcttt atgtagtgtt ggcataaatc accaaaaagg   5400
gggagattga aagggaaatg tgcccttggg ccatttctaa gtattttggt gattgagtgc   5460
caacacaagt gcttaaatgt gaattcatgt ttatggatga ataaagtgaa aatcaagagc   5520
aaaggtatgt ttctaagtct tagtacattg gttttgtgta ctaatatact tgtctaagta   5580
ttggaaacag gaagaaaaag aaaagaaaag agttggctgt gtacagccaa gaggctgttt   5640
cggtctgggg caccggactg tccggtggtg caccggacag tgtccggtgg tgcaccggac   5700
agtgtccggt gcgccaggct gcctcggccg aagtagccgc tctcgggaat tcgctgacgg   5760
cgtacgacta taattcaccg gactgtccgg tgtgcaccgg actgtccggt gtgcaccgga   5820
ctgtccggtg agccaacggt cggccgggcc aacggtcggc cgcgcgatct gcgcgtgaca   5880
cgtggccgag ccaacggcta gaagggggca ccggactgtc cggtgtgcac cggacatgtc   5940
cggtgcgcca acggctctct ggcgggcaac gggcggctgc gccattttag gaaggaaatc   6000
gggcaccgga cagtgtccgg tgtgcaccgg actgtccggt gcgcccgacg acagaaggca   6060
aggatggcct tccagatttg ttctcaacgg ctcctagctg tcttggggct ataaaaggga   6120
cccctaggcg catggaggag tacaccaagc attcctacaa cattcctaag caccaagaca   6180
tcgatctcac gcattcgttt cattgtgata gcatctagag ctcttgttga gttgcgaact   6240
ctttgagttg tgttgcgagc tcttgttgcg acttgtgtgc gtgttgttgc tctgatcttt   6300
tgaagtcttg tgtgcgttgc tcattccccc tttgctctgt gttctttgtg aacttcaatt   6360
gtaagggcga gaggctccaa gttgtggaga ttcctcgcaa acgggattga gaaaaaaagc   6420
aagcaaaaca ccgtggtatt caagtgggtc tttggaccgc ttgagagggg ttgattgcaa   6480
ccctcgtccg ttgggacgcc acaacatgga gtaggcaagc gttggtcttg gccgaaccac   6540
gggataaacc actgtgtcgt ctctgtgatt gatctcttgt ggtattgtgt tttgttgaga   6600
ctcctttcta gccacttggc atttattgtg ctaacactta acaagttttt gtggctataa   6660
gtttaagttt tacaggatca cctattcacc ccccccccct ctaggtgttc tcacctatgc   6720
acccgtagct aggcttgagt caattcgcat attattggcc tatgctactt accatggctt   6780
taagctttat caaatggacg tgaaaagtgc cttcctcaac ggaccaatca aggaagaggt   6840
ctatgttgag caacctcccg gctttgaaga cagtgagtat cctaaccatg tttataggct   6900
ctctaaggcg ctttatgggc tcaagcaagc cccaagagca tggtatgaat gccttagaga   6960
tttccttatc gctaatggct tcaaagtcgg caaggccgat cctactctat ccactaaaac   7020
tcttgacaat gatttgtttg tatgccaaat ttatgttgat gatatcatat ttgggtctac   7080
taacgaatct acttgtgagg aatttagtag gatcatgaca cagaaattcg agatgtctat   7140
gatgggggag ttgaaatatt tcttaggatt tcaagtgaag caactccaag agggcacctt   7200
cattagccaa acgaagtaca ctcaagacat tctaaacaag tttggaatga aggatgccaa   7260
gcccatcaaa acacccatgg gaacaaatgg gcatctcggc ctcgacacgg gaggtaagtc   7320
cgtggatcaa aaggtatacc ggtcgatgat tggttcattg ctttatttat gtgcatctcg   7380
accggacatt atgctttccg tatgcatgtg tgcaagattc caatccgacc ctaaggaatc   7440
ccaccttacg gccgtaaaac gaatcttgag atatttggct tatactccta agtttgggct   7500
ttggtaccct cggggatcca cttttgattt aattggttat tccgatgctg attgggcggg   7560
gtgtaagatt aataggaaga gcacatcggg gacttgccag ttcttgggaa gatccttggt   7620
gtcttgggct tcaaagaagc aaaattcggt tgctctttcc accgccgaag ccgagtacat   7680
tgccgcaggt cattgttgcg cgcaattgct ttggatgagg caaaccctgc gggactatgg   7740
```

```
ttacaaatta accaaagtcc ctttgctatg tgataatgag agtgcaatca aaatggccga   7800
caatcccgtc gagcatagcc gcactaagca catagccatt cggtatcatt ttcttaggga   7860
tcaccaacaa aagggagata tcgagatttc ttatattaac actaaagatc aattagccga   7920
tatctttacc aagcctcttg atgaacaaac ttttaccaaa cttaggcatg agctcaatat   7980
tcttgattcg cgcaattttt tttgctagat tgcacacgta gctcatttat atacctttga   8040
tcatatctct ttcatatgct atgactaatg tgtttttcaa gtccatttca caccaagtca   8100
taggtatatt gaaagggaat tggagttttc ggcgaagaca aaggcttcca ctccgtaact   8160
catcctttgc catcgctcca agaaaaggac cttgtctttg ggggagagag taaaagccca   8220
aagcaaaagg actggacttc gtctttggta taatcttaac tcatttactt atgaccaaag   8280
gggaagatag tacttctatg ggctctaatg attccgtttt tggcgattca tgccaaaggg   8340
ggagaaagta tgagcccaaa gcaaaaggac cgcaccacca ccaatttcaa aaacttagtg   8400
ctttctaaga gtatttatca attggtatcc tattgtgttc aaaaggagga gaaaattagt   8460
tttttcaaaa atgtatatca aaaccctctt gaacactaag aggtggatct cctttagggg   8520
gaatttttttg ttaagtcaaa ggaaaagcat ttgaaacagg gggagaaaat ttcaaatctt   8580
gaaaatgctt tgcaaactct tattcattta cctttgacta tttgcaaaag atcttttgaa   8640
atggatttac aaaaagaatt tgcaaaaaca aaacatgtgg tgcaaacgtg gtccaaaatg   8700
ttaaataaga aagaaacaat ccatgcatat cttgtaagta gttatattgg ctcaattcca   8760
agcaaccttt acacttacat tatgcaaact agttcaatta tgcacttcta tatttgcttt   8820
ggtttgtgtt ggcatcaatc accaaaaagg gggagattga aagggaatta ggcttacacc   8880
tagttcctaa ataattttgg tggttgaatt gaccaacaca aataattgga ctaactagtt   8940
tgcccaagtg tatagattat acaggtgtaa aaggttcaca ctcagccaat aaaaagacca   9000
agttttggat tcaacaaagg agcaaagggg caaccgaagg cacccctggt ctggcgcacc   9060
ggactgtccg gtgtgccacc ggacatgtcc ggtgcaccag ggggactcag actcaaactc   9120
gccaccttcg ggaatttcca gaggcgactc ggctataatt caccggactg tccggtgtac   9180
accggacatg tccggtgctc caaggaaggt cggcctcagg aactcgccag cctcgggttt   9240
tctccctcgc cgctccgcta taattcaccg gactgtccgg tgtgcaccgg actgtccggt   9300
gcaacctcgg agcaacggct acttcgcgcc aacggctacc tgcaacggca tttaatgcgc   9360
gcgcagcacg cgcaggagtc agaatcgccc atgctggcac accggacagc aaacagtaca   9420
tgtccggtgt gcaccggaca cccaggtggg cccacaagtc agaagctcca acggtcagaa   9480
tccaacggca gtgatgacgt ggcagggggc accggactgt ccggtgtgca ccggactgtc   9540
cggtgcgcca tcgaacagac agcctcccaa cggccacttt tggtggttgg ggctataaat   9600
accccaacca ccccaccatt cattgcatcc aagttttcca cttctcaacc acttacaaga   9660
gctaggcatt caattctaga cacacccaaa gtgatcaaat cctctccaat tcaacacaaa   9720
gccctagtga ctagtgagag tgatttgccg tgttcatttg agctcttgcg cttggattgc   9780
tttctctctt tcattctttc ttgtgttcaa tactcacttg taaccaaggc aagagacacc   9840
aattgtgtgg tggtccttgc ggggaggttt ttctcccggt tgatttgaga agagaaagct   9900
cactcggtcg gagggaccgt ttgagagagg gaaagggttg aaaaagaccc ggcctttgtg   9960
gcctcctcaa cggggagtag gtttgagaga accgaacctc ggtaaaacaa atcctcgtgt  10020
ctcacttcat tatttgcttg cgatttgttt tcacgccctc tctcggactc gattatattt  10080
ctaacgctaa cccggcttgt agttgtgttt atatttgtaa atttcagttt cgccctattc  10140
```

```
accccccccc ctctaggcga ctatcaccag gcggtagtcc gcgagccaca gttccggtct  10200
cgtttccccc gaatacttcg tgatagtagt cgggggtcgg aaccgggtcg ggaacgacgc  10260
ccgtcggatg gcccgactga aggcttgcgg accgggtggt tcgggcgagg gactccgatc  10320
cctccccact gtcgtagcgc ccccccacgc ctggggtggt agcctcggcg caccctttcg  10380
tcgaggtggg cccgacggtc gcgtcgatgg tgctcgttgc cgaggtggcc cggggccgca  10440
ggcgcggtgt tgcgcgtgcg tccggtatag accgaggctt cccgcataaa ttgggaagtc  10500
gcggcgtgag gttccgaggg gtatccccgc ctccgggagg cagtgctctc ggcccgtcgg  10560
gccgcagcgc cttccaggag attcttgagc tctccctgga ttcgccgacc ctcggtggtt  10620
gatggctccg gcatcgtgcg gaggagcatc gctgcggctg ccaggttctg accaaccccg  10680
ctggatgcgg gcggcggcct gagcctgaca tcgttggcga cgcggtgctg gagaccttgg  10740
ggcaggtgac gtatttctcc ggccgagggt tggcccgccc atacctgccc gacgtcccgg  10800
cggatcgtct caagcgcccc tgttccctcg tcgagcctgg cctgcgcccc gcggacttgc  10860
tcgagctgtg ggtcgtgacc ccccgccgga acggggacca cagctagctc ccgcgggatg  10920
tcggcgcgag ggcaccggcc taggaaaatc accgtcctcc ggcatgccaa gatggttgcc  10980
ttcggaggga tcccctagct cgacgtggaa acattcgcgg cttgggccgc agtcctcgtc  11040
gtcaaggctg cggcttccgt cggaacagtc ggagaggcag tagtcacatg cggtcatgaa  11100
gtcccgcatg gcactggggt tgccaagtcc agagaaaccc caacagatgc tgggatcgtc  11160
atcttcctcg gacccagagg gcccgtaggt cgagacgtcc gtcaatcggt cccaaggcga  11220
ccgcatacga aaccccagtg gggttgcact cgcctcaatg agagcgcccg ccaaagcgag  11280
gtcgcttggc gggtcgaggc cgagtcgaaa tgacgtaaga tgggagttag ttagtacctt  11340
ttggtcgacg cggagcgacg tagtcacatc ggggactggt tgcaccgtca tctcaggtac  11400
gagggcgacg tcctgcaggc tttccgcgag cgtgctggcg tcttcttctt gctcgggatc  11460
agcgtgtcgc ggggggacgg cgcttgcctt cgtctcgaac gcgaggtcga cgcccggcgt  11520
gccctccgtg ggggcgctgg ggacgtcgat tcgctcgaca gccgacgaag cgcggcctcc  11580
cacttggcct tggttgcccc gcctcctcct ccgttggcgg gggagaggac ggggcgagct  11640
cgaatgttgt ttttccaccg cgcggggaag atgtcgtcgg ttccgccgcc gacgggcggg  11700
atgtcggccg ccattgtcgt tgtcgcgcgg cggtggaagg agtatcatgt cgtagctgcc  11760
gtcgaaggac atgaactcaa gactcccgaa acggagcacc gtcccgggcc ggagaggttg  11820
ctggagactg cccatctgga gcttgacggg aagctgttcg tcagcacgca gcaggcccct  11880
acctggcgca ccaactgtcg gcgtttcgag accggggggt ccccgagccg acgagtgagt  11940
gtgccgcgtg ccccagccca gatgggtcga gcgcgtgggc gagcgcgaag gggggagagg  12000
cgaggtgtcc ggagacgggc gtgagagagg tggagatccc gcggccttcg tgttcgtccc  12060
gcgcccaggt cgggtgcgct tgcagtaggg gggttacaag cgtccacgcg ggtgagggaa  12120
gcgagcggcc ccaagagagc gcctgtctcg tcctcgtccc cgcgcggcca accttctcta  12180
agaaggccct ggtccttcct tttataggcg taaggagagg atccaggtgt acaatggggg  12240
tgtagcagag tgctacgtgt ctagcggagg gagagctagc gccctaagta catgccaatg  12300
tggcagccgg agagatcttg gcaccctact ggcgtgatgt cgtggctgtc ggaggagcaa  12360
cggagcctgg cggagggaca gctgtcggag cggtcgagtc cttgctgacg tccccttgct  12420
tccgtaagag agctgagagc cgccgtcgtc acagagcttg tggggcgcca tcattgccca  12480
tctggtggag ctagccagag gggacaccgg tcttgttctt cgtgacccga gtcggctcgg  12540
```

-continued

```
ggtaggatga tgatggcgct tcccgttgac gtggcgggcc tgtgccctag gtcgggcgac  12600
gtgggggctc ctccgaagcc gaggtcgaat ctgtcttccg tggccgaggc cgagcccgag  12660
cccctgggtc gggcgaggcg gaggtcgttc ggtagaggcc agggcggagt ccgagccctg  12720
gggtcgggcg aagcggagtt tgtcgtcttc cgggtctcag cccgagtccg agctttgggg  12780
tcgggtggag cggagttcgt cgtcttccgg gtcttagccc gagtccgagc cctggggtcg  12840
ggcggagcgg agttcgccgt cttccgggtc ttagcccgag tccgagccct ggggtcgggc  12900
ggagcggagt tcgtcgtctt ccgaggctga gcccgagtcc gagccctggg tcgggcggag  12960
cggagcttcc tatggcgcct ttggcaaggc ctgactgcct gtcagactca ctttgtcgag  13020
tggcactgca gtcggagtgg cgcaggcggc gctgtccttc tgtcagaccg gtcagtggtg  13080
cggcggagtg acggcggtca cttcggctct gccgggggc gcgcgtcagg ataaatgtgt  13140
caggccacct ttgcgttaaa tgctcctgca actcggtcag tcggtgcggc gatttagtca  13200
gggttgcttc ttagcgaagc caaggcctcg ggcgagccgg agatgcgtcc gccgttaaaa  13260
ggggggcctc gggcgagaca gaagtccctc gaggtcggct gcccttggcc gaggctaggc  13320
tcgggcgaag cgtgatcgag tcactcgtat ggactgatcc ctgacttaat cgcacccatc  13380
aggcctctgc agctttatgc tgatgggggt taccagctga gaattaggcg tcttgagggt  13440
acccctaatt atggtccccg acaactataa accccaaagg gttgttttag aagtctaggt  13500
agctttttttg tctattagag agagagtata ttagaaattt attttagtgt gtgatttctc  13560
gcaattgaga tatgttttta aagtagataa taataataaa ataaacatct atgatggagt  13620
tttgttgtgc atttggattt tgaatctcaa cttcaaaact gtattagaat ttgaaacttg  13680
aaaataaaaa ctgaaataaa aagataagga aaaaacaaaa ccactgtcgg gccactatct  13740
cccctagtcc tagccatgcc ccctcttcca tcagtcgagt gggtcagttg gccggcccaa  13800
caccgcacca gcatgatagc atctcgcacc cgcctggttg gtttcacagg cgaccatgcg  13860
ggacccacgt tcagcctctc cgcgctcgtg cctatggacg gtagtcggca gacaccaatc  13920
aatggggtcc gcgcgaccgc gcttcagttt ctcgtcgtcg tacgcatggg tcactgttag  13980
caccacggaa cacagaagac agcaagggaa agaggaaggg caacttggag cagaagaaga  14040
agaatagggt acgcaacgtg gcggatgttc tttgttattt cgttcatatc ctcagcagcc  14100
tagcacatag tctatatatg tcactcctga actggactgc cacaatacgg cttacacggt  14160
ccactgcggc ccaaccacat ttaagtttgg cttcctggtc ctcagcacgc gaggctgcat  14220
catctcctga tgtgttgccg ctgtctccag gtcttgattc ccacttgctg ccagcttctt  14280
cttgtcttcc gacgacgctt tgctgacatt cccctgtcct cgagcgccag cttggtccca  14340
gatcaacgct tttggaaacc gagcacgcag tgcctcaacg tcctcccagg tagccagatc  14400
ctcagtcatg cctgaccaga ccaccttgac ctgcgcgatt aactcaccac cacggtcaat  14460
gaagcggcat tgtagaatac atgtaggcac ctggataggg ccaacatctt ggggcagctg  14520
aggtgaggcc cgttgatcac gcccgatgac ccgtttgagc tgtgacacat gaaaaattgg  14580
gtgaatagag ctggaggccg gtaaagctag acggtaagcc acggaaccca gacgatcgta  14640
atctggaaag gaccaaagaa tttgaaggac aacttgtgat tggagcgtgt agcaaccgaa  14700
gattggatat aaggttgtaa cttcaagtaa acccaatcac ccaccaaaaa cacgcgttca  14760
ctgcgctgct tgtcagcttg ccgtttcata cggtcttgag ctcgatgcag atgcaattta  14820
atgactttgg tcataagctc tcgttccttc aaccaagttt cgagctctgg ctgtggcacc  14880
acaatatcaa ccaaaattcc aaaatatcgc ggagtgtggc catataacac ttcaaagggt  14940
```

-continued

```
gtacgcccca aggttgaatg tactgtggta ttgtaccagt attcagcaac tgacagccaa  15000
gctgaccaac gtgaaggaca agtgtgcaca tagcaacgaa gaaaagtttc caagcattga  15060
ttcaagcgct ctgtttgtcc atcggattgg ggatggtaag aagaggacat ggacagattg  15120
gtacccgtga tctgaaatag ttgttgccag aatgagctag taaaaattct gtcgcgatct  15180
gaaatgatgt tgacaggtaa cccgtgtagc ttgtacacat tgtcaagaaa aacacgagcc  15240
actttagcag ctgtgaaggg atggagtaaa ggtaagaagt gtccatactt cgaaaattta  15300
tccacaacca ccaagatgca gttatagtga gctgaacggg gcaaaccttc aataaaatcc  15360
aatgaaactg tatgccacgc ttgtggtgga acttccaaag gctgcaatag gccaggatat  15420
ttagcacgat cgggcttgga ttgctggcat accgtacaag attgaacgta ctgtagcaca  15480
tcagcacaca tacctggcca atagaacatt tgtttcactt tgtgatatgt tgctggggct  15540
ccagaatgac ctccgaccgc cgtatcatgc atagcttgta ataccttctg ttgcagctgc  15600
aaattgccgc ccacccagat tctatttttg tgtcgaatga ttccttgatg caaggaaaaa  15660
ggagctttgt ctgcagaatt caaaattaat tgagccagca actgtttact agtaggatcc  15720
ttgtcatagc cttccactcc ctcctgcagc caagtaggca cactgtgaga aatagcacaa  15780
cagtgactat cttcctggac ttttcgagac agtgcatctg cagctccatt atccacccct  15840
tttctgtaga caatcttata ttgcaagcca gccaatttcg tatacatttt ctgttgccag  15900
atagtatgta aacgctgctc attcagttgt gctaaactcc tgtgatctgt atagataatg  15960
aactcagcca actgaagata ggacctccat tgagcaatgg ctaaaataat ggccatgtat  16020
tccttttcat aggtcgagag tccctgattt ttcggtccaa gagccttgct cagaaacgct  16080
aaaggatgtc cactttgcat aagcaccgca cccacaccat aataggaagc ataagtatga  16140
atataaaatg gctgggaaaa tcaggcagag ctaacactgg tgcagtgacc aatgcttgtt  16200
tcaaaacttc aaaagcttta aaatgatcca ctgtccacac aaataaagtg tgtttcttca  16260
agagatcaaa taaaggtcta ctgataattc caaagtgctt gacaaatttt ctgtaaaaac  16320
cggctagacc caggaaacat cgcagttcct tagcattggt tggtactgcc caagaggata  16380
tggcttgaat tttactagga tctgtggata ccccttgctc actgatgata tggcccaagt  16440
aagcaatatt tgtttgagca aattcacact tagataattt gactttccaa ttatcagaca  16500
acaataattg caaaaccttc tgcagatgca gtagatgctc ttcaaatgac ttactgtaaa  16560
ccaagatgtc atcaaaaaaa ccagagcaca ttttctcaat actggtttca gggtttcatt  16620
cgttgcactt aagaatgtgt taggagcacc tgtcaagtca aaagccatca ctctaaactc  16680
atagtggccc acatgagttt gaaatgctgt tttatattct tcgccagatt tcaaaagaat  16740
ttggtgatat ccagctctga gatccagttt actaaaccat ttagagtggg cgagctcatc  16800
aatcaattgg tcaaacacag gaactgggta tttgctcttg agagtgaggg cattcaaata  16860
cctatagtcc acacaaaatc gccatgtcat gtctttttc ttgaccaaca ccatagggga  16920
agcaaaagaa ctattgcttt tctgaataac accttgatga aacatctctt gaacttgttt  16980
ttcaatttca tccttcaggg ctggaggata cctgtaaggt ctgacagaca ctggctgagc  17040
accttccacc aaaggaatag catggtcaca atccctgctt gggggcaaac cctgaggttc  17100
gtcaaagact gagctgaact gttgtagcaa tgcttgaatt gcaggatggc tgtcaggaga  17160
agagcctacg gaactgacag attccatgaa caacaactct atcatagtat cagcaggtac  17220
ccctggggtg ttgccctgca gcagcacaga agagccttga tatggtataa ttagccactt  17280
ttgagcccaa tccactctca tgggactaaa ggatttaagc caatccatgc ctaccaccat  17340
```

```
gtcgtagtag ggaaggggca ggaatgaaac gtccgaagta aaactgcagt tctgaatctg  17400
ccattgtgcc tgcaacaatt tgtaatgaca agtcaccata gccccattgg ccacttgcac  17460
ttgcagagta gatgccatag atgtcacccc ttgcaagtgt ggtctaagtt gatcattcaa  17520
aaaggtgtgt gagctgccac tatctatcag aataagtaag ggatgattct gaatgctccc  17580
atttaatttc agagtttgtc gaccagtcga ccccgtccat gcagatttgg aaatagtcac  17640
gaacaactgt tctagagcag gttcaggtgg agataagtca gattcgggta cttcttcatc  17700
caccaataat gaccaaacct cctccatagc atgaagttga gcagtggcaa cacatttgtg  17760
accgggattc cacttttctg cacacttgtc acaaagaccc tttgctcgac gaaaacgtcg  17820
caacgattcc agcttatcag aatgagatgc agattgagtt gaatccttgt ttgaagtcca  17880
tttagttgaa gcagacaact gcacaccagt cttggggcca gcatgacttg aatatggttc  17940
agaacggcgc caacgtctcg ccgttgtggc ctcctcctgc accaacgcga gagaacaggc  18000
agtgtccaaa ttcgacgggc gttgcaccat aataacagct ttaatatcat cacgcaaacc  18060
atctatgaac cgcattgtgt aatacaatgg gtcagcattt gcttcatatg cagacaagtg  18120
atcaacaagt attgaaaatt gttctacata ctcagctacg ataccggact gatgtatgtg  18180
gaaaagttga cgaattaagg attcatgctg ctctctacca aatctatcat gaagctggcg  18240
acaaaattca gaccacgaca acatacgcac cctctgacca acagactgta accatgatgc  18300
agcacgccca ataaaatgca tagtagctac acgaatccac atatatggtt ccacgtcata  18360
catatcaaag taattttcac aaagcgtctt ccacaactga ggattgtccc cgtcaaagtg  18420
agggaaatta accctcggta ggttaccgtg cccacagcga aacccctcgt gaccgccatt  18480
cagttcagtg tgacgaacag aatcatcaaa tggatcaata cgaggtgaat cgtggtacgt  18540
acccttgacc gggacatggg tttgagcatg accatgccca aacccacgcg cccggtgaca  18600
tggttcagcg tggtggccaa atggcccgtc agcgggttgt ttcccggcag atggatgctc  18660
ggacgccaac ccggaaggag tgaagagacc tggcttggtc tgatcagcgg cgatcgtctc  18720
acgctccatg aacttggtgg cacgcttgct ctcgaggaag aggttctcca gacgcctctc  18780
cacttctggg cgccaagtat ccacctcgga atgccccatc ttgagtgaga tgaagcgtgc  18840
ctccgcttgt tgcgccatcg cgtcgatccg ttgctcaatc gcgccgcagc gattctccag  18900
cgtcgcagcc atgcgctctt ccatctgcga caaggcctct agaaccttct gcatcgcgga  18960
atccataccg gcgaccgcag tggatcgagg gcgccgaccg ggtatgggat ccagattctc  19020
taggatgaac tagtctgata ccacctgtta gcaccacgga acacagaaga cagtaaggga  19080
aggaggaagg gcaacttgga gcagaagaag aagaataggg tacgcaacgt ggcggctgtt  19140
ctttgttatt tcgttcatat cctcagcagc ctagcacata gtctatatat gtcactcctg  19200
aactggactg ccacaatacg gcttacacgg cccactgcgg cccaaccaca tttaagtttg  19260
gcttcctggt cctcagcacg cgaggttgca tcgtctcctg atgtgttgct gctatctcca  19320
ggtcttgatt cccacttgct gccagcttct tcttgtcttc cgacgacgct ctgctgacag  19380
tcaccgcccg acagacttgt gggcccgctt cgccagaacc ttcgtctccc tcccgtaacg  19440
aactagggca caacacaaac ttgtacttgt gtagccgggg tgtgtttact ggccgaccgc  19500
acccgccttg gactcgtcca ctgcccctat ataaacggtc gcccccccgcc ctcgatcaat  19560
cagagtttag gagcccctgc tacctgttgt cgtgtggcgc cgtcgcaatg agctcgacgc  19620
cgcacgccat cgtaattcag ccacacctac gcttttgcct tgctttcggt aggaggtttg  19680
agggtttcgc cgtcgtacgt gggagctgct ggatgtttcg ttaggtgagg gaatctactg  19740
```

```
gaggcaggca ctgcgtgccg aggatcaccg ttgcatccca agccaccgtt cgacgtcgcc  19800
gactctcgcc ctcaatttag ttaccgacga ggaccccttg actgtttcgt ttgcttctca  19860
ctcgtaccta ggcacgagta gcgctttaga tcggttttgg ggcactcgga ttgctcgccg  19920
gtgttcagag attaccacag agtcacgctg tgctgagcgc gaggctcgac gctgcatgat  19980
cattgatcag accttgtccg tgttgtcttc attgaccaca gcttcgcata ccaccatttg  20040
gattggagaa atagagcgca aggtcgtcgg ttcgcgtgtg ctagcgagct gtcagggcgg  20100
agctctattt ctgccaccat gacgcgttgg tagagaaagg agcggcatca gttgatcagg  20160
attaaatccc gcgtacccct tcagcacatt aaatcaaagc cgtcagatct aatctagacg  20220
tttgtgattc gataatagcg tgtcggttta gtatttaaat ctggaccgtt gatctctaga  20280
tgatcgcctt aggtcgtgta ccagttagtg tagttgggtg aactttatta aagagcccct  20340
ataaaattta ggaattaacc tgcaatcacg tgatatttag aaagtcatgt agctaggtca  20400
tgttcttaac atattagacc cgatggattt tagaatcgga agtacacatt aaaggtatga  20460
ttctatactt agtacattag tttttgtgta ctaacacatt tgtctaagtg ctagaatgag  20520
aaaaaagaca aaaggaaaaa gagttggctg tgtacagcca actgctgttc agtctgggtg  20580
caccggactg tccggtgagc ctacagtcgg ccgcgcaatc tgcgcgtgac gcgtggccgg  20640
gccaacggtc tgatgggggc accggagtgt ccggtgtgca ccagacagtg tccggtgcgc  20700
caacggctcc aaatcttcaa cggtcggctg cgccaaaata ggaaagcaat cagcaccggg  20760
cagtgtccgg tggtgcaccg gactgtccgg tgcaccaccc gacagaaggc aaggataacc  20820
ttcctggatt gctctcaatg gctcctagct gccttggggc tataaaaggg accoctaggc  20880
gcatagagga gtacaccaag catactataa gcattcttga tcattcacac tccgtctctg  20940
ctcactcgat tgactttctt agtgatttga gctccgttct tgtggcgaat cttgtgctat  21000
tcatttgagc tcaagtcttg gctgtgtgtg cgtattgctg tggatttgtg tgtgttgctt  21060
ccctccccta ctctagtgct ttcactttga tccttattgt aagagcgaga gactccaagt  21120
tgtggagtaa atgaaactga accctaaacc ctaaaccctc taaaaatgac taaaatgcaa  21180
aatagacggc gcatacataa ctaggagtaa aatgtccgaa aaaaaatcgg ctcgagtctc  21240
gagactcgag tgccctctct gcctataaat cgaaccctaa cccttttttcg tacctgtttg  21300
tgtccttagg gtttagggtt ctctgctcat tcgttcgcca cctcgcccca agacgtctcg  21360
ctagggtttc gccacagccg ccgccatgcc tcgccgcaag cttaggtaac cttctcctct  21420
ggcgcctcct agggttttgt ttcgagattc ggttgttcct tgcgttgacg ggccggggct  21480
ggctcctcct ggatctgggg ctcaggcgcg taggcttggg cgttagtaga tttgattcag  21540
tcggtatgat gtcgttaatc gtttgtttta gtatgtgcaa atgatactgg ggttgtgggg  21600
ataggattgc gcatgtttgc catgtttagt tgcagaaata tccggatctg tttcttgcgt  21660
tcaatgggct gggtctcttc ctgtttagat aattgtaaga aatggacggg tgttcataat  21720
cgacagagat ccgattgctt ctcgaataac cgattgcaga tactatctgt tcgcaggcgg  21780
ttcagacagg ggcatagaac aaatctgaat ccccacgagg gaaggtttat ttccattaat  21840
cctttctcgt taggattcgt atagatttac atatatacta caggttgtct tatgaggtgt  21900
ttggtatatt cttgaaagtt aattcaccag ggtagtggac tgaatcttat gaatgttgta  21960
tgtgtgtagc tgtattgtat tgtccgttta taatgcctct ttgagtagcc attacagtcc  22020
ctgagtactg tcttggttta gttagggggc gcaaagcact ggacatctga tgtccactca  22080
ggccttttga gggggtacct cacctgtctt accaagaagt gccccccaag cagccttaga  22140
```

```
catacatcta cataatctct gtttgtaagt gcctctttga gtagccatta cagtccctgg  22200
gtactgtctt ggtttagtta gggggcacaa agcaatgggc atctgatgtc cactcacctt  22260
ttgaggggca ccttatctgt cttacaaaga agtgcccctc aagcagccct agacatatat  22320
ctacattatc actgtttgat ctgtcctcaa tgccacgtct tttcacttag tttttggcac  22380
tcatatttgc tttattgagt tgccactgta gttgtatata caatcttggt ttagttagga  22440
ggcacatgtg atcttgaaaa aaactgacat tgtagtgtta tcatctttcc tgttgaatgg  22500
tagacatgta atgcaaaaca ttcaaaagat tgcttgtgta cttgattagt atcaaggttt  22560
cagggagcga tgacatttct taatatattt ggaggactca acttagttac taactggact  22620
acaagtaaca aataatgtgc ctcttgtctt tattcatccc ttcttagatt gattcctaca  22680
gttaactgct attttcatca tttttgctgg tggaagatgt ggttgagctt gctttacagt  22740
attttggttt tgttagcttg tgttgcatct ctctctctac atttattatg tgttgatttt  22800
tgagttaaaa ctttgtttat gataaaccat gttgctttct ttggttaatt ttttttgctt  22860
aatgcttatt cccccactgt actgtcagga aggtccgcgg ctcacgcccg gctccacatg  22920
ctgctccagt gaggaaccca ccacagcctg gtaaagtgat tcacgcagac aataagtatc  22980
tttagaactg acattggcat ggtaatcatg cctcttttga ctctgcagta ttctattgtg  23040
gacatgtgtt tcaattatgt aactttagtt atatttttgt ataactgttt gctcagttgt  23100
tgagaatgtg ttcggtttgt tactataaca atgttgatga cataaatata ctgttaagtt  23160
tatattggaa tttgtggtac aagtctgaag ttgttgattg tgtttgaagc agagtcaatg  23220
gcatttcggt ttatatagag aattacagtt ccttgttttt tggtagaact ggaacctgtt  23280
tcagttctgt tcctaatgct tacacatggg tttgtgctac aagtatagta ttagtattac  23340
agagctcatt gttttggaat cttgattgct ttggaatcag aatcgtttat gtttagctca  23400
tattagtatt agtattacag ctcattgtgt ttatatagga gttttaatct gttctatttc  23460
tgttcctaag tgtcttctga cttttctttt tggcagcgcg ctaggctcgt cctccagctc  23520
ctgttcgtga tggtggtggt ggctccattc ttggaggaat tgggtccacc attgcttaag  23580
gtagttttca aagcttgttc ttttttgaat aacttcagca acaaacatta tcataatcct  23640
tgaattgatt tgaacgaaca cattgtttta ggtatgccat ttggtacgag tagtgccatg  23700
gcacacaggg ctgttgatgc tgtaatgggt ctccggactg ttcggcatga gattgttatc  23760
tcagaagctg ctgctgctgc ccctcctgct ccagtgatga acgctaatgc ttgcagcatc  23820
cattctaagg ctttccaaga tgtatgtctg cttgccacct ttatgctgcc ttgttttccc  23880
tcaatttgat gcatgaaaca tttggttact cacttctgtg atgtagtagt gaagttttat  23940
ggtgtctttt tttttccttt actgaacctg caaattactt aatcatcaaa ccttggccat  24000
caatcaagtt ttaatattat gggcatgatc ctaccgttgg ctttgttgag gtcatgttaa  24060
gaattgttaa cctgcatttt gtatactcat tcgatgatgt gttctcaccg attttcttgg  24120
ttgatgcagt gtcttaacaa ctatggcagt gagatcagca agtgccagtt ctaccttgac  24180
atgttgaacg agtgccgccg tggtgttgtc tgcctgagct tttgctccaa ttgggattat  24240
tcatggattc tcttttcact cccatgtatc tcattaataa gacaccgtga aacttttaac  24300
cctctccacg aatgcaccat ggcatcacgg gttcatcttg ttgaatctgt ggttacgttc  24360
tctttatcct gtgttgttgg aacagacttc tgtctcttct ggtgatcata aatatttaaa  24420
tgaaccagtt gtgttggaaa atgttgtttt cttttgtctc tagactggaa agcggagttc  24480
tcgtcaacac ggttctttca actagggatg aaagtggtaa tccgaattgt tagtacaaat  24540
```

```
ttaatatttt aaaatagata tgtataaaat tttatgttga tctttttttat gttatcaagc 24600
acattagtat aaattagtat aaatatgaat aaaatattac ataaaatgtt ttatgtatta 24660
tttggtccct acaacataaa tagttgaaaa aattactaaa tttgttttcg aatctatatc 24720
gaagtttata tctattattt aagaaaaata taggatgaaa aggtttatct tttatgaatc 24780
tttacaagct ggatcttata aacaagaaaa taaatttata ttgtagattt tatatcctat 24840
ttattcgcaa tcaaagaaaa gcgactaaaa aactgattac cgagtaaata ctgtttccaa 24900
ccgttttcgt ccctactatc aacgccttct cccaaccgca gtcgatctgt ccgtctgtat 24960
caggcgcagc ggcacccctg ctgttcgact atctagacca tagaatattt taggtataca 25020
ataattttag ttccacgcta gaacatttta gttagaataa taacaagatt tgctattgat 25080
gtaggactcg cccgtcactg tctaaaaaag cattctgtcg gtcttattct ttaggcatca 25140
gcgggtgtac tatctcattt ttcctatcat attcctcagt actctgttaa gtataaatgg 25200
tctattttac atgatgaact aataaaacta attaaggatc ctaacttttt gtgaaggtaa 25260
tttggatcat tatgcattac catcctacgt atacctgctg cagcagcatc tgcgtaagca 25320
cagcctagat atatgcttct gtgtggactg aaaggagact ttgtttatca attagtatac 25380
tcccaaaaaa ctgatgacac caatgatgca aataggctgg gaatagtctg tctaatagtt 25440
tgagtgaatc atgtcactgt gcgtcctctg caggcagttg ttgacatgag cgcatcgtca 25500
ctgctgaatc gccatggtct gaaggcaaca gataaggcat actgggcctt gtggtagttg 25560
ttttactggg cctttttgta tgatctataa aattcactgg gatcaacccg gagaggaatg 25620
gcagcagatg cagtccccag ggtcctccgt cgccgcctga gcacccggca cccgcgctga 25680
accggagagg gacgcgcgga cgccgtgcag ctggtgcgga gggggctgtg gcagatgagg 25740
atgagacgcg tacgtggctg ggaaggccag caggccaccg ggtcttcgtc cagcccggcg 25800
cgagtggaca ggactagaga tggcaacggt tacaaacccg ctgggtttta ccgtcccaaa 25860
cccgtacccg tgaaaaatat ctatgcccat taaaaaaccc gtacccatga cgggtttgag 25920
attttgccca aacccgtacc catcgggtta acgggtaccc atgggttacc cgcgggtttc 25980
atctccaata tacctgttct tctcataatc aataagtatc gtaatgatta atgatatcat 26040
gatccaaaat ctatgtaatg aacaacgagt tcatgatttg gtataaaaat tattagtaga 26100
gagaatgaaa tacaaataat aagttgtata attaagtgac cttgcactaa gttatccatc 26160
catcacatat ataacgctag taaaaactat aatatcaagc aagcaacact ctcaccgact 26220
actgatacat tcaccaattg ataaaaaata tgaagtaaat aaggaataac aagtttgttg 26280
ttcgtttata aaataaaatg acaatatgca ctaggtttgg tcgggtttaa aaaacccacg 26340
ggttcacggg tttgggtact ataggaacaa acccgtaccc ataaacccat tgggtacaga 26400
tttatgcccg ttaacaaacc catgggtatg aaaattgacc caaacctata ccctaatggg 26460
gtaaaaaccc atcgggtttc ggatttcggg tacccattgc catctctaga caggacaacc 26520
tcggccggtc ctgtatgtag gccaccagca tcggccagtt ggtacatcca gccggggtca 26580
ggtcactttt actcgtctca atcagacaat caccgtccac caacgaacgc caacgttgtc 26640
acttgtcagg tcggttgaga cttgtatttt tttttgtcct ccgtaaaaat cagttccaac 26700
gacagatacc ccgacggtaa gcggacagcg ctgtcgtagt cgttttgttt gagtccacaa 26760
atgagccgaa gatgcaagca gcatatgcaa cgtgtgttac aaagaaaaga agtggatgca 26820
aaggcactac gagaatgaac tggtgccacg gaaagatgga accaaaccaa cgaactattt 26880
tttccctcct ttttttatt aatgcttcgg acgacgatag cagtttctgt acaactcttg 26940
```

```
atatataaaa aacaaacaat atgacggatt aacctaggca tccaatgccc ccccaatttc  27000
ctcctgctat agcgccacac cttgctgctg cgacgactgg agccttccct tgaggaagcc  27060
cctgcacacc ttgctccaca gctccttgtc cggctgccgc acgtcgaagc tcgtcttggc  27120
cacttccacc tggcagtcct gccaacaaca aacaaaacaa ggacagatat tttttttgt  27180
cctccgtaaa aatcagctcc aacgacagat accccgacgg taagcggaca gcgctgtcgt  27240
agtcgtttag tttgagtcca caaatgagcc gaagatgaaa gcagcatatg caaggtgtgt  27300
taaaaagaaa agaagtggat gcaaaggcac tacgagaatg aactggtgcc acggaaagat  27360
ggaaccaaac caacgaacaa tttttccct cctttttttt tattaatgct tcggacgaag  27420
atagcagttt ctgtacaact cttgagttct gaagcacata taataaaaaa caaacaatat  27480
gacggattaa cctaggcatc caatgccccc caatttcctc ctgctatagc gccacacctt  27540
gctgctgcga cgactggagc cttcccttga ggaagcccct gcacaccttg ctccacagct  27600
ccttgtccgg ctgccgcacg tcgaagctcg tcttggccac ttccacctgg cagtcctgcc  27660
aacaacaaac aaaacaagga cagatatttt ttttccatgt cacagacaga cagacagaca  27720
gacagacaga gagacaaacg aacactcggc acgctgtcgt tactattatg attaattacc  27780
agtatgtggt tgtggcggag gaggcggtcg gcgatgctca tgaggacgtc cttgctgtac  27840
tccgggtggc cctggacgcc catggcgcgg ccgccgaggc ggaacatctc gacgcgggtc  27900
ttgtcggacc gcgccagcgc ctcggcgccg gggggcagct cccacacctc gtcctggtgg  27960
aactcgatca ccggcatgtg cacgggcagc ttcagcggcg cgaacagccg cgccgccgcc  28020
gccgtcgggt ggatgcagct caccccgatg tcccagccct tggccgaccg ccccgtgcgc  28080
ccgcccagcg cccggcacag gatctgcgtg ccgcaatcaa acagcttcag gagttaagac  28140
ggaagtgtag tagccacagg agtttagagg tacgtgtgcg taacgtggac gcgtgcaagt  28200
ctgcctggca tcggcgcccc accaccgaca gggccgatgg acgcaactaa aacgttttct  28260
tcgggaacac gccaagtaat tgattcatgt gcacacagac tgtccccctt ctgtttgtag  28320
tacgatattg ggaacctcct aggattccac tgctaaacaa ttggtgtctc ctgttcctgc  28380
gtacgagtac gacgacggaa gacttcgcgg ccacaagagc aatccaaatc caaggctctg  28440
gctctcggac cacagggaca gcgacagtgt aagagctctt tgaagttgcg agtgttatta  28500
acatagaacc aagtaataat taggagaaga ggtcagtacg tcctcacgcg tcgaggcacg  28560
tctctgacaa aagcgtggtt cgcgcgggcg attgcgtgcg cttgggcttg ggcgctaccc  28620
gcacgccctt gggcgtgatc tgatccccctg agctgctggg ttggtacgct agtagcatcg  28680
tcatcccaaa agcaatctcg ctcggcaggc gagatgcgtc acgccatttg cgttcttcgt  28740
cctcctcctc cttcccgggg gatttgattt taaaatttgc aggcgcggtt tacgcgccac  28800
tttgaggcaa acaaaccggc gaaccggaat aggggaaccg ctcgctcctc taagccaggg  28860
caggggcgca gggctctgtg actgtgagcc aaacgtccgg ccacagacgc agcgggccgt  28920
aggagatcct gcagaacaga tacccactcc acttgtctgt gtgccaacaa caacagcaac  28980
ccagctgcca cggccacgtc acaccacgtg aatcagcgat gtcagcctcg agccttaacc  29040
ctttgtttga gagatgctgc cgtgtcttaa acctagatta gcgtggagtt tgtagtcact  29100
aatccatcca atcagtcccg tgtccgtctg tttgcttcga cccgaatcaa accaggggcc  29160
tctgcttcta tgaactgaac tggcatggac tgaaacaaaa cagcgtcatg gcagaagcaa  29220
gagctctata ttgtgcgctc taaatggaga ttggtaaaac tcgtagaatt gggggttcgt  29280
ttcttccgtc aaactctaac tgtgggcttg atgctagcac tgagtcacct ttgtcattct  29340
```

-continued

```
ctggggaaaa aaaataaggc atctttccgt ccccattgct actgctcacc aattaagcag  29400
ccagtaccgt ttgtactagt caaaatgcat caagaacgac cacgggtcgc cgtaaaaaaa  29460
aagaaagaaa ataatagaaa agaaaaggtg cgccgggtgg acgggaaggc gctaggctag  29520
aagagcggca gccccaccag gtggtgcccg cagcgtcccg cggtcccgtg attcaccagc  29580
gacgacggag aaacccagct acgcgcggaa gggactagac gagaaccaac cgcaccgcac  29640
ctaaacccaa ccaaacagca agtcgaacca aacatggacg gatgggatgg gcacctggtg  29700
gccgaagcag acgccgagga cgcgcttgcc ggcggcgtgg acgcggcggg tgaggtcgac  29760
gagcgcgagg atccagggct cgtcgccgtg cgcgtcggcg cagctcccgg agatgacgaa  29820
cccgtcgaac ccggctgcct cggcgtcggc ggggagctcc ccgcggacgg cgctgtacac  29880
ccgccacctc tcgccgtcct cctccagcag cgcgcggaag acggcgaagt agccgccgta  29940
cttctgccgc acgtactccg agtcctcgcc gcactgcagc accgcgtacg agcccgcccg  30000
cgaggggggcg gcggcggcgg cggcggcggc ctccagcgcg gccgacgcgg cgttgtcgag  30060
cggccccatt cccatggctg gcggcgtcgc ggccaggcag gcgcgtctcc ggcccgggaa  30120
tggaggcggg ggttgggcgt cgcttggctt ggctgactcg cttgcggggg gtgagaggtg  30180
gcggggagga tggggggaga acggcgaggc gaggcgaggg cgatatttaa agtaagcacg  30240
agcggttttc cctcggattt tttttatttt ttcgtcgctg gttttccatt ttgctattat  30300
agtactgttt ctgttttttt ttactggtac tggggctggc cgctaccggc ctaccgctaa  30360
catttggtat ggacgtatgg catggcaacg gccagcaggc gcgggacggg ggctaccggc  30420
gagcggcggt tttgctcggg tccccttcac tgctcgggtc tttggccggg tcctagtaat  30480
gggtacccaa aatcgggtat ccgatagata aaaatcctat tagagcatgg atgtagcgaa  30540
ttttaatatc tatggatatt ttattaggtc atttattaaa tttcactcgc tcatgcatac  30600
aatatactta acaagcaaag aagacaaacg tggacccctt aatctcacct ttaaaacata  30660
tattgataaa agagtttttt tttctagacc gatcttgtca aatactgtat ctacctgcct  30720
gataaaagat tcaaacagga agagcaaaag cgtatatcaa attaattgac acgggagtcc  30780
atttctgtgc tcagagtaag cgagccctac aattgcaaaa aaaagggggg gggggggggt  30840
atgcatatgt aatatctgat gtcatttata tatagtgcaa cgattctctt tcgtaccaag  30900
ttgcaagtcc tcatatcgaa tcgtaagtta ttctgttttc ctgtgtacat atgaacatat  30960
ctatctttta atacaaacag catttttat agtttttct aagtacatat gaacatatat  31020
ctatcttcta atacaaacaa catattttt gtatagtttt tgttatgatc atatgttttc  31080
ccatgctacc gtttgtatta aaacacggaa actaaactac actaatttat tttattcata  31140
tttctttctt taaaaaaatg ttttttatcg ttccatcctc tctatttcaa accgtaagct  31200
gttctggctt tttttttcta aatgcgtatt ttagttatat ttctagatat aattagagtg  31260
tacataaaca cataaaaacc cacttactaa aatcacaaca acttacagca atttaaaacc  31320
gtgagattgc cgagcagggc gagaaccgac tgttagacat gctcacatgc atgtctgggg  31380
cattgtttga ttttatttgc ccgagaaatt gctctgtttt cattcgtaga atttgtacta  31440
gtattttctt accgaggctg gctgggcata cgtgcacgcg cgcgatcgtg cagcgacatg  31500
cacatgcaat gcaatcaccg cgtgacggag taccgaggcg aggtcgtcga ccacgtgccg  31560
tatgggccgc tggcacgtga caccaccgat tcggatcctt atttattcat tcatttgtca  31620
gtccccacgc attgtattta aaaattcaga aacgtaagcc cacttttacg caaaaacaac  31680
tttactgtcc gaaacgcctt gtgcaactag ctaggctagg aggctaactc attagtaaaa  31740
```

```
tgttgtgttt tccacccttc ctttgtacta attttataga ctattagccc ggacgagctg  31800
gctaggccag acagggaaat tatattttac tttgacgcct catctggatc attggaattg  31860
aattccattc taacaatatt aatttaggta tatatcaatt aagctaatcc ggttttatgc  31920
aaaatatatt tatatactat tattagcaag atgtcggaga tatttatgtg ctacattttt  31980
actataaagg agtgaaacga agagtgtcat gtaaattaca gactagaaac gaattctact  32040
aatgcataaa atcatttcac acactccacc ccatgaattt gagatagcct tatatctgaa  32100
ctttggaaag tggtggaatg tcaaattcca aactaaataa gttattttat tgagtgaatt  32160
ccaattcctc taaaatgaag ggatccaaat gccccgtgac tggaatttgg agacgaagcg  32220
cgcgcagaat attcgggtca aatagaatca gctacatact atgtgcatta gggctcacat  32280
aaataatcca tatcttgagg agtatcaaga gagtaagtgt aaaaaaaata caagagacat  32340
atcttgatga agagatgtat ctagctcagt tctctaagtc tagatacagt ttcgtccata  32400
caacccacat aaatgagtta tatcatgaga gattctagtg aataagatat atgattatat  32460
acaaaaatag tttcttatat gtttttttgt attttgaaaa ccgaactgga gtcttaaggt  32520
tgcacatgcc ctggatgtat ctagtgtttg taaaacctgt ttgtaaaacc gcaacaaagt  32580
ttctacattg tacatgccct tagggatgtt accaattttg gtagtgaaac gcaataatga  32640
attaagcaat aattcaagcg gatcagaatt aaatgagacg tgtggtgtag actgtagaga  32700
gtactctacg atatgtagtg ggatacttgg agcagtaatt attactaaac atgaggtgta  32760
gtaaacattg acgggataac gctgcacatt aaatactagt atcagtaaac gatgcaatat  32820
gcacgatcat ggtccgagag aatattcgga tcaacacatc tatctcctgc gtttatatat  32880
tattaaaact gaacgttacc gtttttttgtt agtagtgata aagatcgatt aaggtaactc  32940
cagcaacgtt ggatgtgtat aacactgttt tgtattgtag atgtactctt tttatataag  33000
gagaagttta aaatagaaat tacgataacg taaagtgggt ttttaccggc taaatttgaa  33060
cgttttccct ttccttccct ggtcctgtac ttgcagtatt gcactgtcgc ctgtcggttc  33120
atcgatcgga acgacgacgt cgtcgcgcgc ggcactatgg gcactagtac tttggtggca  33180
gtggcacacg ttcgtagtgt gtgtcacttt ggtgtctgga gcctgctgga gcaagacagc  33240
aagtcaggct gaggccggct actcagctgg gcgagtgggt gttgctgcga gctttggcgg  33300
atatcagggt atgcatatat ggcaacggct ccaaaaacgc gctgctgcga ctgcgatgcc  33360
ctgcagcatt gcaatggctg gccggccggt gcgcgttgct tggaagaaag atgctgtccg  33420
gtcggcgaac cagcctcgat cagccatgcg gttgtgatgc atgcgcatgc ttaacagtct  33480
ggaccctaac acgggctggg tgaagctgaa gaggacctaa tttttggtag ttttgtttga  33540
ctgaattatt ggtagttaag ctagattagt cctacttttg ggccggggct ggctttctgg  33600
cctagctcaa cacataattg tttttttttc tccatacgga cggcgtacat gcgttcaaat  33660
tttaaacctt gacctttttac ttttattcac gtacggtgta ctgaacccgc cgtagtccgg  33720
tagaaaaaag tttaaaaatg agagacacga cctcatgtta accgtcaccc gtgcatcatc  33780
gatggacgta cgttgacagc atcacaacga ctacaaaaat atcaaataat gcatgttaat  33840
ctgattctta gtatagcctt tcggtgtcgg caaattgcaa tgccgtgtgc cactatgttc  33900
attctcaaaa aaactgacca attgacgccg gactaatgct ggatcaacaa cgaccgcaca  33960
agtcgtgata gtaacggtct agctagtttt cacttttcag agattaattt agagacagct  34020
agctagctca ttagttagtt agcaaattag ctagttattt gttagttagc taatttcact  34080
aatatttttt agccaactaa ctatatatat cttcagtgca ttcaaacagt ccctatataa  34140
```

```
tctagattaa tttagttgta gctatttggc atcctagatt aatggaactc agattttcat  34200
cattagacaa cactgtccac ggtcgtattt cttcattatt tatgatactg tagcagtttg  34260
taggtacata aaaacgttga acatgttcaa acacattaaa aataaatatt tcatacacat  34320
tttgtgccca tatcatacta catttgaaat taaattacat tcttctcgca aataatacat  34380
tgacaatttt atctagaaaa gtattcgcgg ttccctcttc atctcccaat ccggtatcgt  34440
gatgacttga tggtatttaa tcgttgtcgt cttcatcaca tcaatcaaat agttcttccc  34500
gtatatgtta ctacctcaaa tgaaaaaatt attccttcaa cattggataa cttggtaagt  34560
ccaataaaat tatgaatttc atcttcgaga cagcgaaaga ttgctcaata tgataagtgc  34620
aattggttga atacatctca tcatcacatg tcagtcaatt aattagtcga tcaacgatga  34680
aaattaagcc ctgaggttca ccgtgctaca aaacgacatg attgtgtgta cagttttcgt  34740
actatttaag ttttacctcc ttcctatatg aaacataatt cctcaacgat tgtttgcttc  34800
ggattaaagc ggactattta gattggtgta ggtgtaatct ataaaaacaa aagtactata  34860
gaaccagtag aaaccggtat agattaaagt caagggaacg actgaaagtc cacaaagcta  34920
ctggattcca tgagcttctg tagataacaa gcccgacatg gcgacgtcca catgggccgg  34980
gtctgaaaat tcccttccca gcaaataaag agaaactagc aaattgttca tatatgctac  35040
ggttctattt atacttatgt atagaatata aaatataaag atatgagtgt attgttagtt  35100
atgtggatat gaatgtgagt ttagagctaa taatcatagt tcgaatctct atttgtatat  35160
aattttagca tttttataat ttaaatgtga ggtatacgat gaaaatcata aaactaggaa  35220
aattagtgtt ttaatatagt acagatatta ttctctgaac caaagacaca caccagaata  35280
caactcacat atgcattgca cgtgtgaagc tccgacacac agggcgcaac aactcagctg  35340
ctttctttac gtgatcagat tgctagagta cttcacaaag ggacgccgag agagtatcgt  35400
tcaccaacct ggcagtggca gttgccgcat tgtactagtg tacaaaagcc cagctgaacg  35460
gtgatcagtg gcctcccaat gccattctgt gtaggcgatc acagatctat caacaccacc  35520
aaacccaagc cagcacactg caaaacacca aaaggattga agcaagctgc caaatggcac  35580
gcgttgcagg aacaccgacc ctgcctgatt cagagtcaga aatgcaatta tagacgagtc  35640
tatgggcatt gtcactgaca gaatgacagg gcaaagatac cacagtttca cgcgaaaaca  35700
tggccgtggc acgttggccg ctcgaggcaa caacttctat attggcatag ccagaatgat  35760
aatattgttg tacaactcag ttagagatcg agtcgcacga tcatgctcgc actctctgat  35820
tagggacgta acaatctgtt ggttaataag ttctcctttc ataccacata ataaatagtc  35880
aaagaaccga tacgcgaacc aacattcata ccgagattcg atctaatatc taccggccat  35940
cttttcgact ccccgaacca tagccggagt ggccatgggc atttctccgc ccttgatcag  36000
catggcatct ccttccaatt ctggaggtac aaatctatgt tctatgattt ctaatggcta  36060
ggattacgag tcgaggtctt aaaatctaat agtggtatca aagccatggt tttaggctcg  36120
ggctctaact ataaatgaca gttttcctta agttttatga caaaatccga gaaaaacacc  36180
tcttaactct ttgtattcgt gttcctactc acgtagaaca agcaaaaggg gagaaagaaa  36240
ctctaaccca acatttccac ctttcccaaa ctctaatcct aaggcagtcc ataatctgag  36300
cacccaagca cacaaagaaa gggaaagcag acgttaggaa agcagccatg tgctatatat  36360
tcgaagacct agcctacaca cacatctgtg aaactgtatt aaattgttaa atatttttag  36420
tttgttaaat atttttaaat tacgttaact cgtcttttct agttattact tatagcttca  36480
aatctagttt catttacgat aaagttcaat aatcattatc cttctcttga ttactatttt  36540
```

```
catttggtat gaatcatgat cggttgtttt tctctaaatg tttgggtgag taatctttag  36600
gcttgacaaa cgaggatggt gaattcattt tttacgcatc tcatattatt taaagtgcat  36660
cacttgtaca cgagcacaaa ctcgatggca tgtaagtgat tttagggtgt gattgacaca  36720
caaaataggc tattgggagt gacaaacaac tcctcaagtc taaggactaa ataagaatat  36780
ttagaaaatt agtatatttg gatatctcat ttaaaaaccc attgaagctt gatttttggt  36840
taataacatc ctacattatt tttagggcct gttttgggaa ctagagatgt tctaagggct  36900
accactcaat tggataccta attagttgtt gactaatctt gattagttgg atgacagaaa  36960
atagaatgga actaggtaac taagggggtg ttggattaca ctagagataa tagttagctg  37020
ctaaaattag ctgaagacat ccaaacactt tagctaatag ttaaactatt agctattttt  37080
agcaaattag ctaatactcc ctccgatttt tttatttgac gtttgttagt gaaaatctga  37140
actattgagt gtcaaataaa taaaaatgga ggtagtagtt aggtagacat ttgttaggta  37200
gctaattaca ctaacaatgt ttagccaact aactattagt tctagtgcat taaaacatcc  37260
tctgaggtga tgacctgcat gtggtatgac ttaagtcact tggcctcatt agcctaattt  37320
gcaactctac atgcagccat cgtcctagag ttaattggtc actagttagt tgctaactgg  37380
tcatagttag ttgtccgtgt gtgctagggt ttctttatac catatagata ggctttatcg  37440
aaaaaagata tttatttaaa cacgatctaa actcatagat tctcatatcg cacaattata  37500
tttttttatt tttaaattat ttgtatatat atttacaata tcaattctta ggcacaaatg  37560
aacatgtggt atactggtta gagactcttt gttttgtctc tcactgagtg agcaggattt  37620
gaaccctcat aggctgcgtt ggacgcacgg ccgcgagagt tagacgatcc acgataaaac  37680
tcatgtttta agggtgtgtt tggttgtaat gatgggaatg agacagaatg aaatgtgatg  37740
atcctcaaat aaggttgttt agtttagggt caagggttgg aacaagactg tcccagtatt  37800
gtcccagtta tccctcgaaa ttagagagac gagaggggac gcgaggaaac gtctctgacc  37860
tggctatccc tatgtgtacc gcaaccaaac gcaccataaa ttaatgatga tgatgcttat  37920
tgttgttgaa agggttgcaa ccttaactac agcactaacc gccttatcca aggatcaaac  37980
acaaaaggcc aaacctgtga agatttactg ttgtattaca taattacaag attaccctgg  38040
aatgtttcgc atgtctgtaa accgaagaaa aatagttggt tccaaacatc ccaggtacta  38100
gcctgtgtgc accttggcgc gcagaggctg gagttgattt ttcctttatc gaaaaggaaa  38160
tatttctaag cctctaacca tttttgcatt ctatgcagtg tcacctcatc agagagttaa  38220
tagttaatca agcctcccaa aaccttcatt tattaatgag ccagtgaaac tacatgatac  38280
catcatagta agaagttcca tgagtaacag gtcagcagat tcatttttca tttgtgaaac  38340
tagattaaac aaaatattcc tttgggttga agtttttttt gtctatttga cttttgggtt  38400
gtaacatgaa caaaaatata ccacctgcaa ctgaaacatt caaagattca aaggtacctt  38460
cctttggaat gtttacaagc tcaaatgcct ggagggtctc tgcagtgagg ccattgccct  38520
cacttcctaa cactaagcac agagattcat tcaacatcga atcagctagt tctttggaca  38580
gcgagtagat ttttttggat gcagcactac tactttctgg atggcctgcc atcatcttca  38640
taccatactt tgtcatcaat gcatgcaggt catgccaggt accagagaca ataggaagct  38700
gcaaaggggc tccacgggct gcacgaacag cctttccatt gaaaggacca caacaagccg  38760
gaagaaggaa tactccatcc tgatggcatt tgggttcaga ggttgttaag aggtgtagag  38820
ttggaacagc aaaaactaga gtgtttggtt ttctctattg gagattgtta gtttctatgg  38880
tgcctaagat cgattcctaa gtccctaata ctaatccgta acagaaagta aaacctcgat  38940
```

```
gacgagtaga tctgatctac tgagatcaat agggaaacac acttttgttg ttgttgttgg  39000
agcgttgtcg cagttgccgt cttcataccg ttgccctgca gagaagcagc aggcatcgga  39060
ttcgagccgc tgtgggttgt agcgtttcca ggcactccga cgcttaggtg atggggcctc  39120
tggggactag ggttttgggg cgaggtacta gtgttagtct ttcctgcgac ctttagtcct  39180
atatttatag cgttgtgtgc ccggaggctc caaccgaggt taacgtggcc cctctcaatc  39240
aagggtccgt ttaaggagat agatagttgg gattagccca atctgatcac tgatgaccag  39300
ctatagagga cacacccaac agagataact aatacatata aatcatgtat tgtgtatcct  39360
ataaaaaata ttgtgtaccg gaatcagaga taaggaggta aggacatcca tcctatctta  39420
cttaagagca gaatcaaatt ctttttagca aaggagaact ggagcacaat gaaatttagt  39480
ggcattcctc aaattctatg gtagagtagc aagattattt aacactatgc aatgcagcaa  39540
taatacagtc tgacatactt caataagcgg ccttcagaaa agaatatggc atacccattt  39600
gaaagcacaa gctgatctta tcagtgttcc gaggttacca gggtcctgca aggtaggggc  39660
accagtgcac catgcttacc atgagaccca ctgaacggat atgcataact acatttgctt  39720
caaacaaaaa cagcatgcat agattgaatt atgccttgca ttctactccg tccgttcttt  39780
tttatttgtc acggtttatt agtttagttc aaaaatgaac tagcgggcga caaatattcg  39840
agaatggata tagtattatt taaggatgac agcaatcatc tctctgcaca atggtggcct  39900
tgatgggtac tgcatatcct cacctgaatc ccatcaagga ctagaatcct ctttggacaa  39960
ctgaacaacc catcaagagc atcccatcct catggctcct gaggtcgcgg aaatggttag  40020
gcatgtgcat gacagcaatc gcctcggtgg aatcagccga ttgcatcccg gacaccttct  40080
tcatcaccgc gtcgctgcaa tacacgacat taaaggactc gcgcagcacc tccgggacct  40140
aggataagca agtaatcgat gacaaggggt agaagcacag gtttaggaag agaagaaacc  40200
tcgcaggaca tgtaaatatg acaagggcct ggagttgcag aggagtacag gatgggcacg  40260
aggccgacaa aatttgacca tcacatttgg tatgtttggt taactttcgc atcatatagg  40320
ataggagtat aggactagga tccatttcaa attatcgtgc atttcataat ggtttctgaa  40380
gctttggtca ccaagtattc ctatttctcg gctggaattt cacgtttgcg ctgcgaggga  40440
gtgtttcgtc ttcgactctt cgttcagaca gaccccgcgc ggactggagc caagccgctg  40500
ctacctgccg cacgctgcca ctgtcaggtc cgctcggcac atagcgacac agcgagcgca  40560
aacatttcgt tcgcactggt ttagcaaccg aaacgctcct ctatctaatc tcttatatca  40620
tcccctattt catacttatc tctacaaaca gtgttatata tagttccacg tcatatattt  40680
tccactctac tagaaacatg tttgattcgc ccctgactgt gccacaattt acaatttatc  40740
taaggttagt aaaaaaaagt tagataaagt atgataagat ggcgaactaa atatacccta  40800
gcgacacaac agcttggaac aacttcaacc agccctagtt agccactcgt agcttcatgg  40860
taaagatttt ggataatttt ttacaagttt acacacttca tcacgacaaa gattgtgaat  40920
gctggatgtt tttggatttt gacaccttta cacacttcat aacgtgtgcc atctattaga  40980
ggagaaacga gaactgcacg cagcaacgca ccaggctaat aagtgacaac cgaacaagga  41040
aaggcgggaa gggggcaacc tggaaaatag agagcagagc agaactttat tcctcctctc  41100
aggaagtgtc cttgtcactc taaacgctaa cagccgaagg aaagaaggct gagagtgaga  41160
tttggagcca caaaaagata accggcatac tcagaactac atgggtccaa atttgagatg  41220
gtattcaaat tttagatggc aaggtctctt aggcacagct cattcgtctc ccattgcaag  41280
ttctagcgcg taatcatctc tttcctgaaa aacaaggagt ccattttatc tcagtgaagt  41340
```

```
gtctaataac ctataatcac actttgcaga tcagaaagta ttgttactca ccactggccc  41400
tcgtgcaaag tatctcccga attggagcca atatacctgc aaattgacaa acaacatgct  41460
ttgaagagcg aatttcctac tacatataga gctagatatt aattaatttc aaaaggtgtt  41520
ttagactacg tgcttgcctc atcttcatct tgagtctcga cttcaacatc gccagatggg  41580
aaaccaacac acaacaaagc atagccctga aaaggaaacc atacaataga actctaaaat  41640
ccttaagtac catacttgat aggcaacatc ggacaatgct cctttccact ttagctatga  41700
atttggattt atccgaattt atagctaagt gtctactatt ttaggacgaa gatagtactt  41760
tataattggt agctaatttg tattgatgaa catttctatg ttgcttggcc aagaataact  41820
gatcaataaa aaaatctatt gtcatatctg taacacaaaa aatacaaaat aaattgtggg  41880
tcacattgca atcataatcc ttccttaaaa gtcgacataa tagttatgca tcaaactcta  41940
gcaattgccc aggaacattc aggaaattgt acaaactagg taactgacta aactggagga  42000
caggttaaga gtgaaataca acctctcatt tccagaccat gtacacaggg aacaataata  42060
tgtcatgggc acaatactcc aatcgtgctt caactagtgg aagaaaaaat ggatgtacct  42120
tatcttttag ttctgcagat atcccaagtg cttcaggctg ccttatctgt cctgatttta  42180
ttcggactgc acagcttgtg cagcaacctg attaccaaaa tgagttttca attgttatat  42240
agaccacacg gaacaatcaa ataagagatg ctatccaatc aaaaggtatt catagttaaa  42300
taatatatca aaagccaatg gcatgggtag tttttttttt aatttatagt tgctataagt  42360
atttgacaaa tagaaagagt cccaaatgag tccaacatgg ttctgactac atattccaaa  42420
atcaaaacca acatcacact cccacacgat actatctata tcaacataaa ggaggatgag  42480
aaatagccaa cattcagttt gcacatattg gagcagctag tggtggagct tggccataaa  42540
aagaggacgg accattatga tatgaagtgt aaagagaagg gagacagatt agtatttcat  42600
cagttccgcc actcaagaca gggcttcatc aggctctatt tgtaacaaat gaagacggtt  42660
caagctgaag ggtgacattc atgcttagca cttagtgtag ctgctactaa ctaggcatgc  42720
ataatgagtc gcccaatagc ttactgtcat gtacggccgc acttacaggc gccgtcgtga  42780
cgccaggagg gctgcagatc gcgcagccaa ggcaggcgcc acaatcagtg gctaagttta  42840
gaaagataag gattagtttc cctcttgcat gccttaatca taggagggat tggttacgat  42900
tagtttcctt ttcatatgcc ttaataatag gagagattgg ttaagattag tttccttttc  42960
atatgcctta atcataggaa aggttggttg aaccagaggc tatatatatg ccgtgtaata  43020
ggctgggaaa taatcaagca agatcaatta tccaaaactg ctcttctcct ttgcctctct  43080
caagccaccg gtgaggaatc cctcacggtg aaggtctaga gcgcgactac gaactgcgta  43140
gccgcggtcc agcgacgttg ggcgtcgagg cgcttgacaa cctggtatca gcgtcacgtc  43200
gatcctcacc cacccgctct tgccctccac catccccttc cacgcccacc acctccaccg  43260
accactccat caccatggct gagcccacca tcaaggacct catggagctg atgcagtctt  43320
tccaaaccga gttggctgcc gtgaaagcca ccatgaagga caagtcgtcc tcgtcgtcca  43380
ccgacggcgg cggcgagcgc gaggatcccc ctcgtgtgga tcggcccccc aggttccaga  43440
agctcgactt tccccggttc gatggcacca ccgacccgat gctcttcatc aacaaatgtg  43500
aatcctattt tcgccaacag cgcaccatgg cggaggaacg cgtgtggatg gcctcttata  43560
atctggagga cgtcgcgcag ctgtggttca tccagctgca ggacgacgag ggcacaccat  43620
cctgggggcg gttcaaggac ctcctcaatc ttcgcttcgg gccaccactc tgctcagcgc  43680
ccctgttcga gttggcggag tgtcgccgca ccgggaccgt ggaggaatac tccaaccggt  43740
```

```
tccaggccct gctgccgcgc gcgggtcgcc tcacggaggg ccagcgtgtc caactctaca  43800
caggcggtct ccttccccca ttgagccacg ttgttcgcat ccacaacccg gagacacttg  43860
atggggccat gagtctcgcc cgtcaagccg agcagctgga gttggcacgg ggaccgccac  43920
cggccgccag gggagcccct cgctctcttc ccccagcgcc ggcgcccaag cagccgctgc  43980
tcgccctccc tgcaccaccc gcgggcgcgc cccagccgcg accagagggt ccgcccttga  44040
agcggctatc accggaggaa caggcggaac ggcgccgcct cggcctctgc ttcaactgca  44100
atgagccgta caaccgcggc cacaaccgtg tctgccgccg catcttctac ctccatggcg  44160
tcgagctcac ggccgctgcc gaggaactcg taggggacga cccgcaggac ggcgcccctg  44220
tcttctccct cagggcagtc actggcatgc ccatctgcaa ttccatgcag gtgcgggcca  44280
ccctaggcgc caccaccctc ctcgcgctcc tggacaccgg ctccacgcat aacttcattg  44340
gggaggatgc cgcccgccgc accggcctgc cgatccagcc gcacctcacg gccactgtgg  44400
ccaacggtga acgtgtcacc tgcccaggag tcattcgccg cgcccaggtc atcatcgagg  44460
gcgagccatt cttcatcgac ctcttcgtca tgccgctcgc agggtacgac ctcgtcctag  44520
ggactcaatg gatggtcacc cttggtcgca tggtgtggga cttcgtcgac cgctccgtct  44580
ccttcctgca ccaaggtcgc caggtctcct ggtcggacgt cgccgaccgt cagcatcccc  44640
tgctcgccgc taccacgaca ccgagcgccc tccttgagga gctcttgcac tccttcgacg  44700
gggtgtttgc tgagccggcg ggtctgcccc cacagcgagc tcgggaccac gccatcgtcc  44760
tcaagccagg ctctacacct gtggcggtcc ggccgtaccg ctacccggtg gcgcacaagg  44820
atgagttgga gcggcaatgt gccgccatgt tgacccaagg catcgtacac cgcagtgact  44880
cggcgttctc ctcaccggtt ctgctggtca agaagcacga cggggcttgg cggttttgcg  44940
tggactaccg cgcccttaat gccctcaccg tcaaagacgc cttccccatc cccatcgtcg  45000
acgagctcct tgacgagctg catggtgcgc agttcttcac gaagctggac cttcgctccg  45060
gtgatagtcg cctagagggg gggtgaatag ggcgaaactg aaatttacaa atataaacac  45120
aactacaaga cggggttagc gttaggaata agaaacgagt ccgcaagaga gggcgcaaaa  45180
caaatcccaa gcgaataagc aagtgagaca cggagatttg ttttaccgag gttcggttct  45240
ctcaaaccta ctccccgttg aggaggccac aaaggcctgg tctctttcaa cccttccctc  45300
tctcaaacga tccacggatc gagtgagctt tctcttctca atcacttgga acacaaagtt  45360
cccacaagga ccaccacaag attggtgttt cttgccttaa ttacaagtga gtttgattgc  45420
aaagaaggat caagaaagaa gaaagcaatc caagcgcaag agctcgaaag aacacgagta  45480
aatcactctc tctagtcact atggcgttgt gtggaatttg gagaggattt gatctctttg  45540
gcgtgtctag aattgaatgc tagagctctt gtagtagttg ggaagtggaa aacttggatg  45600
caatgaatgg tggggtggtt ggggtattta tagcctcaac caccaaaagt ggccgttgga  45660
aggctgtctg ttcgatggcg caccggacag tccggtgcac accggacagt ccggtgcccc  45720
ctgccacgtc atcactgtcg ttggattctg accgttggag cttctgactt gtgggcccgc  45780
ctgggtgtcc ggtgcacacc ggacaggtac tgtttgctgt ccggtgtgcc agcatgggcg  45840
tttctgactc ctgcgcgcgc agagcgcgca ttaaatgcgc ggcagagagc cgttggcgcg  45900
gagaagaccg ttgctccgga gacgcaccgg acagtccggt gaattatagt ggactagccg  45960
ttggggtttc ccgaagctgg cgagttcctg aggccgacct cctttggcgc accggacact  46020
gtccggtgta caccggacag tccggtgaat tatagcgcga gtgcctctgg aaattcccga  46080
aggtggcgag tttgagtctg agtccccctg gtgcaccgga cagtccggtg cgccagacca  46140
```

```
ggggtgcctt cggttgcccc tttgctcttt tgttgaatcc aaaactgggt ctttttattg  46200
gctgagtgtg aaccttttac acctgtgtaa tctatacact tgggcaaact agttagtcca  46260
attatttgtg ttgggcaatt caaccaccaa aattaattag ggactaggtg taagcctaat  46320
tccctttcaa tctccccctt tttggtgatt gatgccaaca caaaccaaag caaatataga  46380
agtgcataat tgaactagtt tgcataatgt aagagtaaag gttgcttgga attgagccaa  46440
tgtaaatact tacaagatat gcagggattg tttctttctt atatattatt ttggaccacg  46500
cttgcaccac atgttttgtt tttgcaaatt ctttttgtaa atccatttca aagatctttt  46560
gcaaatggtc aaaggtaaat gaataagagt ttgcaaagca ttttcaagat ttgaaatttt  46620
ctccccctgt ttcaaatgct tttcctttga ctaaacaaaa ctccccctaa aagagatcct  46680
cctcttagtg ttcaagaggg ttttgatata tcatttttga aatactactt tctccccctt  46740
ttgaacacaa taggatacca attgataaat actcttggaa aacactaagt ttttgaaatt  46800
ggttgtggtg cggtcctttt tgctttgggc tcatactttc tccccctttg gcatgaatcg  46860
ccaaaaacgg aatcattaga gcctatcgaa gtactatcgt cccctttggt cataagtaaa  46920
tgagttaaga ttataccaaa gacgaaatcc ggtcttttag ctttgggttc ttactctctc  46980
cccaaagaca aggtccttta ttggagcgat ggcgaaggat gagttaccga gtggaagcct  47040
ttgtctttca ccgaagactc caattccctt tcaatatacc tatgacttgg tttgaaatag  47100
acttgaaaac acattagtca tagcatatat gattaaaagt ataaatgagc tatgtgtgca  47160
atctagcaaa agaagttgcg tgaatcaaga atattgagct catgcctaag tttggtaaaa  47220
gtttgttcat caagaggctt ggtaaagata tcggctaatt gatctttagt gttaatgtaa  47280
gaaatctcga tatccccctt ttgttggtga tccctaagaa aatgataccg aatggctatg  47340
tgcttagtgc ggctatgctc gacgggattg tcggtcattt tgattgcact ctcattatca  47400
catagcaaag ggactttggt taatttgtaa ccgtagtccc gcagggtttg cctcatccaa  47460
agcaattgcg cgcaacaatg acctgcggca atgtactcag cttcggcggt ggaaagagcg  47520
accgaatttt gcttctttga agcccaagac accaaagatc ttcccaagaa ctggcaagtc  47580
cctgatgtgc tcttcctatt aattttgcac cccgcccaat cggcatccga ataaccaatc  47640
aaatcaaatg tggatccccg agggtaccaa agtccaaact taggagtata agccaaatat  47700
ctcaagattc gttttacggc cgtaaggtgg gattccttag ggtcggattg gaatcttgca  47760
cacatgcata cggaaagcat aatgtccggt cgagaagcac ataaatagag taaagaacct  47820
atcatcgacc ggtatacctt ttgatccacg gacttacctc ccgtgtcgag gtcgagatgc  47880
ccattggttc ccatgggtgt cttgatgggc ttggcatcct tcattccaaa cttgcttaga  47940
atatcttgag tatactttgt ttggctaagg aaggtgccct cttggagttg tttgacttgg  48000
aatcctagaa aatacttcaa ctcccccatc atagacatct cgaatttctg tgtcatgatc  48060
ctactaaact cttcacatgt agactcgtta gtagacccaa atataatatc atcaacataa  48120
atttggcata caaacaagtc attttcaaga gttttagtaa agagtgtagg atcggccttg  48180
ccgactttga agtcattagc aataaggaaa tctctaaggc attcatacca tgctcttggg  48240
ggcttgcttg agcccataaa gcgcctttga gagcctatag acatggttag ggtactcact  48300
atcttcaaag ccgggaggtt gctcaacata gacctcttcc ttgattggtc cgttgaggaa  48360
ggcacttttc acgtccattt gataaagctt aaagccatgg taagtagcat aggctaataa  48420
tattcgtatt gactcaagcc tagctacggg tgcataggtt tcaccgaaat ccaaaccttc  48480
gacttgggag tatcccttgg ccacaagtcg tgctttgttc cttgtcacca caccatgctc  48540
```

-continued

```
atcttgcttg ttgcggaaga cccatttggt ccctacaaca ttttgggtta ggacgtggaa  48600
ccaaatgcca tacctcattc ctcgtgaaat tgttgagctc ctcttgcatc gcccaccacc  48660
caatccgaat ctgaagtgct tcctctatcc tatgtggctc aatagaggaa acaaaagagt  48720
aatgctcaca aaaatgggca acacgagatc gagtagttac cccttatga atgtcgccga  48780
ggatggtgtc gacggggtga tctcgttgta ttgcttggtg gactcttggg tgtggcggtc  48840
ttggttcttc ctcatgctcc ttctcttgat catttgcatc tccccttga tcattgtcat  48900
tatcttgagg tggctcatct tcttgatttt gcccttcatc aacttgagcc tcatcctcat  48960
tttgagttgg tggagatgct tgcgtggtgg aggatgattg atcttgtgca cttggaggct  49020
cttcggattc cttaggacac acatccccaa tggacatgtt ccttagcgct atgcatggag  49080
cctcttcatt acctatctca tcaagatcaa cttgctgtac ttgagagccg ttagtctcat  49140
caaacacaac gtcacatgag acttcaacta gtccagtgga cttgttaaag accctatatg  49200
cccttgtgtt tgagtcataa ccaagtaaaa agccttctac agttttagga gcaaatttag  49260
attttctacc tcttttaaca agaataaagc atttgctacc aaaaactcta aagtatgaaa  49320
tgttgggctt tttaccggtt aggagttcat atgatgtctt cttgaggatt cggtgaagat  49380
ataaccggtt gatggcgtag caggcggtgt tgaccgctgc ggcccaaaac cggtccggtg  49440
tcttgtactc atcaagcatg gttcttgcca tgtccaatag agttcgattc ttcctctcca  49500
ctacaccatt ttgttgaggg gtgtagggag aagagaactc atgcttgatg ccctcctcct  49560
caagaaagcc ttcaatttgt gagttcttga actccgtccc gttgtcgctt cttattttct  49620
tgatccttaa gccgaactca ttttgagccc gtctcaagaa tcccttcaag gtctcttggg  49680
tttgagattt ttcctgtaaa aagaataccc aagtgaagcg agaataatca tccacaataa  49740
ctagacagta cttactcccg ccgatgctta tgtaagcaat cgggccgaat agatccatgt  49800
gtaggagctc cagtggcctg tcggtcgtca tgatgttctt gtgtggatga tgagctccaa  49860
cttgcttccc cgcctgacat gcgctacaaa tcctgtcttt ctcaaaatga acatttgtta  49920
atcctaaaat gtgttctccc tttagaagct tatgaagatt cttcatccca acatgggcta  49980
gtcggcggtg ccagagccaa cccatgttag tcttagcaat taagcatgtg tcgagttcag  50040
ctctatcaaa atctactaag tatagctgac cctctaacac acccttaaat gctattgaat  50100
cattacttct tctaaagaca gtgacaccta catcagtaaa aagacagttg tagcctattt  50160
gacataattg agaaacagaa agcaagttgt aatctaaaga atcaacaaga aaacattgga  50220
aatagaatgg tcaggagata tagcaatttt accaagtcct ttgaccaaac cttgatttcc  50280
atccccgaat gtgatagctc gttggggatc ttggtttttc tcatatgagg agaacattct  50340
tttctcccca gtcatatggt ttgtgcaccc gctgtcgagt atccaacttg agccccccgga  50400
tgcataaacc tacaaaacaa atttagttct tgactttagg tacccaaact gttttgggtc  50460
ctttggcatt agaaacaaga actttgggta cccaaacaca agtcttggaa cccttgtgtt  50520
tgcccccaac aaacttggca actactttgc cggatttgtt agtcaaaaca taggatgcat  50580
caaaagtttt aaatgaaata gcatgatcat ttgaagcatt aggagttttc tttctaggca  50640
acttagcacg ggttggttgc ctagaactag atgtctcacc cttatacata aaagcatggt  50700
tagggccaga gtgagacttc ctagaatgag ttctcctaat tttgctctca ggataaccgg  50760
cagggtacaa aatgtaaccc tcgttatcct gaggcatggg agccttgccc ttaacaaagt  50820
tggacaagtt cttaggaggg gcattaagtt tgacattgtc tcccctttgg aagccaatgt  50880
catccttaat gccggggcgt ctcccattat aaagcatgct acgagcaaat ttaaatttct  50940
```

-continued

```
cattctctaa gttgtgctcg gcaattttag catctagttt tgttatatga tcattttgtt  51000

gtttaattaa agccatatga tcatgaatag catcaatatc aacattttta catctagtgc  51060

aaatagtgac atgctcaatg gtggatgtag atggtttgca agaattaagt tcaacaatct  51120

tagcacgaag tatatcattc ttatctctaa gatcagaaat tgtaattttg caaacatcaa  51180

aatctttagc cttagcaatt aaattttcat tttctaatct aaggctagca agagatacat  51240

tcaattcatc aatcttaaca agcaaatcaa cattatcatc tctaagattg ggaattgaaa  51300

catcaccaaa tatgtgaatc aaccttaa                                     51328


<210> SEQ ID NO 107
<211> LENGTH: 58
<212> TYPE: DNA
<213> ORGANISM: Zea mays

<400> SEQUENCE: 107

cactgtgcgt cctctgcagg cagttgttga catgagcgca tcgtcactgc tgaatcgc       58
```

CORN EVENT MIR162

This is a §371 of PCT/US2007/012301, filed May 24, 2007, and published Dec. 13, 2007 as WO2007/142840, which claims priority from US Provisional Application No. 60/810,499, filed Jun. 3, 2006, both of which are incorporated herein by reference in their entirety.

BACKGROUND

The present invention relates generally to the field of plant molecular biology, plant transformation, and plant breeding. More specifically, the invention relates to insect resistant transgenic corn plants comprising a novel transgenic genotype and to methods of detecting the presence of nucleic acids that are unique to the transgenic corn plants in a sample and compositions thereof.

Plant pests are a major factor in the loss of the world's important agricultural crops. About $8 billion are lost every year in the U.S. alone due to infestations of non-mammalian pests including insects. In addition to losses in field crops, insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Good insect control can thus be reached, but these chemicals can sometimes also affect other, beneficial insects. Another problem resulting from the wide use of chemical pesticides is the appearance of resistant insect varieties. This has been partially alleviated by various resistance management practices, but there is an increasing need for alternative pest control agents. Biological pest control agents, such as *Bacillus thuringiensis* (Bt) strains expressing pesticidal toxins like δ-endotoxins, have also been applied to crop plants with satisfactory results, offering an alternative or compliment to chemical pesticides. The genes coding for some of these δ-endotoxins have been isolated and their expression in heterologous hosts have been shown to provide another tool for the control of economically important insect pests. In particular, the expression of Bt δ-endotoxins has provided efficient protection against selected insect pests, and transgenic plants expressing such toxins have been commercialized, allowing farmers to reduce applications of chemical insect control agents.

Another family of insecticidal proteins produced by *Bacillus* species during the vegetative stage of growth (vegetative insecticidal proteins (Vip)) has also been identified. U.S. Pat. Nos. 5,877,012, 6,107,279, and 6,137,033, herein incorporated by reference, describe a new class of insecticidal proteins called Vip3. Other disclosures, including WO 98/18932, WO 98/33991, WO 98/00546, and WO 99/57282, have also now identified homologues of the Vip3 class of proteins. Vip3 coding sequences encode approximately 88 kDa proteins that possess insecticidal activity against a wide spectrum of lepidopteran pests, including, but not limited to, black cutworm (BCW, *Agrois ipsilon*), fall armyworm (FAW, *Spodoptera frugiperda*), tobacco budworm (TBW, *Heliothis virescens*), sugarcane borer, (SCB, *Diatraca saccharalis*), lesser cornstalk borer (LCB, *Flasmopalpus lignosellus*), and corn earworm (CEW, *Helicoverpa zea*), and when expressed in transgenic plants, for example corn (*Zea mays*), confer protection to the plant from insect feeding damage.

Present plant transformation methods generally lead to the random integration of transgenes like vip3 into a host-plant genome. This random insertion of introduced DNA into the plant's genome can be lethal if the foreign DNA happens to insert into, and thus mutate, a critically important native gene. In addition, even if a random insertion event does not impair the functioning of a host cell gene, the expression of an inserted foreign gene may be influenced by "position effects" caused by the surrounding genomic DNA. In some cases, the gene is inserted into sites where the position effects are strong enough to prevent the synthesis of an effective amount of product from the introduced gene. For example, it has been observed in plants that there may be wide variations in levels of expression of a heterologous gene introduced into a plant's chromosome among individually selected events. There may also be differences in spatial or temporal patterns of expression, for example, differences in the relative expression of a transgene in various plant tissues, that may not correspond to the patterns expected from transcriptional regulatory elements present in the introduced gene construct. In other instances, overproduction of the gene product has deleterious effects on the cell. Because of these potential problems, it is common to produce hundreds of different events and screen those events for a single event that has desired transgene expression patterns and levels for commercial purposes. However, once a commercially viable site within the plant's genome is identified it would be advantageous to target genes of interest to that non-detrimental site.

Several methods for the targeted insertion of a nucleotide sequence of interest into a specific chromosomal site within a plant cell have been described. Site-specific recombination systems have been identified in several prokaryotic and lower eukaryotic organisms. Such systems typically comprise one or more proteins that recognize two copies of a specific nucleotide sequence, cleave and ligate those nucleotide sequences, and thereby provide a precise, site-specific exchange of genetic information. Several site-specific recombinases are known in the art. These include, but are not limited to, e.g., the bacteriophage P1 Cre/lox system (Austin et al. (1981) Cell 25: 729-736), the R/RS recombinase system from the pSR1 plasmid of the yeast *Zygosaccharomyces rouxii* (Araki et al. (1985) J. Mol. Biol. 182: 191-203), the Gin/gix system of phage Mu (Maeser and Kahlmann (1991) Mol. Gen. Genet. 230: 170-176), the FLP/FRT recombinase system from the 2.mu.m plasmid of the yeast *Saccharomyces cerevisiae* (Broach et al. (1982) Cell 29: 227-234), and the Int recombinase from bacteriophage Lambda (Landy (1989) Annu. Rev. Biochem. 58: 912-949; Landy (1993) Curr. Opin. Genet. Dev. 3: 699-707; Lorbach et al. (2000) J. Mol. Biol. 296: 1175-1181; and WO 01/16345). One particularly useful site-specific targeting approach, disclosed in US Patent Application Publication No. 2006/0130179, herein incorporated by reference, uses lambda integrase mediated recombination. The method comprises introducing into a plant cell a target nucleotide sequence comprising a first Integrase Recognition Site; introducing into the plant cell a donor nucleotide sequence comprising a second Integrase Recognition Site; and introducing into the plant cell an Integrase or Integrase complex. Another useful site-specific targeting approach is disclosed in US Patent Application Publication No. 2006/0253918, herein incorporated by reference, which uses homologous recombination to integrate one or more genes (gene stacking) at specific locations in the genome.

An event that has desired levels or patterns of transgene expression is useful for introgressing the transgene into other genetic backgrounds by sexual out-crossing using conventional breeding methods. Progeny of such crosses maintain the transgene expression characteristics of the original transformant. This strategy is used to ensure reliable gene expression in a number of varieties that are well adapted to local growing conditions. It would also be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well-known nucleic acid detection method including but not limited to thermal amplification (polymerase chain reaction (PCR)) using polynucleotide primers or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, for example, promoters, terminators, and marker genes, because for many DNA constructs, the coding sequence region is interchangeable. As a result, such methods may not be useful for discriminating between constructs that differ only with reference to the coding sequence. In addition, such methods may not be useful for discriminating between different events, particularly those produced using the same DNA construct unless the sequence of chromosomal DNA adjacent to the inserted heterologous DNA ("flanking DNA") is known.

For the foregoing reasons, there is a need for insect resistant transgenic corn events comprising novel nucleic acid sequences which are unique to the transgenic corn event, useful for identifying the transgenic corn event and for detecting nucleic acids from the transgenic corn event in a biological sample, as well as kits comprising the reagents necessary for use in detecting these nucleic acids in a biological sample. There is a further need to provide specific target sites within the maize genome to allow for targeting and control of insertion of nucleotide sequences to be integrated into the corn genome.

SUMMARY

The present invention relates to a transformed corn (*Zea mays*) event, designated MIR162 comprising a novel transgenic genotype that comprises a vip3Aa20 coding sequence, which is unique to event MIR162. The vip3Aa20 coding sequence encodes a Vip3Aa20 insecticidal protein that confers insect resistance to MIR162 corn plants. The MIR162 event also comprises a pmi coding sequence encoding a PMI protein that confers upon corn cells the ability to utilize mannose as a carbon source. In addition to the vip3A20 coding sequence, the present invention also provides other nucleic acids that are unique to MIR162. The invention also provides transgenic corn plants comprising the nucleic acids unique to MIR162, seed from the transgenic corn plants, and to methods for producing a transgenic corn plant comprising the unique nucleic acids of the invention by crossing a corn inbred comprising the nucleic acids unique to MIR162 with itself or another corn line of a different genotype. An example of seed, and hence corn plants grown from the seed, comprising nucleic acids unique to MIR162 was deposited at the American Type Culture Collection as accession No. PTA-8166. The transgenic corn plants of the invention may have essentially all of the morphological and physiological characteristics of corresponding isogenic non-transgenic corn plants in addition to those conferred upon the corn plants by the novel genotype of the invention. Biological samples and extracts from MIR162 corn plants, tissues and seeds are also provided by the present invention. The present invention also provides compositions and methods for detecting the presence of nucleic acids unique to MIR162 in biological samples based on the DNA sequence of the recombinant expression cassettes inserted into the corn genome that resulted in the MIR162 event and of genomic sequences flanking the insertion site. The present invention also provides a non-detrimental insertion target site on a maize chromosome useful for inserting genes of interest to a specific location on the chromosome and to methods of altering a maize genome by inserting heterologous nucleic acids at the disclosed insertion site or in the vicinity of the disclosed insertion site. The MIR162 event can be further characterized by analyzing expression levels of the Vip3Aa20 and PMI proteins as well as by testing MIR162 for efficacy against lepidopteran insect pests. The present invention also provides methods of producing transgenic corn plants resistant to a broader spectrum of insect pests by stacking the Vip3Aa20 insect resistant trait with insect resistance traits different than Vip3Aa20 .

The foregoing and other aspects of the invention will become more apparent from the following detailed description.

DESCRIPTION OF THE SEQUENCES IN THE SEQUENCE LISTING

SEQ ID NO: 1 is the Vip3Aa20 coding sequence in MIR162.
SEQ ID NO: 2 is the Vip3Aa20 amino acid sequence.
SEQ ID NO: 3 is the sequence of plasmid pNOV1300.
SEQ ID Nos: 4-12 are primers and probes useful in a TAQMAN assay.
SEQ ID NO: 13 is the sequence of a vip3Aa20 probe.
SEQ ID NO: 14 is the sequence of a pmi probe.
SEQ ID Nos: 15-37 are primers useful in the present invention.
SEQ ID No: 38 is the sequence of a vip3Aa20 amplicon.
SEQ ID Nos: 39-40 are primers useful in the present invention.
SEQ ID No: 41 is the sequence of the CJ134/179 5' amplicon.
SEQ ID Nos: 42-43 are primers useful in the present invention.
SEQ ID NO: 44 is a vip3Aa20 3' amplicon.
SEQ ID NO: 45 is the 5' genome-insert junction.
SEQ ID NO: 46 is corn genome sequence flanking 5' to insert.
SEQ ID NO: 47 is the 3' insert-genome junction.
SEQ ID NO: 48 is corn genome flanking 3' to insert.
SEQ ID NO: 49 is the MIR162 insert and flanking sequences.
SEQ ID Nos. 50-54 are primers useful in the present invention.
SEQ ID NO: 55 is a 5' PCR amplicon
SEQ ID Nos. 56-58 are primers useful in the present invention.
SEQ ID NO: 59 is a 3' PCR amplicon.
SEQ ID Nos. 60-105 are primers useful in the present invention.
SEQ ID NO: 106 is the sequence of the region of maize chromosome 5 comprising the disclosed chromosomal target site.
SEQ ID NO: 107 is the maize genomic sequence that was displaced by the insertion of heterologous DNA in MIR162.

DETAILED DESCRIPTION

The following definitions and methods are provided to better define the present invention and to guide those of ordinary skill in the art in the practice of the present invention. Unless otherwise noted, terms used herein are to be understood according to conventional usage by those of ordinary skill in the relevant art. Definitions of common terms in molecular biology may also be found in Rieger et al., Glossary of Genetics: Classical and Molecular, $5^{th}$ edition, Springer-Verlag: New York, 1994. The nomenclature for DNA bases and amino acids as set forth in 37 C.F.R. § 1.822 is used herein.

As used herein, the term "amplified" means the construction of multiple copies of a nucleic acid molecule or multiple copies complementary to the nucleic acid molecule using at least one of the nucleic acid molecules as a template. Amplification systems include, but not limited to the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology Principles and Applications*, D. H. Persing et al., Ed., American Society for Microbiology, Washington, D.C. (1993). The product of amplification is termed an amplicon.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, the term "corn" means *Zea mays* or maize and includes all plant varieties that can be bred with corn, including wild maize species.

"Detection kit" as used herein refers to a kit of parts useful in detecting the presence or absence of DNA unique to MIR162 plants in a sample, wherein the kit comprises nucleic acid probes and/or primers of the present invention, which hybridize specifically under high stringency conditions to a target DNA sequence, and other materials necessary to enable nucleic acid hybridization or amplification methods.

As used herein the term transgenic "event" refers to a recombinant plant produced by transformation and regeneration of a plant cell or tissue with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. Normally, transformation of plant tissue produces multiple events, each of which represent insertion of a DNA construct into a different location in the genome of a plant cell. Based on the expression of the transgene or other desirable characteristics, a particular event is selected. Thus, "event MIR162", "MIR162" or "MIR162 event" may be used interchangeably.

An insect resistant MIR162 corn plant can be bred by first sexually crossing a first parental corn plant consisting of a corn plant grown from a transgenic MIR162 corn plant, such as a MIR162 corn plant grown from the seed deposited at the ATCC under accession No. PTA-6188, and progeny thereof derived from transformation with the expression cassettes of the embodiments of the present invention that confers insect resistance, and a second parental corn plant that lacks insect resistance, thereby producing a plurality of first progeny plants; and then selecting a first progeny plant that is resistant to insects; and selfing the first progeny plant, thereby producing a plurality of second progeny plants; and then selecting from the second progeny plants an insect resistant plant. These steps can further include the back-crossing of the first insect resistant progeny plant or the second insect resistant progeny plant to the second parental corn plant or a third parental corn plant, thereby producing a corn plant that is resistant to insects.

"Expression cassette" as used herein means a nucleic acid molecule capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host; i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding sequence, may comprise other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability.

"Genotype" as used herein is the genetic material inherited from parent corn plants not all of which is necessarily expressed in the descendant corn plants. The MIR162 genotype refers to the heterologous genetic material transformed into the genome of a plant as well as the genetic material flanking the inserted sequence.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Operably-linked" refers to the association of nucleic acid sequences on a single nucleic acid fragment so that the function of one affects the function of the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Primers" as used herein are isolated nucleic acids that are annealed to a complimentary target DNA strand by nucleic acid hybridization to form a hybrid between the primer and the target DNA strand, and then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods.

A "probe" is an isolated nucleic acid to which is attached a conventional detectable label or reporter molecule, such as a radioactive isotope, ligand, chemiluminescent agent, or enzyme. Such a probe is complimentary to a strand of a target nucleic acid, in the case of the present invention, to a strand of genomic DNA from corn event MIR162. The DNA of MIR162 can be from a corn plant or from a sample that includes DNA from MIR162. Probes according to the present invention include not only deoxyribonucleic or ribonucleic acids but also polyamides and other probe materials that bind specifically to a target DNA sequence and can be used to detect the presence of that target DNA sequence.

Primers and probes are generally between 10 and 15 nucleotides or more in length. Primers and probes can also be at least 20 nucleotides or more in length, or at least 25 nucleotides or more, or at least 30 nucleotides or more in length. Such primers and probes hybridize specifically to a target sequence under high stringency hybridization conditions. Primers and probes according to the present invention may have complete sequence complementarity with the target sequence, although probes differing from the target sequence and which retain the ability to hybridize to target sequences may be designed by conventional methods.

As used herein gene or trait "stacking" is combining desired traits into one transgenic line. Plant breeders stack transgenic traits by making crosses between parents that each have a desired trait and then identifying offspring that have both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two different insect resistance traits, an insect resistance trait and a disease resistance trait, or a herbicide resistance trait. The use of a selectable marker in addition to a gene of interest would also be considered gene stacking.

"Stringent conditions" or "stringent hybridization conditions" include reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or wash conditions, target sequences can be identified which are 100% complementary to the probe (homologous probing). Alternatively, stringency conditions can be adjusted to allow some mismatching in sequences so that lower degrees of similarity are detected (heterologous probing). Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes*, Part I, Chapter 2 "Overview of principles of hybridization and the strategy of nucleic acid probe assays", Elsevier: N.Y.; and *Current Protocols in Molecular Biology*, Chapter 2, Ausubel et al., Eds., Greene Publishing and Wiley-Interscience: New York (1995), and also Sambrook et al. (2001) *Molecular Cloning: A Laboratory Manual* ($5^{th}$ Ed. Cols Spring Harbor Laboratory, Cold Spring Harbor, N.Y.).

Specificity is typically the function of post-hybridization washes, the critical factors being the ionic strength and temperature of the final wash solution. Generally, high stringency hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, under high stringency conditions a probe will hybridize to its target subsequence, but to no other sequences.

An example of high stringency hybridization conditions for hybridization of complementary nucleic acids which have more than 100 complementary-residues on a filter in a Southern or northern blot is 50% formamide with 1 mg of heparin at 42° C., with the hybridization being carried out overnight. An example of very high stringency wash conditions is 0.15M NaCl at 72° C. for about 15 minutes. An example of high stringency wash conditions is a 0.2×SSC wash at 65° C. for 15 minutes (see, Sambrook, infra, for a description of SSC buffer).

Exemplary hybridization conditions for the present invention include hybridization in 7% SDS, 0.25 M $NaPO_4$ pH 7.2 at 67° C. overnight, followed by two washings in 5% SDS, 0.20 M $NaPO_4$ pH7.2 at 65° C. for 30 minutes each wash, and two washings in 1% SDS, 0.20 M $NaPO_4$pH7.2 at 65° C. for 30 minutes each wash. An exemplary medium stringency wash for a duplex of, e.g., more than 100 nucleotides, is 1×SSC at 45° C. for 15 minutes. An exemplary low stringency wash for a duplex of, e.g., more than 100 nucleotides, is 4-6×SSC at 40° C. for 15 minutes.

For probes of about 10 to 50 nucleotides, high stringency conditions typically involve salt concentrations of less than about 1.0 M Na ion, typically about 0.01 to 1.0 M Na ion concentration (or other salts) at pH 7.0 to 8.3, and the temperature is typically at least about 30° C. High stringency conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under high stringency conditions are still substantially identical if the proteins that they encode are substantially identical. This occurs, e.g., when a copy of a nucleic acid is created using the maximum codon degeneracy permitted by the genetic code.

The following are exemplary sets of hybridization/wash conditions that may be used to hybridize nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mm EDTA at 50° C. with washing in 0.1×SSC, 0.1% SDS at 65° C. The sequences of the present invention may be detected using all the above conditions. For the purposes of defining the invention, the high stringency conditions are used.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule. As used herein, "transgenic" refers to a plant, plant cell, or multitude of structured or unstructured plant cells having integrated, via well known techniques of genetic manipulation and gene insertion, a sequence of nucleic acid representing a gene of interest into the plant genome, and typically into a chromosome of a cell nucleus, mitochondria or other organelle containing chromosomes, at a locus different to, or in a number of copies greater than, that normally present in the native plant or plant cell. Transgenic plants result from the manipulation and insertion of such nucleic acid sequences, as opposed to naturally occurring mutations, to produce a non-naturally occurring plant or a plant with a non-naturally occurring genotype. Techniques for transformation of plants and plant cells are well known in the art and may comprise for example electroporation, microinjection, *Agrobacterium*-mediated transformation, and ballistic transformation.

As used herein, the term "unique" to MIR162 means distinctively characteristic of MIR162. Therefore, nucleic acids unique to event MIR162 are not found in other non-MIR162 corn plants.

The "Vip3" class of proteins comprises, for example, Vip3Aa, Vip3Ab, Vip3Ac, Vip3Ad, Vip3Ae, VipAf, Vip3Ag, Vip3Ba, and Vip3Bb, and their homologues. "Homologue" means that the indicated protein or polypeptide bears a defined relationship to other members of the Vip3 class of proteins. "Vip3Aa20" is a Vip3 homologue unique to event MIR162. It was generated by spontaneous mutations introduced into the maize-optimized vip3Aa19 gene comprised in pNOV1300 (SEQ ID NO: 3) during the plant transformation process.

This invention relates to a genetically improved line of corn that produces an insect control protein, Vip3Aa20, and a phosphomannose isomerase enzyme (PMI) that allows the plant to utilize mannose as a carbon source. The invention is particularly drawn to a transgenic corn event designated MIR162 comprising a novel genotype, as well as to compositions and methods for detecting nucleic acids unique to MIR162 in a biological sample. The invention is further drawn to corn plants comprising the MIR162 genotype, to transgenic seed from the corn plants, and to methods for producing a corn plant comprising the MIR162 genotype by crossing a corn inbred comprising the MIR162 genotype with itself or another corn line. Corn plants comprising the MIR162 genotype of the invention are useful in controlling lepidopteran insect pests including, but not limited to, black cutworm (BCW, *Agrotis ipsilon*), fall armyworm (FAW, *Spodoptera frugiperda*), tobacco budworm (TBW, *Heliothis virescens*), sugarcane borer (SCB, *Diatraea saccharalis*), lesser cornstalk borer (LCB, *Elasmopalpus lignosellus*), corn earworm (CEW, *Helicoverpa zea*), and western bean cutworm (WBCW, *Striacosta albicosta*). The invention is further drawn to a method of protecting transgenic corn from feeding damage whereby stacking the insect resistance trait of MIR162 with a different insect resistance trait in the same transgenic plant results is a corn plant that is protected from feeding damage to a greater degree than the insect resistance traits alone.

In one embodiment, the present invention encompasses an isolated nucleic acid molecule comprising a nucleotide sequence that is unique to event MIR162.

In another embodiment, the present invention encompasses an isolated nucleic acid molecule that links a heterologous DNA molecule inserted into the genome of MIR162 to genome DNA in MIR162 comprising at least 10 or more (for example 15, 20, 25, 50 or more) contiguous nucleotides of the heterologous DNA molecule and at least 10 or more (for example 15, 20, 25, 50, or more) contiguous nucleotides of the genome DNA flanking the point of insertion of the heterologous DNA molecule. Also included are nucleotide sequences that comprise 10 or more nucleotides of contiguous insert sequence from event MIR162 and at least one nucleotide of flanking DNA from event MIR1162 adjacent to the insert sequence. Such nucleotide sequences are unique to and diagnostic for event MIR162. Nucleic acid amplification or hybridization of genomic DNA from MIR162 produces an amplicon comprising such unique sequences and is diagnostic for event MIR162. In one aspect of this embodiment, the nucleotide sequence is selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the complements thereof.

In another embodiment, the invention encompasses an isolated nucleic acid molecule comprising a nucleotide sequence which comprises at least one junction sequence of event MIR162, wherein a junction sequence spans the junction between a heterologous expression cassette inserted into the corn genome and DNA from the corn genome flanking the insertion site and is diagnostic for the event. In one aspect of this embodiment, the junction sequence is selected from the group consisting of SEQ ID NO: 45, SEQ ID NO: 47, and the complements thereof.

In another embodiment, the present invention encompasses an isolated nucleic acid molecule linking a heterologous DNA molecule to the corn plant genome in event MIR162 comprising a sequence of from about 11 to about 20 contiguous nucleotides selected from the group consisting of SEQ ID NO: 45, SEQ ID NO: 47, and the complements thereof.

In another embodiment, the invention encompasses an isolated nucleic acid molecule comprising a nucleotide sequence selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the complements thereof. In one aspect of this embodiment, the isolated nucleic acid molecule is comprised in a corn seed deposited at the American Type Culture Collection under the accession No. PTA-8166, or in plants grown from the seed.

In one embodiment of the present invention, an amplicon comprising a nucleotide sequence unique to event MIR162 is provided. In one aspect of this embodiment, the nucleotide sequence is selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the complements thereof.

In another embodiment, the present invention encompasses flanking sequence primers for detecting event MIR162. Such flanking sequence primers comprise a nucleotide sequence of at least 10-15 contiguous nucleotides from the 5' or the 3' flanking sequence. In one aspect of this embodiment, the contiguous nucleotides are selected from nucleotides 1-1088 (inclusive) of SEQ ID NO: 49 (arbitrarily designated herein as the 5' flanking sequence), or the complements thereof. In another aspect of this embodiment, the 5' flanking sequence primers are selected from the group consisting of SEQ ID NO: 36, SEQ ID NO: 39, SEQ ID NO: 53, SEQ ID NOs: 68-80, and the complements thereof. In another aspect of this embodiment, the contiguous nucleotides are selected from nucleotides 9391-10579 (inclusive) of SEQ ID NO: 49 (arbitrarily designated herein as the 3' flanking sequence), or the complements thereof. In yet another aspect of this embodiment, the 3' flanking sequence primers are selected from the group consisting of SEQ ID NO: 58, SEQ ID NOs: 97-105, and the complements thereof.

In still another embodiment, the present invention encompasses a pair of polynucleotide primers comprising a first polynucleotide primer and a second polynucleotide primer that function together in the presence of a event MIR162 DNA template in a sample to produce an amplicon diagnostic for event MIR162. In one aspect of this embodiment, the first primer and/or the second primer is chosen from SEQ ID NO: 1 or the compliment thereof. In another aspect of this embodiment, the first primer and/or the second primer is selected from the group consisting of SEQ ID NOs: 15-35, SEQ ID NO: 37, SEQ ID NO: 42, and the complements thereof. In yet another aspect of this embodiment, the amplicon that is produced by the pair of primers comprises SEQ ID NO: 1, SEQ ID NO: 38, SEQ ID NO: 44, or the complements thereof.

In another embodiment, the present invention encompasses a pair of polynucleotide primers comprising a first polynucleotide primer and a second polynucleotide primer which function together in the presence of a event MIR162 DNA template in a sample to produce an amplicon diagnostic for event MIR162, wherein the first primer is or is complementary to a corn plant genome sequence flanking the point of insertion of a heterologous DNA sequence inserted into the genome of event MIR162, and the second polynucleotide primer sequence is or is complementary to the heterologous DNA sequence inserted into the genome of event MIR162.

In one aspect of this embodiment, the first polynucleotide primer comprises at least 10 contiguous nucleotides from a nucleotide sequence selected from the group consisting of nucleotides 1-1088 of SEQ ID NO: 49, nucleotides 9391-10579 of SEQ ID NO: 49, and the complements thereof. In a further aspect of this embodiment the first primer is selected from the group consisting of SEQ ID NO: 36, SEQ ID NO: 39, SEQ ID NO: 53, SEQ ID NO: 57, SEQ ID NOs: 68-72, SEQ ID NO: 79, SEQ ID NO: 80, SEQ ID NOs: 97-105, and the complements thereof. In another aspect of this embodiment, the second polynucleotide primer comprises at least 10 contiguous nucleotides from position 1089-9390 of SEQ ID NO: 49, or complements thereof. In still a further aspect of this embodiment, the second polynucleotide primer is selected from the group consisting of SEQ ID NOs: 15-35, SEQ ID NO: 37, SEQ ID NO: 40, SEQ ID NOs: 50-52, SEQ ID NOs: 54, SEQ ID NO: 56, SEQ ID NO: 57, SEQ ID NO: 63, SEQ ID NO: 73, SEQ ID NO: 82, SEQ ID NO: 96, and the complements thereof.

In another aspect of this embodiment, the first polynucleotide primer, which is set forth in SEQ ID NO: 36, and the second polynucleotide primer which is set forth in SEQ ID NO: 37, function together in the presence of a event MIR162DNA template in a sample to produce an amplicon diagnostic for event MIR162 as described in Example 4. In one embodiment of this aspect, the amplicon comprises the nucleotide sequence set forth in SEQ ID NO: 38.

In yet another aspect of this embodiment, the first polynucleotide primer, which is set forth in SEQ ID NO: 39, and the second polynucleotide primer, which is set forth in SEQ ID NO: 40, function together in the presence of a corn event MIR162 DNA template in a sample to produce an amplicon diagnostic for the corn event MIR162 as described in Example 4. In one embodiment of this aspect, the amplicon comprises the nucleotide sequence set forth in SEQ ID NO: 41.

In another aspect of this embodiment, the first polynucleotide primer, which is set forth in SEQ ID NO: 53, and the second polynucleotide primer, which is set forth in SEQ ID NO: 54, function together in the presence of a corn event MIR62 DNA template in a sample to produce an amplicon diagnostic for the corn event MIR162 as described in Example 5. In one embodiment, the amplicon comprises the nucleotide sequence set forth in SEQ ID NO: 55.

In a still a further aspect of this embodiment, the first polynucleotide primer, which is set forth in SEQ ID NO: 58, and the second polynucleotide primer, which is set forth in SEQ ID NO: 56, function together in the presence of a corn event MIR162 DNA template in a sample to produce an amplicon diagnostic for the corn event MIR162 as described in Example 5. In one embodiment, the amplicon comprises the nucleotide sequence set forth in SEQ ID NO: 59.

Of course, it is well within the skill in the art to obtain additional sequence further out into the genome sequence flanking either end of the inserted heterologous DNA sequences for use as a primer sequence that can be used in such primer pairs for amplifying the sequences that are diagnostic for the MIR162 event. For the purposes of this disclosure, the phrase "further out into the genome sequence flanking either end of the inserted heterologous DNA sequences" refers specifically to a sequential movement away from the ends of the inserted heterologous DNA sequences, the points at which the inserted DNA sequences are adjacent to native genomic DNA sequence, and out into the genomic DNA of the particular chromosome into which the heterologous DNA sequences were inserted. Preferably, a primer sequence corresponding to or complementary to a part of the insert sequence should prime the transcriptional extension of a nascent strand of DNA or RNA toward the nearest flanking sequence junction. Consequently, a primer sequence corresponding to or complementary to a part of the genomic flanking sequence should prime the transcriptional extension of a nascent strand of DNA or RNA toward the nearest flanking sequence junction. A primer sequence can be, or can be complementary to, a heterologous DNA sequence inserted into the chromosome of the plant, or a genomic flanking sequence. One skilled in the art would readily recognize the benefit of whether a primer sequence would need to be, or would need to be complementary to, the sequence as set forth within the inserted heterologous DNA sequence or as set forth SEQ ID NO: 38 depending upon the nature of the product desired to be obtained through the use of the nested set of primers intended for use in amplifying a particular flanking sequence containing the junction between the genomic DNA sequence and the inserted heterologous DNA sequence.

In another embodiment, the present invention encompasses an isolated insecticidal protein comprising SEQ ID NO: 2 and a nucleic acid molecule encoding SEQ ID NO: 2. In one aspect of this embodiment, the nucleic acid molecule is SEQ ID NO: 1. The present invention also encompasses a chimeric gene comprising a heterologous promoter operably linked to the nucleic acid molecule, and to recombinant vectors and host cells comprising the chimeric gene.

In yet another embodiment, the present invention encompasses a method of detecting the presence of a nucleic acid molecule that is unique to event MIR162 in a sample comprising corn nucleic acids, wherein the method comprises: (a) contacting the sample with a pair of polynucleotide primers that, when used in a nucleic acid amplification reaction with genomic DNA from event MIR162 produces an amplicon that is diagnostic for event MIR162; (b) performing a nucleic acid amplification reaction, thereby producing the amplicon; and (c) detecting the amplicon. In one aspect of this embodiment, the amplicon comprises a nucleotide sequence selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the compliments thereof.

In another embodiment, the present invention encompasses a method of detecting the presence of a nucleic acid molecule that is unique to event MIR162 in a sample comprising corn nucleic acids, wherein the method comprises: (a) contacting the sample with a probe that hybridizes under high stringency conditions with genomic DNA from event MIR162 and does not hybridize under high stringency conditions with DNA from a control corn plant; (b) subjecting the sample and probe to high stringency hybridization conditions; and (c) detecting hybridization of the probe to the DNA. Detection can be by any means well known in the art including fluorescent, chemiluminescent, radiological, immunological, and the like. In the case in which hybridization is intended to be used as a means for amplification of a particular sequence to produce an amplicon which is diagnostic for the MIR62 event, the production and detection by any means well known in the art of the amplicon is intended to be indicative of the intended hybridization to the target sequence where one probe or primer is utilized, or sequences where two or more probes or primers are utilized. The term "biological sample" is intended to comprise a sample that contains or is suspected of containing a nucleic acid comprising from between five and ten nucleotides either side of the point at which one or the other of the two terminal ends of the inserted heterologous DNA sequence contacts the genomic DNA sequence within the chromosome into which the heterologous DNA sequence was inserted, herein also known as the junction sequences. In addition, the junction sequence comprises as little as two nucleotides: those being the first nucleotide within the flanking genomic DNA adjacent to and covalently linked to the first nucleotide within the inserted heterologous DNA sequence. In one aspect of this embodiment, the probe comprises a nucleotide sequence selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the complements thereof.

In yet another embodiment, the present invention encompasses a kit for the detection of nucleic acids that are unique to event MIR162 in biological sample. The kit includes at least one nucleic acid molecule of sufficient length of contiguous polynucleotides to function as a primer or probe in a nucleic acid detection method, and which upon amplification of or hybridization to a target nucleic acid sequence in a sample followed by detection of the amplicon or hybridization to the target sequence, are diagnostic for the presence of nucleic acid sequences unique to event MIR162 in the sample. The kit further includes other materials necessary to enable nucleic acid hybridization or amplification methods. In one aspect of this embodiment, a nucleic acid molecule contained in the kit comprises a nucleotide sequence from SEQ ID NO: 1 or SEQ ID NO: 49. In another aspect of this embodiment, the nucleic acid molecule is a primer selected from the group consisting of SEQ ID NOs: 15-37, SEQ ID NO: 39, SEQ ID NO: 40, SEQ ID NO: 42, SEQ ID NO: 43, SEQ ID NOs: 50-54, SEQ ID NOs: 56-58, SEQ ID NOs: 60-105, and the complements thereof. In yet another aspect of this embodiment, the amplicon comprises SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, or the complements thereof. A variety of detection methods can be used including, but not limited to TAQMAN (Perkin Elmer), thermal amplification, ligase chain reaction, southern hybridization, ELISA methods, and calorimetric and fluorescent detection methods. In particular the present invention provides for kits for detecting the presence of the target sequence, i.e., at least the vip3Aa20 sequence or a junction sequence, in a sample containing genomic nucleic acid from MIR162. The kit is comprised of at least one polynucleotide capable of binding to the target site or substantially adjacent to the target site and at least one means for detecting the binding of the polynucleotide to the target site. The detecting means can be fluorescent, chemiluminescent, calorimetric, or isotopic and can be coupled at least with immunological methods for detecting the binding. A kit is also envisioned which can detect the presence of the target site in a sample, i.e., at least the vip3Aa20 sequence or a junction sequence of MIR162, taking advantage of two or more polynucleotide sequences which together are capable of binding to nucleotide sequences adjacent to or within about 100 base pairs, or within about 200 base pairs, or within about 500 base pairs or within about 1000 base pairs of the target sequence and which can be extended toward each other to form an amplicon which contains at least the target site.

In another embodiment, the present invention encompasses a method of detecting Vip3Aa20 protein in a biological sample, the method comprising: (a) extracting protein from event MIR162 tissue; (b) assaying the extracted protein using an immunological method comprising antibody specific for the Vip3Aa20 protein produced by the MIR162 event; and (c) detecting the binding of said antibody to the Vip3Aa20 protein.

In yet another embodiment, the present invention encompasses a biological sample derived from a event MIR162 corn plant, tissue, or seed, wherein the sample comprises a nucleotide sequence which is or is complementary to a sequence that is unique to event MIR162, and wherein the sequence is detectable in the sample using a nucleic acid amplification or nucleic acid hybridization method. In one aspect of this embodiment, the nucleotide sequence is or is complementary to SEQ ID NO: 1, SEQ ID NO: 38, SEQ ID NO: 41, SEQ ID NO: 45, SEQ ID NO: 47, SEQ ID NO: 49, SEQ ID NO: 55, or SEQ ID NO: 59. In another aspect of this embodiment, the sample is selected from the group consisting of corn flour, corn meal, corn syrup, corn oil, cornstarch, and cereals manufactured in whole or in part to contain corn by-products.

In another embodiment, the present invention encompasses an extract of a biological sample derived from a MIR162 corn plant, tissue, or seed comprising a nucleotide sequence which is or is complementary to a sequence that is unique to MIR162. In one aspect of this embodiment, the sequence is detectable in the extract using a nucleic acid amplification or nucleic acid hybridization method. In another aspect of this embodiment, the sequence is or is complementary to SEQ ID NO: 1, SEQ ID NO: 38, SEQ ID NO: 41, SEQ ID NO: 45, SEQ ID NO: 47, SEQ ID NO: 49, SEQ ID NO: 55, or SEQ ID NO: 59. In yet another aspect of this embodiment, the sample is selected from the group consisting of corn flour, corn meal, corn syrup, corn oil, cornstarch, and cereals manufactured in whole or in part to contain corn by-products.

Another embodiment of the present invention encompasses a corn plant, or parts thereof, and seed from a corn plant comprising the genotype of the transgenic event MIR162, wherein the genotype comprises a nucleotide sequence set forth in SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, or the complements thereof. One example of corn seed comprising the nucleic acid molecules of the invention was deposited 23 Jan. 2007 and assigned the ATCC Accession No. PTA-8166. In one aspect of this embodiment, the corn plant is from the inbred corn lines CG5NA58, CG5NA58A, CG3ND97, CG5NAO1, CG5NF22, CG4NU15, CG00685, CGO0526, CG00716, NP904, NP911, NP948, NP934, NP982, NP991, NP993, NP2010, NP2013, NP2015, NP2017, NP2029, NP2031, NP2034, NP2045, NP2052, NP2138, NP2151, NP2166, NP2161, NP2171, NP2174, NP2208, NP2213, NP2222, NP2275, NP2276, NP2316, BCTT609, AF031, NPH8431, 894, BUTT201, R327H, 2044BT, and 2070BT. One skilled in the art will recognize however, that the MIR162 genotype can be introgressed into any plant variety that can be bred with corn, including wild maize species, and thus the list of inbred lines of this embodiment are not meant to be limiting.

In another embodiment, the present invention encompasses a corn plant comprising at least a first and a second DNA sequence linked together to form a contiguous nucleotide sequence, wherein the first DNA sequence is within a junction sequence and comprises at least about 11 contiguous nucleotides selected from the group consisting of nucleotides 1079-1098 of SEQ ID NO: 49, nucleotides 9381-9400, and the complements thereof, wherein the second DNA sequence is within the heterologous insert DNA sequence set forth in SEQ ID NO: 49, and the complements thereof, and wherein the first and the second DNA sequences are useful as nucleotide primers or probes for detecting the presence of corn event MIR162 nucleic acid sequences in a biological sample. In one aspect of this embodiment, the nucleotide primers are used in a DNA amplification method to amplify a target DNA sequence from template DNA extracted from the corn plant and the corn plant is identifiable from other corn plants by the production of an amplicon corresponding to a DNA sequence comprising SEQ ID NO: 45 or SEQ ID NO: 47.

Corn plants of the invention can be further characterized in that simultaneously digesting the plant's genomic DNA with the restriction endonucleases KpnI, EcoRV or NcoI results in an about a 8 kb, a 13 kb or 4.6 kb vip3Aa20 hybridizing band, respectively, using a vip3Aa20 probe under high stringency conditions. Exemplified herein is a vip3Aa20 probe comprising the nucleotide sequence set forth in SEQ ID NO: 13.

Corn plants of the invention can be further characterized in that digesting the plant's genomic DNA with the restriction endonuclease Acc651 or BamHI results in a single pmi hybridizing band using a pmi probe under high stringency conditions. Exemplified herein is a pmi probe comprising the nucleotide sequence set forth in SEQ ID NO: 14.

In one embodiment, the present invention provides a corn plant, wherein the MIR162 genotype confers upon the corn plant insect resistance or ability to utilize mannose as a carbon source, or both insect resistance and the ability to utilize mannose as a carbon source. In one aspect of this embodiment, the transgenic genotype conferring insect resistance upon the corn plant of the invention comprises a vip3Aa20 gene and the transgenic genotype conferring the ability to utilize mannose as a carbon source upon the maize plant of the invention comprises a pmi gene.

In yet another embodiment, the present invention provides a method for producing a corn plant resistant to lepidopteran pests comprising: (a) sexually crossing a first parent corn plant with a second parent corn plant, wherein said first or second parent corn plant comprises event MIR162 DNA, thereby producing a plurality of first generation progeny plants; (b) selecting a first generation progeny plant that is resistant to one or more lepidopteran pests; (c) selfing the first generation progeny plant, thereby producing a plurality of second generation progeny plants; and (d) selecting from the second generation progeny plants, a plant that is resistant to one or more lepidopteran pests; wherein the second generation progeny plants comprise a nucleotide sequence selected from the group consisting of SEQ ID NO: 1, SEQ ID NO: 45, SEQ ID NO: 47, SEQ ID NO: 49, SEQ ID NO: 55, and SEQ ID NO: 59.

In another embodiment, the present invention provides a method of producing hybrid corn seeds comprising: (a) planting seeds of a first inbred corn line comprising a nucleotide sequence selected from the group consisting of SEQ ID NO: 1, SEQ ID NO: 45, SEQ ID NO: 47, SEQ ID NO: 49, SEQ ID NO: 55, and SEQ ID NO: 59, and seeds of a second inbred line having a different genotype; (b) cultivating corn plants resulting from said planting until time of flowering; (c) emasculating said flowers of plants of one of the corn inbred lines; (d) sexually crossing the two different inbred lines with each other; and (e) harvesting the hybrid seed produced thereby. In one aspect of this embodiment, the first inbred corn line provides the female parents. In another aspect of this embodiment, the first inbred corn line provides the male parents. The present invention also encompasses the hybrid seed produced by the embodied method and hybrid plants grown from the seed.

One skilled in the art will recognize that the transgenic genotype of MIR162 can be introgressed by breeding into other corn lines comprising different transgenic genotypes. For example, a MIR162 corn inbred can be crossed with a corn inbred comprising the transgenic genotype of the lepidopteran resistant Bt11 event (U.S. Pat. Nos. 6,114,608 and 6,342,660, herein incorporated by reference). The resulting seed and progeny plants have the stacked insect resistance traits and the combined spectrum of activity of Cry1Ab and Vip3Aa20. Another trait stack encompassed by the present invention includes combining the MIR162 insect resistance trait and the MIR604 insect resistance trait (US Patent Application publication No. 2005/0216970, published Sep. 29, 2005, herein incorporated by reference). The stacked traits in the resulting seed and progeny confer upon the plants an increased spectrum of activity; i.e. the plants are active against both lepidopteran and coleopteran insect pests.

Therefore, the present invention encompasses a method of protecting a transgenic corn plant from feeding damage by one or more insect pests wherein the method comprises stacking in the same transgenic corn plant a Vip3Aa20 insect resistance trait with another insect resistance trait that is different from Vip3Aa20, whereby the stacked traits protect the corn plant against feeding damage by one or more insect pests to a greater degree than would be expected due to the insect resistance traits alone. In one aspect of this embodiment, the Vip3Aa20 insect resistance trait comprised in event MIR162 is stacked with the Cry3A055 insect resistance trait comprised in event MIR604 in the same transgenic corn plant by sexually crossing event MIR162 with event MIR604 or by transforming the traits together into the same plant.

Examples of other transgenic events which can be crossed with a MIR162 inbred include, the glyphosate tolerant GA21 event, the glyphosate tolerant/lepidopteran insect resistant MON802 event, the lepidopteran resistant DBT418 event, the male sterile event MS3, the phosphinothricin tolerant event B16, the lepidopteran insect resistant event MON 80100, the phosphinothricin tolerant events T14 and T25, the lepidopteran insect resistant event 176, and the coleopteran resistant event MON863, all of which are known in the art. It will be further recognized that other combinations or stacks can be made with the transgenic genotype of the invention and thus these examples should not be viewed as limiting.

One skilled in the art will also recognize that transgenic corn seed comprising the MIR162 genotype can be treated with various seed-treatment chemicals, including insecticides, to augment or syngergize the insecticidal activity of the Vip3Aa20 protein.

The subject invention discloses herein a specific site on chromosome 5 in the maize genome that is excellent for insertion of heterologous nucleic acids. Also disclosed is a 5' molecular marker (opie2; nucleotides 1680-3338 of SEQ ID NO: 106) and a 3' molecular marker (gag; nucleotides 43,275-45,086 of SEQ ID NO: 106) useful in identifying the location of a targeting site on chromosome 5. Thus, the subject invention provides methods to introduce heterologous nucleic acids of interest into this pre-established target site or in the vicinity of this target site. The subject invention also encompasses a corn seed and/or a corn plant comprising any heterologous nucleotide sequence inserted at the disclosed target site or in the general vicinity of such site. One option to accomplish such targeted integration is to substitute a different insert in place of the vip3Aa20 expression cassette exemplified herein. In this general regard, targeted homologous recombination, for example without limitation, can be used according to the subject invention. "Homologous recombination" refers to a reaction between any pair of nucleotide sequences having corresponding sites containing a similar nucleotide sequence (i.e., homologous sequences) through which the two molecules can interact (recombine) to form a new, recombinant DNA sequence. The sites of similar nucleotide sequence are each referred to herein as a "homology sequence". Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement." This type of technology is the subject of, for example, US patent Application Publication No. 2006/0253918, herein incorporated by reference. With the disclosed target site now being identified and with the sequences surrounding the identified target site, the skilled person will recognize that other methods for targeted integration of heterologous nucleic acids may be used. Such methods, for example without limitation, are disclosed in US Patent Application Publication No. 2007/0039074 and US Patent Application Publication No. 2006/0130179.

In one embodiment, the present invention encompasses a maize chromosomal target site located on chromosome 5 between a opie2 molecular marker set forth as nucleotides 1680-3338 of SEQ ID NO: 106 and a gag molecular marker set forth as nucleotides 43,275-45,086 of SEQ ID NO: 106, wherein the target site comprises a heterologous nucleic acid. In another embodiment, the maize chromosomal target site is located on chromosome 5 between nucleotides 25,454 and 25,513 of SEQ ID NO: 106. In yet another embodiment, the chromosomal target site is flanked 5' by nucleotides 5,454 to 25,454 of SEQ ID NO: 106 and flanked 3' by nucleotides 25,513 to 45,513 of SEQ ID NO: 106.

In one embodiment, the present invention encompasses a method of making a transgenic maize plant comprising inserting a heterologous nucleic acid at a position on chromosome 5 located between a opie2 molecular marker set forth as nucleotides 1680-3338 of SEQ ID NO: 106 and a gag molecular marker set forth as nucleotides 43,275-45,086 of SEQ ID NO: 106. In another embodiment, the heterologous nucleic acid is inserted on chromosome 5 between nucleotides 25,454 and 25,513 of SEQ ID NO: 106. In still another embodiment, the inserted heterologous nucleic acid is flanked 5' by nucleotides 5,454 to 25,454 of SEQ ID NO: 106 and flanked 3' by nucleotides 25,513 to 45,513 of SEQ ID NO: 106

The transgenic genotype of the present invention can be introgressed in any corn inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Corn (*Zea mays* L.), can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the ears.

A reliable method of controlling male fertility in plants offers the opportunity for improved plant breeding. This is especially true for development of corn hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid corn seed is typically produced by a male sterility system incorporating manual or mechanical detasseling. Alternate strips of two corn inbreds are planted in a field, and the pollen-bearing tassels are removed from one of the inbreds (female). Providing that there is sufficient isolation from sources of foreign corn pollen the ears of the detasseled inbred will be fertilized only from the other inbred (male), and the resulting seed is therefore hybrid and will form hybrid plants.

The laborious, and occasionally unreliable, detasseling process can be avoided by using one of many methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329,308 and PCT application PCT/CA90/00037 published as WO 90/08828).

The use of male sterile inbreds is but one factor in the production of corn hybrids. Plant breeding techniques known in the art and used in a corn plant breeding program include, but are not limited to, recurrent selection, backcrossing, pedigree breeding, restriction length polymorphism enhanced selection, genetic marker enhanced selection and transformation. The development of corn hybrids in a corn plant breeding program requires, in general, the development of homozygous inbred lines, the crossing of these lines, and the evaluation of the crosses. Pedigree breeding and recurrent selection breeding methods are used to develop inbred lines from breeding populations. Corn plant breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development, as practiced in a corn plant-breeding program, are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$; etc.

Recurrent selection breeding, backcrossing for example, can be used to improve an inbred line and a hybrid that is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a corn plant-breeding program, elite inbreds can be used as a parental line or starling material or source population and can serve as either the donor or recurrent parent.

A single cross corn hybrid results from the cross of two inbred lines, each of which has a genotype that complements the genotype of the other. The hybrid progeny of the first generation is designated $F_1$. In the development of commercial hybrids in a corn plant-breeding program, only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a corn hybrid in a corn plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in corn, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)×(C×D). A three-way cross hybrid is produced from three inbred lines where two of the inbred lines are crossed (A×B) and then the resulting $F_1$ hybrid is crossed with the third inbred (A×B)×C. Much of the hybrid vigor exhibited by $F_1$ hybrids is lost in the next generation ($F_2$). Consequently, seed from hybrids is not used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed.

Once the seed is planted, it is possible to identify and select these self-pollinated plants. These self-pollinated plants will be genetically equivalent to the female inbred line used to produce the hybrid.

Typically these self-pollinated plants can be identified and selected due to their decreased vigor. Female selfs are identified by their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1-8 (1995), the disclosure of which is expressly incorporated herein by reference. Through these technologies, the homozygosity of the self-pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritica si Aplicata Vol. 20 (1) p. 29-42.

As is readily apparent to one skilled in the art, the foregoing are only some of the various ways by which the inbred of the present invention can be obtained by those looking to introgress the transgenic genotype of the invention into other corn lines. Other means are available, and the above examples are illustrative only.

The following examples are intended solely to illustrate one or more preferred embodiments of the invention and are not to be construed as limiting the scope of the invention.

EXAMPLES

Example 1

Transformation and Selection of the MIR162 Event

The MIR604 event was produced by *Agrobacterium*-mediated transformation of a proprietary corn (*Zea mays*) line. Immature embryos were transformed essentially as described in Negrotto et al. (Plant Cell Reports 19: 798-803, 2000), incorporated herein by reference, using a DNA fragment from plasmid pNOV1300 (SEQ ID NO: 3). pNOV1300 contains a nucleotide sequence comprising tandem expression cassettes. The first expression cassette comprises a ZmUbiInt promoter region from a *Zea mays* polyubiquitin gene, which contains the first intron (GenBank® Accession number S94464) operably linked to a vip3AaJ9 coding sequence further operably linked to PEPC Intron #9 from the phosphoenolpyruvate carboxylase gene (GenBank® Accession Number X15239) from *Zea mays* (Matsuoka and Minami, 1989. European J. Of Biochem. 181:593-598) and a 35S terminator sequence from the 35S RNA from the cauliflower mosaic virus genome (Similar to GenBank® Accession Number AF 140604). Its function is to provide a polyadenylation sequence (Franck et al., 1980. Cell 21:285-294). The vip3Aa19 gene in pNOV1300 comprises a synthetic maize-optimized vip3Aa coding sequence (Estruch, et al., 1999.) which was synthesized to accommodate the preferred codon usage for maize (Murray et al., 1989). The synthetic vip3Aa19 coding sequence used in plant transformations encodes the identical amino acid sequence as the native vip3Aa1 coding sequence found in the soil bacterium *Bacillus thuringiensis* strain AB88 (U.S. Pat. No. 5,877,012), with the exception of a single amino acid difference at position 284; the native vip3Aa1 coding sequence encodes lysine, whereas the synthetic vip3Aa19 coding sequence encodes glutamine at this position. The vip3Aa19 coding sequence encodes an insect control protein, Vip3Aa19 that provides resistance to lepidopteran insects. The second expression cassette is comprised of a ZmUbiInt promoter operably linked to a pmi coding sequence (also known as *E. coli* manA) encoding phosphomannose isomerase (GenBank® Accession number M15380), which catalyzes the isomerization of mannose-6-phosphate to fructose-6-phosphate (Negrotto et al., 2000). The pmi coding sequence is further operably linked to a nopaline synthase 3' end transcription termination and polyadenylation sequence.

Immature embryos were excised from 8-12 day old ears and rinsed with fresh medium in preparation for transformation. Embryos were mixed with the suspension of *Agrobacterium* cells harboring the transformation vector pNOV1300, vortexed for 30 seconds, and allowed to incubate for an additional 5 minutes. Excess solution containing *Agrobacterium* was aspirated and embryos were then moved to plates containing a non-selective culture medium. Embryos were co-cultured with the remaining *Agrobacterium* at 22° C. for 2-3 days in the dark. Embryos were transferred to culture medium supplemented with ticarcillin (100 mg/ml) and silver nitrate (1.6 mg/l) and incubated in the dark for 10 days. Embryos producing embryogenic callus were transferred to cell culture medium containing mannose.

Regenerated plantlets were tested by TAQMAN® PCR analysis (see Example 2) for the presence of both the pmi and vip3Aa19 genes, as well as for the absence of the antibiotic resistance spectinomycin (spec) gene. It was later discovered (See Example 4 below) that during the transformation process two mutations were introduced into the vip3Aa19 coding sequence, one of which resuled in an amino acid change in the Vip3Aa19 protein. Therefore, this new vip3Aa coding sequence, which is unique to event MIR162, was designated vip3Aa20. The vip3Aa20 coding sequence encodes isoleucine at position 129 in place of the methionine residue encoded by the vip3Aa19 gene.

Plants positive for both transgenes, and negative for the spec gene, were transferred to the greenhouse for further propagation. Positive events were identified and screened using insect bioassays against fall armyworm. Insecticidal events were characterized for copy number by TAQMAN analysis. MIR162 was chosen for further analysis based on having a single copy of the transgenes, good protein expression as identified by ELISA, and good insecticidal activity against fall armyworm.

The breeding pedigree of the MIR162 event was as follows: To MIR162 plant (x NPH8431)→→NPH8431 (MIR162)$F_1$ (xNP2161)→NP2161(MIR162)$F_1$(x NP2161)→ NP2161 (MIR162) BC1$F_1$ (x B9620)→$F_1$(x B9620)→ BC1$F_1$(x B9620)→BC2$F_1$(x B9620)→BC3$F_1$(x B9620)→ BC4$F_1$(x B9620). Plant material from the BC4 generation was used for the Southern analysis, copy number determination and sequencing of the insert DNA. Negative controls for the experiments consisted of 10 negative segregant plants from the BC4 generation.

Example 2

MIR162 Detection by TAQMAN PCR

TAQMAN analysis was essentially carried out as described in Ingham et al. (Biotechniques, 31:132-140, 2001) herein incorporated by reference. Briefly, genomic DNA was isolated from leaves of transgenic and non-transgenic corn plants using the Puregene® Genomic DNA Extraction kit (Gentra Systems, Minneapolis, Minn.) essentially according to the manufacturer's instruction, except all steps were conducted in 1.2 ml 96-well plates. The dried DNA pellet was resuspended in TE buffer (10 Mm Tris-HCl, pH 8.0, 1 mM EDTA).

TAQMAN PCR reactions were carried out in 96-well plates. For the endogenous corn gene control, primers and probes were designed specific to the *Zea mays* alcohol dehydrogenase (adhI) coding sequence (Genbank accession no. AF044295). It will be recognized by the skilled person that other corn genes can be used as endogenous controls. Reactions were multiplexed to simultaneously amplify vip3Aa and adhI or pmi and adhI. For each sample, a master mixture was generated by combining 20 μL extracted genomic DNA with 35 μL 2× TAQMAN Universal PCR Master Mix (Applied Biosystems) supplemented with primers to a final concentration of 900 nM each, probes to a final concentration of 100 nM each, and water to a 70 μL final volume. This mixture was distributed into three replicates of 20 μL each in 96-well amplification plates and sealed with optically clear heat seal film (Marsh Bio Products). PCR was run in the ABI Prism 7700 instrument using the following amplification parameters: 2 min at 50° C. and 10 min at 95° C., followed by 35 cycles of 15 s at 95° C. and 1 min at 60° C.

Results of the TAQMAN analysis demonstrated that event MIR162 had one copy of the vip3Aa20 gene and one copy of the pmi gene.

Primers and, probes that were used in the TAQMAN PCR reactions are shown in Table 1.

TABLE 1

Primers used in TAQMAN Assay.

| Primer Name | Primer Sequence | Sequence No: |
|---|---|---|
| Vip3Aa-forward | 5'CACCTtCAGCAACCCGAACTA3' | SEQ ID NO: 4 |
| Vip3Aa-reverse | 5'GCTTAGCCTCCACGATCATCTT3' | SEQ ID NO: 5 |
| Vip3Aa-probe | 5'GTCCTCGTCGCTGCCCTTCACCT3' (5' label = FAM, 3' label = TAMRA) | SEQ ID NO: 6 |
| PMI-forward | 5'CCGGGTGAATCAGCGTTT3' | SEQ ID NO: 7 |
| PMI-reverse | 5'GCCGTGGCCTTTGACAGT3' | SEQ ID NO: 8 |
| PMI-probe | 5'TGCCGCCAACGAATCACCGG3' (5' label = FAM, 3'label = TAMRA) | SEQ ID NO: 9 |
| ZmADH-267 forward | 5'GAACGTGTGTTGGGTTTGCAT3' | SEQ ID NO: 10 |
| ZmADH-337 reverse | 5'TCCAGCAATCCTTGCACCTT3' | SEQ ID NO: 11 |
| ZmADH-316 probe | 5'TGCAGCCTAACCATGCGCAGGGTA3' (5'label = TET, 3' label = TAMRA) | SEQ ID NO: 12 |

Example 3

MIR162 Detection by Southern Blot

Genomic DNA used for southern analysis was isolated from pooled leaf tissue of 10 plants representing the BC4 generation of MIR162 using essentially the method of Thomas et al. (Theor. Appl. Genet. 86:173-180, 1993), incorporated herein by reference. All plants used for DNA isolation were individually analyzed using TAQMAN PCR (as described in Example 2) to confirm the presence of a single copy of the vip3Aa20 gene and the pmi gene. For the negative segregant controls, DNA was isolated from pooled leaf tissue of negative segregants from the BC4 generation. These negative segregant plants were individually analyzed using TAQMAN PCR to confirm the absence of the vip3Aa20 and pmi genes, but were, as expected, positive for the endogenous maize adhI gene.

Southern analysis was carried out using conventional molecular biology techniques. (See Chomczynski, P. 1992. Analytical Biochemistry 201:34-139) Genomic DNA (7.5 μg) was digested with restriction enzymes that digest within the event MIR162 insert, but not within the coding sequence that corresponds to the specific probe used in the experiment. This approach allowed for determination of the number of copies of each gene, corresponding to the specific probe used for each Southern analysis, which was incorporated into event MIR162.

Another series of restriction digests was performed in which the insert was digested with restriction enzymes that would release a fragment of known size from the insert. This approach provided additional evidence for the presence of a single copy of each coding sequence present in MIR162 and allowed for the detection of partial copies of the insert that may be closely linked to the MIR162 insert. Following agarose gel electrophoresis and alkaline transfer to a Zeta-Probe® GT membrane (Bio-Rad, Cat. No. 162-0195), hybridizations were carried out using full-length PCR generated element probes. The probes were labeled with $^{32}P$ via random priming using the MegaPrime™ system (Amersham Biosciences, Cat. No. $RPN_{1607}$). Hybridization was carried out at 65° C., followed by multiple washes in 2×SSC, 0.1% SDS and then 0.1×SSC and 0.1% SDS. The membranes were then subjected to autoradiography.

Included in each Southern analysis were three control samples: (1) DNA from a negative (non-transformed) segregant used to identify any endogenous *Zea mays* sequences that may cross-hybridize with the element-specific probe; (2) DNA from a negative segregant into which is introduced an amount of digested pNOV1300 that is equal to one copy number based on plasmid size was introduced, to demonstrate the sensitivity of the experiment in detecting a single gene copy within the *Zea mays* genome; and (3) Digesled pNOV1300 plasmid equal to one copy number based on plasmid size, to act as a positive control for hybridization as well as to demonstrate the sensitivity of the experiment.

The results of Southern analyses demonstrated that the MIR162 insert contains a single copy of the vip3Aa20 gene and pmi gene and contains no pNOV1300 backbone sequences. A vip3Aa19 probe (SEQ ID NO: 13) was used for the vip3Aa20 Southern analysis. The nucleotide sequences of vip3Aa19 and vip3Aa20 differ by two nucleotides and are 99.9% identical. Therefore, the vip3Aa19 probe hybridized to the vip3Aa20 sequence present in MIR162 under stringent conditions. Using the vip3Aa19 probe, a KpnI and an EcoRV digest resulted in single hybridization bands approximately 8 kb and 13 kb in size, respectively. In addition, an NcoI double digest resulted in a single hybridization band consistent with the expected size of 4.6 kb. Using the pmi probe (SEQ ID NO: 14), a Acc65I and a BamHI digest resulted in single hybridization bands of approximately 4 kb and 6 kb in size, respectively. In addition, an XmaI+HindIII double digest resulted in a single hybridization band consistent with the expected size of 8.1 kb. The 8.1 kb XmaI+HindIII pNOV1300 band (positive control) also hybridized with the vip3Aa19 and pmi probes as expected. Some cross-hybridization in the plasmid-only lanes with the DNA ladder probe was detected. Typically commercially available DNA ladders may contain some vector sequences that can cross-hybridize with the plasmid control sequences as observed in these experiments, but, this does not impact the findings of this study. Finally, a pNOV1300 backbone probe did not hybridize demonstrating the absence of incorporation of any pNOV1300 vector backbone sequences into MIR162 during the transformation process.

Example 4

Heterologous DNA Insert Sequencing

The nucleotide sequence of the vip3Aa and pmi coding sequences in the heterologous DNA molecule inserted in MIR162 was determined to demonstrate overall integrity of the insert, contiguousness of the functional elements and to detect any individual basepair changes. The coding sequences were amplified from DNA derived from the BC4 generation. PCR amplification was carried out using either Expand High Fidelity PCR system (Roche, Cat. No. 1732650) or PfuUltra™ Hotstart High-Fidelity DNA polymerase (Stratagene, Cat. No. 600390). Each PCR product was individually cloned into either pCR®-XL-TOPO vector (Invitrogen, Cat. No. K4700-20) or pCR®-BluntII-TOPO vector (Invitrogen, Cat. No. K2800-20) and three separate clones for each PCR product were identified and sequenced. Sequencing was carried out using the ABI3730XL analyzer using ABI BigDye® 1.1 or Big Dye 3.1 dGTP (for GC-rich templates) chemistry. The sequence analysis was done using the Phred, Phrap, and Consed package from the University of Washington and was carried out to an error rate of less than 1 in 10,000 bases (Ewing & Green, 1998. Genome Research 8:186-194). The final consensus sequence for each gene was determined by combining the sequence data from the three individual clones to generate one consensus sequence for each gene. Sequence alignment was performed using the ClustalW program with the following parameters: scoring matrix blosum55, gap opening penalty 15, gap extension penalty 6.66 (Thompson et al, 1994. Nucleic Acids Research 22:4673-4680).

The full vip3Aa20 coding sequence was PCR amplified using primers MOV3Aa-01-5': 5'ATGAACAAGAACAACACCAA3' (SEQ ID NO: 15) and MOV3Aa-01-3': 5'CTACTTGATGCTCACGTCGTAG3' (SEQ ID NO: 16) and PfuUltra Hotstart enzyme generating a 2370 bp product. The PCR amplicon was sequenced using the primers shown in Table 2.

TABLE 2

| Primer Name | Sequence (5'→3') | Sequence No. |
|---|---|---|
| b03503b | ACGAGCAGAACCAGGTGC | SEQ ID NO: 17 |
| b03503c | GGTGAAGAAGGACGGCAG | SEQ ID NO: 18 |
| b03503d | ACCTGTCGCAAGCTGCTGGG | SEQ ID NO: 19 |
| b03503e | TGGACAAGCTGCTGTGTC | SEQ ID NO: 20 |
| b03503f | TGCAGGCCGACGAGAACAG | SEQ ID NO: 21 |
| b03503g | TGATCCAGTACACCGTGAA | SEQ ID NO: 22 |
| b03503h | ACCCTGACCCTGTACCAG | SEQ ID NO: 23 |
| b03504b | GTGTTGCCGCTGATGTTG | SEQ ID NO: 24 |
| b03504c | CGTACTCGGTCTTCGGCT | SEQ ID NO: 25 |
| b03504d | CTGCAGGCCAAAGCCGTT | SEQ ID NO: 26 |
| b03504e | TCGCCGTAGATCACCTCG | SEQ ID NO: 27 |
| b03504f | GCTTGCGACAGGTGGTCA | SEQ ID NO: 28 |
| b03504g | TTGCTGCTGGTCTCGGTGG | SEQ ID NO: 29 |
| b03504h | CGTTGGCGATCTTAAGGAT | SEQ ID NO: 30 |
| b00203c | GCAAGCCATCGATTCAC | SEQ ID NO: 31 |
| b00203d | GCAACACCCTGACCCTG | SEQ ID NO: 32 |
| b00203e | TCTACGACGTGAGCATCAAG | SEQ ID NO: 33 |
| b00203f | GTAGAAGTGCACGATCGGG | SEQ ID NO: 34 |
| b00203g | CGGTGCTGGTCCAGTTG | SEQ ID NO: 35 |

Two other PCR reactions overlapped the full vip3Aa20 coding sequence. The 5' end of vip3Aa20 was covered with a PCR amplification using primers 162INSERT-F2: 5'ACACCAATGATGCAAATAGGC3' (SEQ ID NO: 36) and VIP_R4 5'GAAGGTGTTCAGGTAGAACTCGAAG3' (SEQ ID NO: 37) and Expand High Fidelity enzyme. The second reaction covered the 3' end of vip3Aa20; the product was amplified with primers VIP-F3: 5'GGTGCTGTTCGAGAAGAGGT3' (SEQ ID NO: 42) and PMI_REVI: 5'CGATTTATCACTCTCAATCACAT3' (SEQ ID NO: 43) and Expand High Fidelity enzyme. The amplicons generated by these reactions comprised a 2946 bp nucleotide sequence (SEQ ID NO: 38) and a 2577 bp nucleotide sequence (SEQ ID NO: 44), respectively.

The consensus sequence data revealed two nucleotide changes in the vip3Aa coding sequence in MIR162 (designated vip3Aa20; SEQ ID NO: 1) compared to the vip3Aa coding sequence in pNOV1300 (designated vip3Aa19), which was used to transform MIR162. The first nucleotide change, a G to T mutation, occurred at position 387 of the vip3Aa19 coding sequence (SEQ ID NO: 3). This mutation resulted in the methionine at position 129 of Vip3Aa19 being changed to isoleucine in Vip3Aa20 (M129I), SEQ ID NO: 2. The second nucleotide change occurred at position 1683 of the coding sequence, a G to C mutation, but did not result in an amino acid change. Therefore, the vip3Aa20 coding sequence (SEQ ID NO: 1) and the Vip3Aa20 protein (SEQ ID NO: 2) are unique to the MIR162 event and can be used to identify any plant comprising the MIR162 transgenic genotype. The pmi coding sequence MIR162 was identical to that in the transformation plasmid pNOV 1300. An alignment of the Vip3Aa20 and Vip3Aa19 insecticidal proteins is shown in Table 3.

The consensus sequence data revealed two nucleotide changes in the vip3Aa coding sequence in MIR162 (designated vip3Aa20) compared to the vip3Aa coding sequence in pNOV1300 (designated vip3Aa19), which was used to transform MIR162. The first nucleotide change, a G to T mutation, occurred at position 387 of the vip3Aa19 coding sequence (SEQ ID NO: 3). This mutation resulted in the methionine at position 129 of Vip3Aa19 being changed to isoleucine in Vip3Aa20 (M1291). The second nucleotide change occurred at position 1683 of the coding sequence, a G to C mutation, but did not result in an amino acid change. Therefore, the vip3Aa20 coding sequence and the Vip3Aa20 protein are unique to the MIR162 event and can be used to identify any plant comprising the MIR162 transgenic genotype. The pmi coding sequence MIR162 was identical to that in the transformation plasmid pNOV1300. An alignment of the Vip3Aa20 and Vip3Aa19 insecticidal proteins is shown in Table 3.

TABLE 3

Comparison of Vip3Aa20 and Vip3Aa19 amino acid sequences.

| Name | | Sequence Alignment |
|---|---|---|
| Vip3Aa20 | (1) | MNKNNTKLSTRALPSFIDYFNGIYGFATGIKDIMNMIFKTDTGGDLTLDE |
| Vip3Aa19 | (1) | MNKNNTKLSTRALPSFIDYFNGIYGFATGIKDIMNMIFKTDTGGDLTLDE |
| Vip3Aa20 | (51) | ILKNQQLLNDISGKLDGVNGSLNDLIAQGNLNTELSKEILKIANEQNQVL |
| Vip3Aa19 | (51) | ILKNQQLLNDISGKLDGVNGSLNDLIAQGNLNTELSKEILKIANEQNQVL |
| Vip3Aa20 | (101) | NDVNNKLDAINTMLRVYLPKITSMLSDVIKQNYALSLQIEYLSKQLQEIS |
| Vip3Aa19 | (101) | NDVNNKLDAINTMLRVYLPKITSMLSDVMKQNYALSLQIEYLSKQLQEIS |
| Vip3Aa20 | (151) | DKLDIINVNVLINSTLTEITPAYQRIKYVNEKFEELTFATETSSKVKKDG |
| Vip3Aa19 | (151) | DKLDIINVNVLINSTLTEITPAYQRIKYVNEKFEELTFATETSSKVKKDG |
| Vip3Aa20 | (201) | SPADILDELTELTELAKSVTKNDVDGFEFYLNTFHDVMVGNNLFGRSALK |
| Vip3Aa19 | (201) | SPADILDELTELTELAKSVTKNDVDGFEFYLNTFHDVMVGNNLFGRSALK |
| Vip3Aa20 | (251) | TASELITKENVKTSGSEVGNVYNFLIVLTALQAQAFLTLTTCRKLLGLAD |
| Vip3Aa19 | (251) | TASELITKENVKTSGSEVGNVYNFLIVLTALQAQAFLTLTTCRKLLGLAD |
| Vip3Aa20 | (301) | IDYTSIMNEHLNKEKEEFRVNILPTLSNTFSNPNYAKVKGSDEDAKMIVE |
| Vip3Aa19 | (301) | IDYTSIMNEHLNKEKEEFRVNILPTLSNTFSNPNYAKVKGSDEDAKMIVE |
| Vip3Aa20 | (351) | AKPGHALIGFEISNDSITVLKVYEAKLKQNYQVDKDSLSEVIYGDMDKLL |
| Vip3Aa19 | (351) | AKPGHALIGFEISNDSITVLKVYEAKLKQNYQVDKDSLSEVIYGDMDKLL |
| Vip3Aa20 | (401) | CPDQSEQIYYTNNIVFPNEYVITKIDFTKKMKTLRYEVTANFYDSSTGEI |
| Vip3Aa19 | (401) | CPDQSEQIYYTNNIVFPNEYVITKIDFTKKMKTLRYEVTANFYDSSTGEI |
| Vip3Aa20 | (451) | DLNKKKVESSEAEYRTLSANDDGVYMPLGVISETFLTPINGFGLQADENS |
| Vip3Aa19 | (451) | DLNKKKVESSEAEYRTLSANDDGVYMPLGVISETFLTPINGFGLQADENS |
| Vip3Aa20 | (501) | RLITLTCKSYLRELLLATDLSNKETKLIVPPSGFISNIVENGSIEEDNLE |
| Vip3Aa19 | (501) | RLITLTCKSYLRELLLATDLSNKETKLIVPPSGFISNIVENGSIEEDNLE |
| Vip3Aa20 | (551) | PWKANNKNAYVDHTGGVNGTKALYVHKDGGISQFIGDKLKPKTEYVIQYT |
| Vip3Aa19 | (551) | PWKANNKNAYVDHTGGVNGTKALYVHKDGGISQFIGDKLKPKTEYVIQYT |
| Vip3Aa20 | (601) | VKGKPSIHLKDENTGYIHYEDTNNNLEDYQTINKRFTTGTDLKGVYLILK |
| Vip3Aa19 | (601) | VKGKPSIHLKDENTGYIHYEDTNNNLEDYQTINKRFTTGTDLKGVYLILK |
| Vip3Aa20 | (651) | SQNGDEAWGDNFIILEISPSEKLLSPELINTNNWTSTGSTNISGNTLTLY |
| Vip3Aa19 | (651) | SQNGDEAWGDNFIILEISPSEKLLSPELINTNNWTSTGSTNISGNTLTLY |
| Vip3Aa20 | (701) | QGGRGILKQNLQLDSFSTYRVYFSVSGDANVRIRNSREVLFEKRYMSGAK |
| Vip3Aa19 | (701) | QGGRGILKQNLQLDSFSTYRVYFSVSGDANVRIRNSREVLFEKRYMSGAK |
| Vip3Aa20 | (751) | DVSEMFTTKFEKDNFYIELSQGNNLYGGPIVHFYDVSIK |
| Vip3AA19 | (751) | DVSEMFTTKFEKDNFYIELSQGNNLYGGPIVHFYDVSIK |

The shaded box indicates the amino acid change.

Example 5

Analysis of Flanking DNA Sequence

A number of methods are known to those of skill in the art to amplify unknown DNA sequences adjacent to a core region of known sequence. Those methods include, but are not limited to, inverse PCR (iPCR) [Ochman et. al., Genetics 120: 621-623 (1988); Triglia et. al., Nucleic Acids Res. 16:8186 (1988)], panhandle PCR [Jones and Winistorfer, Nucleic Acids Res. 20:595-600 (1992); Jones and Winistorfer, Biotechniques 23:132-138 (1997)], cassette ligation-anchored PCR [Mueller and Wold, Science 246:780-786 (1989)], vectorette-PCR [Riley et. al., Nucleic Acids Res. 18:2887-2890 (1990)], novel-Alu-PCR [Puskas et. al., Nucleic Acids Res. 22:3251-3252 (1994)] and Thermal Asymmetric Interlaced PCR (TAIL-PCR) [Liu and Whittier, Genomics 25:673-681 (1995)].

One method used to amplify corn genome DNA sequence flanking the heterologous DNA inserted into event MIR162 was vectorette PCR essentially as described by Riley et al., Nucleic Acids Res. 18:2887-2890 (1990), incorporated herein by reference.

The 5' flanking sequence and junction sequence was confirmed using standard PCR procedures. The following primer pairs, or complements thereof, were used to confirm the sequence: 162INSERT-F2: 5'ACACCAATGATGCAAATAGGC3' (SEQ ID NO: 36)/VIP_R4: 5'GAAGGTGTTCAGGTAGAACTCGAAG3' (SEQ ID NO: 37) and CJB179: 5'ATGCAAATAGGCTGGGAATAGTC3' (SEQ ID NO: 39)/CJB134 5'GTACCAGCTTGCTGAGTGGCT3' (SEQ ID NO: 40). The resulting amplicon has the sequence shown is SEQ ID NO: 41 and comprises the 5' junction sequence of SEQ ID NO: 45. It will be recognized that other primer sequences can be used to confirm the flanking and junction sequences. Using this method, the MIR162 insert was found to be flanked 5' by nucleotides 1040-1088 of the corn genomic sequence shown in SEQ ID NO: 46.

A larger region of the 5' flanking sequence from event MIR162 was generated using the Seegene DNA Walking SpeedUp™ Premix kit following the manufacturer's instructions.

A first PCR reaction was performed independently in four individual tubes using primer FE1002: 5'CGTGACTCCCTTAATTCTCCGCT3' (SEQ ID NO: 50) with one of the DW-ACP 1, 2, 3, or 4 primers supplied by the manufacturer. The following reagents were mixed in a PCR tube on ice: 100 μg MIR162 genomic DNA, 4 μl 2.5 μM DW-ACP (one each with DW-ACP 1, 2, 3, or 4), 4 μl 2.5 μM FE 1002, 19 μl distilled water, and 25 μl 2× SeeAmp™ ACPTM Master Mix II. The tubes were placed in a preheated (94° C.) thermal cycler. PCR was completed using the following program: one cycle at 94° C. for five minutes, 42° C. for one minute, and 72° C. for two minutes, 30 cycles of 94° C. for 40 seconds, 55° C. for 40 seconds, and 72° C. for 90 seconds, and one cycle at 72° C. for seven minutes. The PCR products were purified using Exonuclease I and Shrimp Alkaline Phosphatase.

A second PCR reaction was performed independently in four individual tubes using primer FE1003: 5'GATCAGATTGTCGTTTCCCGCCTT3' (SEQ ID NO: 51) with the DW-ACPN primer supplied by the manufacturer of the kit. The following reagents were mixed in a PCR tube on ice: 3 μl purified PCR product, 1 μl 10 μM DW-ACPN, 1 μl 10 μM FE1003, 5 μl distilled water, and 10 μl 2× SeeAmp™ ACPTM Master Mix II. The tubes were placed in a preheated (94° C.) thermal cycler. PCR was completed using the following program: one cycle at 94° C. for five minutes, 35 cycles of 94° C. for 40 seconds, 60° C. for 40 seconds, and 72° C. for 90 seconds, and one cycle at 72° C. for seven minutes.

A third PCR reaction was performed independently in four individual tubes using primer FE1004: 5'GATTGTCGTTTCCCGCCTTCAGTT3' (SEQ ID NO: 52) with the Universal primer supplied by the manufacturer. The following reagents were mixed in a PCR tube on ice: 2 μl purified PCR product, 1 μl 10 μM Universal primer, 1 μl 10 μM FE1004, 6 μl distilled water, and 10 μl 2× SeeAmp™ ACPTM Master Mix II. The tubes were placed in a preheated (94° C.) thermal cycler. PCR was completed using the following program: one cycle at 94° C. for five minutes, 35 cycles of 94° C. for 40 seconds, 60° C. for 40 seconds, and 72° C. for 90 seconds, and one cycle at 72° C. for seven minutes.

Ten μl of the PCR products were run on a 1% agarose gel containing ethidium bromide. The appropriate band was extracted from the agarose gel and purified using a Qiagen Qiaquick Gel Extraction Kit according to the manufacturer's instructions. The extracted DNA was cloned into an Invitrogen TOPO-XL cloning vector according to the manufacturer's instructions. This clone was transformed into *E. coli*, and the plasmid DNA was extracted from the cells after overnight growth with a Qiagen Miniprep kit according to the manufacturer's instructions. This plasmid was used for end run sequencing.

A new primer was designed within the new, previously unknown sequence to be used with a primer in the heterologous DNA insert to amplify the full 1 kb of flanking sequence out of the genomic DNA. Flanking sequence primer 162DWConf3: 5'CCTGTGTTGTTGGAACAGACTTCTGTC3' (SEQ ID NO: 53) and insert DNA primer FE0900: 5'GGCTCCTTCAACGTTGCGGTTCTGTC3' (SEQ ID NO: 54) were used to amplify a nucleic acid molecule comprising the 5' flanking sequence for confirmation. The sequence of the resulting amplicon is set forth in SEQ ID NO: 55. This 5' amplicon comprises the 5' junction sequence set forth in SEQ ID NO: 45. Ten μl of the PCR product (amplicon) was run on a 1% agarose gel containing ethidium bromide. The appropriate band was extracted from the agarose gel and purified using a Qiagen Qiaquick Gel Extraction Kit according to the manufacturer's instructions. The extracted DNA was cloned into an Invitrogen TOPO-XL cloning vector according to the manufacturer's instructions. This clone was transformed into *E. coli* Plasmid DNA was extracted from the cells after overnight growth in media with a Qiagen Miniprep kit according to the manufacturer's instructions. Three plasmids were completely sequenced using the primers shown in Table 4. The plasmid sequences were aligned to generate the complete confirmed 5' flanking sequence. Using this method, approximately 1 kb of the 5' flanking sequence (SEQ ID NO: 46) was determined.

TABLE 4

Primer sequences.

| Primer Name | Sequence (5'→3') | Sequence No. |
|---|---|---|
| b00201h | TTCACGGGAGACTTTATCTG | SEQ ID NO: 60 |
| b00605a | CCGATTCATTAATGCAG | SEQ ID NO: 61 |
| b00701b | ACGTAAAACGGCTTGTC | SEQ ID NO: 62 |
| b00702b | GTTTAAACTGAAGGCGG | SEQ ID NO: 63 |
| b00704h | AATAATATCACTCTGTACATCC | SEQ ID NO: 64 |
| b01106f | GTTGTAAAACGAGGG | SEQ ID NO: 65 |
| b01709f | TAGGCACCCCAGGCTTTA | SEQ ID NO: 66 |
| b03504a | AATTGAATTTAGCGGCCG | SEQ ID NO: 67 |
| b05102f | GGTCCCTACAACATAAATAG | SEQ ID NO: 68 |
| b05102g | TTCGTCCCTACTATCAACGC | SEQ ID NO: 69 |
| b05102h | CTTTAGGCATCAGCGGGT | SEQ ID NO: 70 |
| b05103a | AGCATCTGCGTAAGCACA | SEQ ID NO: 71 |
| b05103b | CTGATGACACCAATGATGC | SEQ ID NO: 72 |
| b05103c | GATCAGATTGTCGTTTCCC | SEQ ID NO: 73 |
| b05103d | GCATCATTGGTGTCATCAG | SEQ ID NO: 74 |
| b05103e | TGTGCTTACGCAGATGCT | SEQ ID NO: 75 |
| b05103f | ACCCGCTGATGCCTAAAG | SEQ ID NO: 76 |
| b05103g | GCGTTGATAGTAGGGACGAA | SEQ ID NO: 77 |
| b05103h | CTATTTATGTTGTAGGGACC | SEQ ID NO: 78 |
| b05210a | CTAGACTGGAAAGCGGAG | SEQ ID NO: 79 |
| b05210b | CCACTTTCATCCCTAGTTG | SEQ ID NO: 80 |

The 3' flanking sequence from event MIR162 was generated using the Clonetech GenomeWalker™ Universal kit (Clonetech Laboratories, Inc.) following the manufacturer's instructions.

First, pools of uncloned, adaptor-ligated genomic DNA fragments, known as GenomeWalker "libraries" were constructed. Each library was constructed by digesting the MIR162 genomic DNA with a restriction enzyme (DraI, FcoRV, PvuII, Stui, and XmnI) as follows: For example, 25 μMIR162 genomic DNA (0.1 μg/l), 8 μl restriction enzyme (10 units/μl), 10 μl restriction enzyme buffer (10×), and 57 μl distilled H2O were mixed in a tube and incubated at 37° C. overnight.

DNA was then purified by using several rounds of phenol/chloroform extraction. Finally, the DNA was precipitated and washed with ethanol, dried and dissolved into 20 μl of TE buffer.

To ligate the GenomeWalker Adapter ends to the MIR162 genomic DNA, 4 μl of the digested, purified genonlic DNA was mixed with 1.9 μl of GenomeWalker Adapter (25 μM), 1.6 μl 10× Ligation Buffer, and 0.5 μl T4 DNA Ligase (6 units/μl). These reactions were incubated overnight at 16° C. The reactions were stopped with incubation at 70° C. for five minutes. After the reaction was stopped, 72 μl of TE was added to each tube, and the contents were mixed thoroughly.

A first PCR reaction was performed using primer AP1, supplied by the manufacturer, with different primers designed within the known heterologous insert DNA sequence (Round 1 "gene specific primers" or "GSP1"). The following reagents were mixed in a PCR tube on ice: 1 μl of the appropriate MIR162 DNA library, 1 μl 10 μM AP1, 1 μl 10 μM GSP1, 1 μl 10 mM dNTPs, 5 μl 10× Advantage 2 PCR Buffer, 1 μl of BD Advantage 2 Polymerase, and 40 μl distilled water. PCR was completed using the following program: seven cycles at 94° C. for 25 seconds and 72° C. for four minutes, 32 cycles at 94° C. for 25 seconds and 67° C. for four minutes, and one cycle at 67° C. for four minutes. Each primary PCR reaction was diluted 50-fold by adding 1 μl of the primary PCR product with 49 μl of distilled water. The reactions that worked were (1) the DraI and the XmnI libraries with the GSP1 primer 162GW3F1: 5'TCTCTTGCTAAGCTGGGAGCTCGATCCG3' (SEQ ID NO: 56) and primer AP1.

A second PCR reaction was performed independently using primer AP2, supplied by the manufacturer, with different primers designed within the known heterologous insert DNA sequence (Round 2 "gene specific primers" or "GSP2"). The following reagents were mixed in a PCR tube on ice: 1 μl of the appropriate diluted primary PCR product, 1 μl 10 μM AP2, 1 μM 10 μM GSP2, 1 μl 10 mM dNTPs, 5 μl 10× Advantage 2 PCR Buffer, 1 μl of BD Advantage 2 Polymerase, and 40 μl distilled water. PCR was completed using the following program: five cycles at 94° C. for 25 seconds and 72° C. for four minutes, 20 cycles at 94° C. for 25 seconds and 67° C. for four minutes, and one cycle at 67° C. for four minutes. The reactions that worked were (1) the DraI and the XmnI libraries with the GSP2 primer 162GW3F2: 5'AAGATTGAATCCTGTTGCCGGTCTTGCG3' (SEQ ID NO: 57) and primer AP2.

Ten μl of the PCR products were run on a 1% agarose gel containing ethidium bromide. The appropriate band was extracted from the agarose gel and purified using a Qiagen Qiaquick Gel Extraction Kit according to the manufacturer's instructions. The extracted DNA was cloned into an Invitrogen TOPO-XL cloning vector according to the manufacturer's instructions. This clone was transformed into *E. coli*, and the plasmid DNA was extracted from the cells after overnight growth with a Qiagen Miniprep kit according to the manufacturer's instructions. This plasmid was sequenced using end run sequencing.

A new primer was designed within the new, previously unknown sequence to be used with a primer in the insert DNA to amplify approximately 1 kb of 3' flanking sequence out of the genomic DNA. The insert DNA primer 162GW3F1: 5'TCTCTTGCTAAGCTGGGAGCTCGATCCG3' (SEQ ID NO: 56) and a 3' flanking sequence primer 1623'GWR1: 5CTGGTGAACCGATTTTTACGGAGG3' (SEQ ID NO: 58) were used to amplify a nucleic acid molecule comprising the 3' flanking sequence for confirmation. The sequence of the resulting amplicon is set forth in SEQ ID NO: 59. This 3' amplicon comprises the 3' junction sequence set forth in SEQ ID NO: 47. Ten μl of the PCR amplicon was run on a 1% agarose gel containing ethidium bromide. The appropriate band was extracted from the agarose gel and purified using a Qiagen Qiaquick Gel Extraction Kit according to the manufacturer's instructions. The extracted DNA was cloned into an Invitrogen TOPO-XL cloning vector according to the manufacturer's instructions. This clone was transformed into *E. coli*. Plasmid DNA was extracted from the cells after overnight growth in media with a Qiagen Miniprep kit according to the manufacturer's instructions. Three plasmids were completely sequenced using the primers shown in Table 5. The plasmid sequences were aligned to generate the complete confirmed 3' flanking sequence (SEQ ID NO: 48).

TABLE 5

Primer sequences.

| Primer Name | Sequence (5'→3') | Sequence No. |
|---|---|---|
| b00106a | GATTGAATCCTGTTGCC | SEQ ID NO: 81 |
| b00106b | TCTCATAAATAACGTCATGC | SEQ ID NO: 82 |
| b00108a | TCTGTGGATAACCGTATTAC | SEQ ID NO: 83 |
| b00201h | TTCACGGGAGACTTTATCTG | SEQ ID NO: 60 |
| b00605a | CCGATTCATTAATGCAG | SEQ ID NO: 61 |
| b00704h | AATAATATCACTCTGTACATCC | SEQ ID NO: 64 |
| b00712e | AGTAACATAGATGACACCGC | SEQ ID NO: 84 |
| b01106a | CCAGTGTGCTGGAATTCG | SEQ ID NO: 85 |
| b01106f | GTTGTAAAAGGACGG | SEQ ID NO: 65 |
| b01107h | CCAGTGTGATGGATATCTGC | SEQ ID NO: 86 |
| b01108e | CCAGTGTGCTGGAATTCG | SEQ ID NO: 87 |
| b01111f | CCAGTGTGATGGATATCTGC | SEQ ID NO: 88 |
| b01709f | TAGGCACCCCAGGCTTTA | SEQ ID NO: 66 |
| b02701a | GTGTGCTGGAATTCGCCCTT | SEQ ID NO: 89 |
| b02701e | TATCTGCAGAATTCGCCCTT | SEQ ID NO: 90 |
| b02702a | GTGTGCTGGAATTCGCCCTT | SEQ ID NO: 91 |
| b02702e | TATCTGCAGAATTCGCCCTT | SEQ ID NO: 92 |
| b02703a | GTGTGCTGGAATTCGCCCTT | SEQ ID NO: 93 |
| b02703e | TATCTGCAGAATTCGCCCTT | SEQ ID NO: 94 |
| b02704a | GTGTGCTGGAAFTCGCCCTT | SEQ ID NO: 95 |
| b02811a | GGTCTTGCGATGATTATC | SEQ ID NO: 96 |

TABLE 5-continued

| Primer sequences. | | |
|---|---|---|
| Primer Name | Sequence (5'→*3') | Sequence No. |
| b05104c | GAGAGGAATGGCAGCAGA | SEQ ID NO: 97 |
| b05104d | GATGACGGGTTTGAGATT | SEQ ID NO: 98 |
| b05104e | AATCTCAAACCCGTCATG | SEQ ID NO: 99 |
| b05104f | TCTGCTGCCATTCCTCTC | SEQ ID NO: 100 |
| b05104g | GATCAACCCGGAGAGGAAT | SEQ ID NO: 101 |
| b05104h | CCATGACGGGTTTGAGAT | SEQ ID NO: 102 |
| b05105c | CAACCGACCTGACAAGTGAC | SEQ ID NO: 103 |
| b05105e | ATCTCAAACCCGTCATGG | SEQ ID NO: 104 |
| b05105f | ATTCCTCTCCGGGTTGATC | SEQ ID NO: 105 |

Example 6

Detection of Vip3Aa20 Protein in MIR162 by ELISA

Extracts were prepared from MIR162 leaves, roots, pith, kernels, silk, pollen and whole plants. They were quantitatively analyzed for Vip3Aa20 by ELISA using immunoaffinity purified goat anti-Vip3A and Protein A-purified rabbit anti-Vip3A polyclonal antibodies using art recognized ELISA procedures. Vip3Aa20 was detected in all tissues analyzed across all growth stages. The mean level of Vip3Aa20 protein detected in the whole plant at anthesis and seed maturity was 10 μg/g fresh weight and 16 μg/g fresh weight, respectively. The mean level of Vip3Aa20 protein in leaves at anthesis was 22 μg/g fresh weight.

Example 7

Field Efficacy of MIR162

The MIR162 event was tested in the field for efficacy against fall armyworm (FAW, *Spodoptera frugiperda*), corn earworm (CEW, *Helicoverpa zea*), black cutworm (BCW, *Agrolis ipsilon*), and European corn borer (ECB, *Ostrinia nubilalis*). Performance of the MIR162 event was compared with that of Warrior® (Syngenta, Inc.), a conventional insecticide standard applied at a rate of 11.2 g a.i./acre, the transgenic corn event Bt11, comprising a cry1Ab gene, and a Btl1 X MIR162 hybrid, produced by crossing a Btl1 inbred line with a MIR162 inbred line.

Twenty-eight trials were planted in 13 states that represented the major corn growing regions of the continental United States. Trials were planted in a randomized complete block design with four replicated plots per block. Plots were 17.5 row feet per treatment per replication. Planting density was targeted at approximately 30,000 plants/acre. Immunodiagnostic strips were used to confirm the presence or absence of the Vip3Aa20 and Cry1Ab proteins in the different treatment groups.

Natural pest infestations were utilized in trials where populations were sufficiently high; where they were not, artificial infestations were carried out. Artificial infestation with two $2^{nd}$-to $3^{rd}$-instar larvae at V1-V2 was utilized in the BCW trials. Plots were rated at 3, 7, and 14 days post-infestation. BCW damage was recorded as partially damaged plants and fully cut plants. FAW plots were rated 7 and 14 days post-infestation or after $3^{rd}$ instar larvae were observed in control plants. The following scale was used to evaluate FAW and CEW leaf damage:

0.01—No visible leaf damage
1—Pin-hole damage on a few leaves
2—Small amount of shot-hole damage on a few leaves
3—Shot-hole damage on several leaves
4—Shot-hole damage and lesions on a few leaves
5—Lesions on several leaves
6—Large lesions on several leaves
7—Large lesions and portions eaten away on a few leaves
8—Large lesions and portions eaten away on several leaves
9—Large lesions and portions eaten away on most leaves Plant damage was assessed for both first and second generation ECB. The following scale was used for rating first generation damage, typically when larvae were in the $3^{rd}$ to 4th instar:

1—No visible leaf damage
2—Small amount of shot-hole injury on a few leaves
3—Shot-hole injury common on several leaves
4—Several leaves with shot-holes and elongated lesions
5—Several leaves with elongated lesions
6—Several leaves with elongated lesions about 2.5 cm
7—Long lesions common on about one half of the leaves
8—Long lesions common on about two-thirds of the leaves
9—Most leaves with long lesions Second generation ECB damage was assessed three to four weeks after artificial infestation or the end of the peak egg laying period. The following measurements were taken: number live larvae/stalk, number live larvae/shank, number live larvae/ear, number of tunnels/stalk, cumulative tunnel length (cm)/stalk, cumulative tunnel length (cm)/shank, number tunnels/ear, cumulative tunnel length kernel damage (cm)/ear, and % infested plants.

CEW trials were generally planted late to increase natural infestation levels. Feeding damage to ears was evaluated when CEW larvae on control plants were at the L5-L6 growth stage. Ear ratings included recording the number of larvae observed per ear and length of visible kernel feeding measured from the ear tip to the average lowest kernel destroyed.

Results of the BCW field trial are shown in Table 6. Less than 3% of the MIR162 plants and Btl1 X MIR162 plants were cut by BCW larvae. Significant numbers of Btl1 and control plants were cut. Plants comprising the MIR162 genotype had less BCW feeding damage than the conventional insecticide treated plants.

TABLE 6

| Stalk damage ratings from five trials with BCW at 21 days after infestation. | |
|---|---|
| Treatment | % Cut Plants |
| MIR162 | 2 |
| Bt11 | 42 |
| Bt11 × MIR162 | 3 |
| Warrior Insecticide | 12 |
| Negative Control | 40 |

Damage was measured as percent of total plants cut.

The FAW field trial results are shown in Table 7. FAW feeding damage was measured on a scale of 0.01 to 9. Mean feeding damage in the MIR162 hybrids was very low (<1) and significantly lower than average damage observed in the Bt11 and conventional insecticide treatments. Insect pressure in these trials was heavy with approximately 50 to 100 neonate larvae/plant. Bt11 provided some protection from damage, whereas the conventional insecticide treatment provided no protection, sustaining the same amount of damage as the control.

TABLE 7

Leaf feeding damage ratings from five trials for FAW.

| Treatment | Mean Leaf Damage Rating (0.01-9) |
|---|---|
| MIR162 | 0.90 |
| Bt11 | 2.52 |
| Bt11 × MIR162 | 0.84 |
| Warrior Insecticide | 3.60 |
| Negative Control | 3.78 |

Mean damage ratings at 14 days after infestation are presented for each treatment.

Results of the trials to assess first generation ECB damage are presented in Table 8. ECB feeding damage was rated on a scale of 1-9. In these trials, MIR162 conferred minimal protection against ECB feeding damage. Bt11 fully protected the plants from ECB feeding damage. The Bt11 X MIR162 plants had the same level of protection as the Bt11 plants. The conventional insecticide treatment provided better protection than the MIR162 trait but significantly less protection than that provided by Bt11.

TABLE 8

Leaf feeding damage field trial.

| Treatment | Mean Leaf Damage Rating (1-9) |
|---|---|
| MIR162 | 2.95 |
| Bt11 | 1.00 |
| Bt11 × MIR162 | 1.00 |
| Warrior Insecticide | 2.05 |
| Negative Control | 3.88 |

Mean damage ratings at 14 days after infestation.

Second generation ECB damage results are presented in Table 9. Feeding damaged was measured as cumulative tunnel length in each corn stalk (if more than one tunnel was found, tunnel lengths were summed). The Bt11 and Bt11× MIR162 treatments provided strong protection against stalk boring, whereas no protection against tunneling was provided by MIR162 alone or the insecticide treatment.

TABLE 9

Stalk damage ratings from seven trials for second generation ECB larvae measured in tunnel length (cm) per stalk.

| Treatment | Mean Tunnel Length (cm) |
|---|---|
| MIR162 | 5.46 |
| Bt11 | 0.37 |
| Bt11 × MIR162 | 0.48 |
| Warrior Insecticide | 5.06 |
| Negative Control | 5.04 |

Measurements were taken three to four weeks after artificial infestation.

Results of trials to assess CEW damage are presented in Table 10. Feeding damage was rated as length of kernel damage per ear, measured from the ear tip to the average lowest kernel destroyed. Significant ear damage was observed in the Bt11, insecticide, and check plots. Bt11 provided some level of protection compared to untreated check and was comparable to the protection provided by the conventional insecticide treatment. MIR162 and Bt11×MIR162 provided almost complete protection of the ears from CEW larval feeding damage.

TABLE 10

Ear damage ratings from six trials for CEW measured as average length of feeding damage.

| Treatment | Mean Ear Damage (cm) |
|---|---|
| MIR162 | 0.17 |
| Bt11 | 2.24 |
| Bt11 × MIR162 | 0.02 |
| Warrior Insecticide | 2.20 |
| Negative Control | 3.42 |

Measurements were taken when CEW larvae were L5-L6 in check plants.

Example 8

Efficacy of MIR162Against Western Bean Cutworm

Current commercial transgenic events producing Cry1Ab protein have not provided acceptable levels of protection against the western bean cutworm (WBCW, *Striacosta albicosta*). Therefore, MIR162 alone and stacked with other transgenic genotypes was tested for efficacy against WBCW.

WBCW eggs were collected from wild caught fernale moths. Larvae were fed on a meridic black cutworm diet until use in the experiments. Corn plants were field grown. The following treatments were tested: MIR162, Bt11, MIR604, MIR162X Bt11, MIR162 X MIR604, MIR604X Bt11, Force® (Syngenta, Inc.), a conventional insecticide applied at planting to a negative isoline, and two negative control isolines. MIR604 is a novel transgenic corn event that comprises a cry3A055 gene encoding a protein that is active against corn rootworm (*Diabrotica* spp.) larvae and is disclosed in US Patent Application publication No. 2005/0216970, published Sep. 29, 2005, herein incorporated by reference.

For the experiments, a two-inch piece of green silks and husk was cut from ears from field grown corn plants in each treatment and replication. The terminal brown ends of the silks were removed and the husk discarded. Approximately 1.5 inches of silks were placed in individual 14 ml plastic cups. One larva was then placed in each cup and the cups sealed. Several different stages of larvae were tested ranging from $3^{rd}$ to $6^{th}$-instars. Cups containing silks and larvae were held at natural day length and room temperature for the duration of the experiments. Larval survival was recorded after eight days. Treatments were replicated four times per experiment.

Results of the WBCW experiments are presented in Table 11. Survival of WBCW on silks from the negative isolines and the conventional insecticide treatment were nearly 100%. Survival of WBCW larvae on Bt11 and MIR604 silks, tested either alone or in combination in the same plant, was not different from survival on the negative isolines. Survival of WBCW larvae was reduced when larvae were fed silks from MIR162. The combination of MIR162X Bt11 in the same plant did not decrease survival any further than MIR162 alone. However, surprisingly, when the MIR162 transgenic genotype was stacked with the MIR604 transgenic genotype in the same plant, larval mortality significantly increased compared to MIR162 or MIR604 alone.

TABLE 11

| Percent (±SE) survival of WBCW larvae on corn silks. | | | | | | | |
|---|---|---|---|---|---|---|---|
| | Experiment Number | | | | | | |
| Treatment | 1 | 2 | 3 | 4 | 5 | 6 | 7 |
| Btl1 | 75(25) | 75(25) | 100(0) | 100(0) | 100(0) | 100(0) | 100(0) |
| MIR162 | 25(25) | 0(0) | 0(0) | 50(29) | 50(29) | 50(29) | 0(0) |
| MIR604 | | | | | 100(0) | 100(0) | 100(0) |
| MIR162xBtl1 | 25(25) | 25(25) | 0(0) | 0(0) | 25(25) | 25(25) | 25(25) |
| MIR162xMIR604 | | | | | 0(0) | 25(25) | 50(29) |
| MIR604xBtl1 | | | | | | | 75(25) |
| Force | | | | | 100(0) | 100(0) | 100(0) |
| Neg. Control #1 | 100(0) | 75(25) | 100(0) | 100(0) | 75(25) | 100(0) | 100(0) |
| Neg. Control #2 | 100(0) | 100(0) | 100(0) | 100(0) | 100(0) | 100(0) | 100(0) |

Example 9

Use of Event MIR162 Insertion Site for Targeted Integration in Maize

The MIR162 flanking sequences disclosed in SEQ ID NO: 46 and SEQ ID NO: 48 were used to search maize genomic databases. Identical matches to both flanking sequences where found on a BAC clone, CH201-307P5, of chromosome 5 (NCBI Accession No. AC185313) on Contig 13 (SEQ ID NO: 106). More specifically, the MIR162 insert is on chromosome 5 between a 5' molecular marker, designated herein as the Opie2 marker (nucleotides 1680-3338 of SEQ ID NO: 106), and a 3' molecular marker, designated herein as the gag marker (nucleotides 43,275-45,086 of SEQ ID NO: 106). Using this information, it was determined that the heterologous DNA inserted into MIR162 displaced 58 nucleotides of maize genomic DNA, nucleotides 25,455 to 25,512 of SEQ ID NO: 106 (also shown as SEQ ID NO: 107), which is between the 5' flanking sequence (nucleotides 1-25,454 of SEQ ID NO: 106) and the 3' flanking sequence (nucleotides 25,513-51,328 of SEQ ID NO: 106).

Consistent agronomic performance of the transgene of event MIR162 over several generations under field conditions suggests that these identified regions around the MIR162 insertion site provide good genomic locations for the targeted integration of other transgenic genes of interest. Such targeted integration overcomes the problems with so-called "positions effects," and the risk of creating a mutation in the genome upon integration of the transgene into the host. Further advantages of such targeted integration include, but are not limited to, reducing the large number of transformation events that must be screened and tested before obtaining a transgenic plant that exhibits the desired level of transgene expression without also exhibiting abnormalities resulting from the inadvertent insertion of the transgene into an important locus in the host genome. Moreover, such targeted integration allows for stacking transgenes rendering the breeding of elite plant lines with both genes more efficient.

Using the above disclosed teaching, the skilled person is able to use methods know in the art to target heterologous nucleic acids of interest to the same insertion site on chromosome 5 as that in MIR162 or to a site in close proximity to the insertion site in MIR162. One such method is disclosed in US Patent Application Publication No. 20060253918, herein incorporated by reference in its entirety. Briefly, up to 20 Kb of the genomic sequence flanking 5' to the insertion site (nucleotides 5,454 to 25,454 of SEQ ID NO: 106) and up to 20 Kb of the genomic sequence flanking 3' to the insertion site (nucleotides 25,513 to 45,513 of SEQ OD NO: 106) are used to flank the gene or genes of interest that are intended to be inserted into a genomic location on Chromosome 5 via homologous recombination. These sequences can be further flanked by T-DNA border repeats such as the left border (LB) and right border (RB) repeat sequences and other booster sequences for enhancing T-DNA delivery efficiency. The gene or genes of interest can be placed exactly as in the MIR162 insertion site or can be placed anywhere within the 20 Kb regions around the MIR162 insertion sites to confer consistent level of transgene expression without detrimental effects on the plant. The DNA vectors containing the gene or genes of interest and flanking sequences can be delivered into plant cells via one of the several methods known to those skilled in the art, including but not limited to *Agrobacterium*-mediated transformation. The insertion of the DNA vector into the MIR162 target site can be further enhanced by one of the several methods, including but not limited to the co-expression or up-regulation of recombination enhancing genes or down-regulation of endogenous recombination suppression genes. Furthermore, it is known in the art that cleavage of specific sequences in the genome can be used to increase homologous recombination frequency, therefore insertion into the MIR162 insertion site and its flanking regions can be enhanced by expression of natural or designed sequence-specific endonucleases for cleaving these sequences. Thus, using the teaching provided herein, any heterologous nucleic acid can be inserted on maize chromosome 5 at a target site located between nucleotides 25,454 and 45,513 of SEQ ID NO: 106 or a target site in the vicinity to this site.

Example 10

Use of Event MIR162 Insertion Site and Flanking Sequences for Stabilization of Gene Expression The genomic sequences flanking the MIR162 insertion site may also be used to stabilize expression of other gene(s) of interest when inserted as a transgene in other genomic locations in maize and other crops. Specifically, up to 20 Kb of the genomic sequence flanking 5' to the insertion site (nucleotides 5,454 to 25,454 of SEQ ID NO: 106) and up to 20 Kb of the genomic sequence flanking 3' to the insertion site (nucleotides 25,513 to 45,513 of SEQ OD NO: 106) are used to flank the gene or genes of interest that are intended to be inserted into the genome of plants. These sequences can be further flanked by T-DNA border repeats such as the left border (LB) and right border (RB) repeat sequences and other booster sequences for enhancing T-DNA delivery efficiency.

The gene or genes of interest can be placed exactly as in the MIR162 insertion site or can be placed anywhere within the 20 Kb regions around the MIR162 insertion sites to confer consistent level of transgene expression. The DNA vectors containing the gene or genes of interest and MIR162 insertion site flanking sequence can be delivered into plant cells via one of the several methods known to those skilled in the art, including but not limited to protoplast transformation, biolistic bombardment and *Agrobacterium*-mediated transformation. The delivered DNA can be integrated randomly into a plant genome or can also be present as part of the independently segregating genetic units such as artificial chromosome or mini-chromosome. The DNA vectors containing the gene(s) of interest and the MIR162 insertion site flanking sequences can be delivered into plant cells. Thus, by surrounding a gene or genes of interest with the genomic sequence flanking the MIR162 insertion site, the expression of such genes are stabilized in a transgenic host plant such as a dicot plant or a monocot plant like corn.

Deposit

Applicants have made a deposit of corn seed of event MIR162 disclosed above on 23 Jan. 2007 in accordance with the Budapest Treaty at the American Type Culture Collection (ATCC), 1801 University Boulevard, Manassas, Va. 20110 under ATCC Accession No. PTA-8166. The deposit will be maintained in the depositary for a period of 30 years, or 5 years after the last request, or the effective life of the patent, whichever is longer, and will be replaced as necessary during that period. Applicants impose no restrictions on the availability of the deposited material from the ATCC; however, Applicants have no authority to waive any restrictions imposed by law on the transfer of biological material or its transportation in commerce. Applicants do not waive any infringement of their rights granted under this patent or under the Plant Variety Protection Act (7 USC 2321 et seq.).

All publications and published patent documents cited in this specification are incorporated herein by reference to the same extent as if each individual publication or patent document was specifically and individually indicated to be incorporated by reference.

What is claimed is:

1. A MIR162 corn plant, or cells or tissues thereof, comprising a nucleic acid molecule selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the complements thereof.

2. A MIR162 corn seed comprising a nucleic acid molecule selected from the group consisting of SEQ ID NO: 1, SEQ ID NO: 38, SEQ ID NO: 41, SEQ ID NO: 45, SEQ ID NO: 47, SEQ ID NO: 49, SEQ ID NO: 55, SEQ ID NO: 59, and the complements thereof, an example of the seed being deposited at the American Type Culture Collection under the accession number PTA-8166.

3. A biological sample derived from a event MIR162 corn plant, tissue, or seed, wherein the sample comprises a nucleotide sequence which is or is complementary to SEQ ID NO: 1, SEQ ID NO: 38, SEQ ID NO: 41, SEQ ID NO: 45, SEQ ID NO: 47, SEQ ID NO: 49, SEQ ID NO: 55, or SEQ ID NO: 59 and wherein the sequence is detectable in the sample using a nucleic acid amplification or nucleic acid hybridization method.

4. The biological sample of claim 3 wherein the sample is selected from the group consisting of corn flour, corn meal, corn syrup, corn oil, corn starch, and cereals manufactured in whole or in part to contain corn by-products.

5. An extract derived from the biological sample according to claim 3, wherein the extract comprises a nucleotide sequence which is or is complementary to SEQ ID NO: 1, SEQ ID NO: 38, SEQ ID NO: 41, SEQ ID NO: 45, SEQ ID NO: 47, SEQ ID NO: 49, SEQ ID NO: 55, or SEQ ID NO: 59 and wherein the sequence is detectable in the extract using a nucleic acid amplification or nucleic acid hybridization method.

6. The extract of claim 5 wherein the sample is selected from the group consisting of corn flour, corn meal, corn syrup, corn oil, corn starch, and cereals manufactured in whole or in part to contain corn by-products.

7. A method for producing a corn plant resistant to lepidopteran pests comprising:

(a) sexually crossing a first parent corn plant with a second parent corn plant, wherein said first or second parent corn plant comprises event MIR162 DNA, thereby producing a plurality of first generation progeny plants;

(b) selecting a first generation progeny plant that is resistant to lepidopteran insect infestation;

(c) selfing the first generation progeny plant, thereby producing a plurality of second generation progeny plants;

(d) selecting from the second generation progeny plants, a plant that is resistant to lepidopteran pests;

wherein the second generation progeny plants comprise SEQ ID NO: 1, SEQ ID NO: 38, SEQ ID NO: 41, SEQ ID NO: 45, SEQ ID NO: 47, SEQ ID NO: 49, SEQ ID NO: 55, or SEQ ID NO: 59.

8. A method of producing hybrid corn seeds comprising:

(a) planting seeds of a first inbred corn line comprising event MIR162 DNA and seeds of a second inbred line having a genotype different from the the first inbred corn line;

(b) cultivating corn plants resulting from said planting until time of flowering;

(c) emasculating said flowers of plants of one of the corn inbred lines;

(d) sexually crossing the two different inbred lines with each other; and (e) harvesting the hybrid seed produced thereby;

wherein the hybrid corn seeds comprise SEQ ID NO: 1, SEQ ID NO: 38, SEQ ID NO: 41, SEQ ID NO: 45, SEQ ID NO: 47, SEQ ID NO: 49, SEQ ID NO: 55, or SEQ ID NO: 59.

9. The method according to claim 8, wherein the plants of the first inbred corn line are the female parents or male parents.

10. Hybrid seed produced by the method of claim 8.

11. A transgenic non-human host cell comprising event MIR162 DNA comprising a nucleic acid molecule selected from the group consisting of SEQ ID NO: 1, SEQ ID NO: 38, SEQ ID NO: 41, SEQ ID NO: 45, SEQ ID NO: 47, SEQ ID NO: 49, SEQ ID NO:

55, SEQ ID NO: 59, and the complements thereof.

* * * * *